(12) United States Patent
Hatakeyama et al.

(10) Patent No.: US 10,613,436 B2
(45) Date of Patent: Apr. 7, 2020

(54) RESIST COMPOSITION AND PATTERNING PROCESS

(71) Applicant: Shin-Etsu Chemical Co., Ltd., Tokyo (JP)

(72) Inventors: Jun Hatakeyama, Joetsu (JP); Masaki Ohashi, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 44 days.

(21) Appl. No.: 15/920,641

(22) Filed: Mar. 14, 2018

(65) Prior Publication Data
US 2018/0275512 A1  Sep. 27, 2018

(30) Foreign Application Priority Data

Mar. 22, 2017  (JP) ................. 2017-055799

(51) Int. Cl.
| *G03F 7/004* | (2006.01) |
| --- | --- |
| *G03F 7/38* | (2006.01) |
| *G03F 7/039* | (2006.01) |
| *G03F 7/038* | (2006.01) |
| *G03F 7/16* | (2006.01) |
| *G03F 7/20* | (2006.01) |
| *G03F 7/32* | (2006.01) |
| *C08F 220/38* | (2006.01) |
| *C08F 220/16* | (2006.01) |
| *C08F 220/22* | (2006.01) |
| *C08F 220/26* | (2006.01) |
| *C08F 220/28* | (2006.01) |
| *C08F 220/20* | (2006.01) |
| *C08F 220/24* | (2006.01) |
| *C08F 228/02* | (2006.01) |
| *C08F 222/16* | (2006.01) |
| *C08F 222/18* | (2006.01) |
| *C08F 222/20* | (2006.01) |
| *C08F 224/00* | (2006.01) |
| *C08F 222/24* | (2006.01) |
| *C08F 222/14* | (2006.01) |
| *C07C 309/32* | (2006.01) |
| *C07C 309/15* | (2006.01) |
| *C07C 309/31* | (2006.01) |
| *C07C 309/46* | (2006.01) |
| *C07C 309/30* | (2006.01) |
| *C07C 309/51* | (2006.01) |
| *C07C 303/32* | (2006.01) |
| *C07C 309/07* | (2006.01) |
| *C07C 309/12* | (2006.01) |
| *C07C 309/48* | (2006.01) |

(Continued)

(52) U.S. Cl.
CPC .......... *G03F 7/0045* (2013.01); *C07C 69/635* (2013.01); *C07C 303/32* (2013.01); *C07C 309/04* (2013.01); *C07C 309/06* (2013.01); *C07C 309/07* (2013.01); *C07C 309/12* (2013.01); *C07C 309/15* (2013.01); *C07C 309/30* (2013.01); *C07C 309/31* (2013.01); *C07C 309/32* (2013.01); *C07C 309/39* (2013.01); *C07C 309/46* (2013.01); *C07C 309/48* (2013.01); *C07C 309/51* (2013.01); *C07C 309/56* (2013.01); *C08F 220/16* (2013.01); *C08F 220/20* (2013.01); *C08F 220/22* (2013.01); *C08F 220/24* (2013.01); *C08F 220/26* (2013.01); *C08F 220/28* (2013.01); *C08F 220/38* (2013.01); *C08F 222/14* (2013.01); *C08F 222/16* (2013.01); *C08F 222/18* (2013.01); *C08F 222/20* (2013.01); *C08F 222/24* (2013.01); *C08F 224/00* (2013.01); *C08F 228/02* (2013.01); *G03F 7/0382* (2013.01); *G03F 7/0397* (2013.01); *G03F 7/162* (2013.01); *G03F 7/168* (2013.01); *G03F 7/2004* (2013.01); *G03F 7/2006* (2013.01); *G03F 7/2037* (2013.01); *G03F 7/2041* (2013.01); *G03F 7/322* (2013.01); *G03F 7/327* (2013.01); *G03F 7/38* (2013.01); *C08F 2220/281* (2013.01); *C08F 2220/282* (2013.01); *C08F 2220/283* (2013.01); *C08F 2220/301* (2013.01); *C08F 2220/302* (2013.01); *C08F 2220/382* (2013.01)

(58) Field of Classification Search
CPC .... G03F 7/0045; G03F 7/0382; G03F 7/0397; G03F 7/38; C08F 220/16; C08F 220/20; C08F 220/22; C08F 220/24; C08F 220/26; C08F 220/28; C08F 2220/281; C08F 2220/282; C08F 2220/283; C08F 2220/301; C08F 2220/302; C08F 220/38; C08F 2220/382; C08F 222/14; C08F 222/16; C08F 222/18; C08F 222/20; C08F 222/24; C08F 224/00; C08F 228/02; C07C 69/635; C07C 303/32; C07C 309/04; C07C 309/06; C07C 309/07; C07C 309/12; C07C 309/15; C07C 309/30; C07C 309/31; C07C 309/32; C07C 309/39; C07C 309/46; C07C 309/48; C07C 309/51; C07C 309/56
USPC .............. 430/270.1, 325, 326, 330
See application file for complete search history.

(56) References Cited

U.S. PATENT DOCUMENTS

| 6,551,758 B2* | 4/2003 | Ohsawa | C07C 309/42 430/270.1 |
| --- | --- | --- | --- |
| 6,692,893 B2* | 2/2004 | Ohsawa | G03F 7/0045 430/270.1 |
| 8,148,044 B2* | 4/2012 | Yamaguchi | C07C 309/17 430/270.1 |

* cited by examiner

*Primary Examiner* — John S Chu
(74) *Attorney, Agent, or Firm* — Westerman, Hattori, Daniels & Adrian, LLP

(57) ABSTRACT

A resist composition comprising a base polymer and a sulfonium or iodonium salt capable of generating fluorobenzenesulfonic acid bonded to iodized benzoic acid offers a (Continued)

high sensitivity and minimal LWR independent of whether it is of positive or negative tone.

13 Claims, No Drawings

(51) Int. Cl.
*C07C 69/635* (2006.01)
*C07C 309/56* (2006.01)
*C07C 309/04* (2006.01)
*C07C 309/06* (2006.01)
*C07C 309/39* (2006.01)
*C08F 220/30* (2006.01)

RESIST COMPOSITION AND PATTERNING PROCESS

CROSS-REFERENCE TO RELATED APPLICATION

This non-provisional application claims priority under 35 U.S.C. § 119(a) on Patent Application No. 2017-055799 filed in Japan on Mar. 22, 2017, the entire contents of which are hereby incorporated by reference.

TECHNICAL FIELD

This invention relates to a resist composition and a pattern forming process.

BACKGROUND ART

To meet the demand for higher integration density and operating speed of LSIs, the effort to reduce the pattern rule is in rapid progress. The wide-spreading flash memory market and the demand for increased storage capacities drive forward the miniaturization technology. As the advanced miniaturization technology, manufacturing of microelectronic devices at the 65-nm node by the ArF lithography has been implemented in a mass scale. Manufacturing of 45-nm node devices by the next generation ArF immersion lithography is approaching to the verge of high-volume application. The candidates for the next generation 32-nm node include ultra-high NA lens immersion lithography using a liquid having a higher refractive index than water in combination with a high refractive index lens and a high refractive index resist film, EUV lithography of wavelength 13.5 nm, and double patterning version of the ArF lithography, on which active research efforts have been made.

As the pattern feature size is reduced, approaching to the diffraction limit of light, light contrast lowers. In the case of positive resist film, a lowering of light contrast leads to reductions of resolution and focus margin of hole and trench patterns.

As the pattern feature size is reduced, the edge roughness (LWR) of line patterns and the critical dimension uniformity (CDU) of hole patterns are regarded significant. It is pointed out that these factors are affected by the segregation or agglomeration of a base polymer and acid generator and the diffusion of generated acid. There is a tendency that as the resist film becomes thinner, LWR becomes greater. A film thickness reduction to comply with the progress of size reduction causes a degradation of LWR, which becomes a serious problem.

The EUV lithography resist must meet high sensitivity, high resolution and low LWR at the same time. As the acid diffusion distance is reduced, LWR is reduced, but sensitivity becomes lower. For example, as the PEB temperature is lowered, the outcome is a reduced LWR, but a lower sensitivity. As the amount of quencher added is increased, the outcome is a reduced LWR, but a lower sensitivity. It is necessary to overcome the tradeoff relation between sensitivity and LWR.

DISCLOSURE OF INVENTION

For the acid-catalyzed chemically amplified resist, it is desired to develop an acid generator capable of providing a high sensitivity and reducing LWR or improving CDU of hole patterns.

An object of the invention is to provide a resist composition which exhibits a high sensitivity and a reduced LWR or improved CDU, independent of whether it is of positive tone or negative tone; and a pattern forming process using the same.

The inventors have found that using a sulfonium or iodonium salt of fluorobenzenesulfonic acid bonded to iodized benzoic acid as the acid generator, a resist material having a reduced LWR, improved CDU, high contrast, improved resolution, and wide process margin is obtainable.

In one aspect, the invention provides a resist composition comprising a base polymer and a sulfonium salt having the formula (A-1) or an iodonium salt having the formula (A-2).

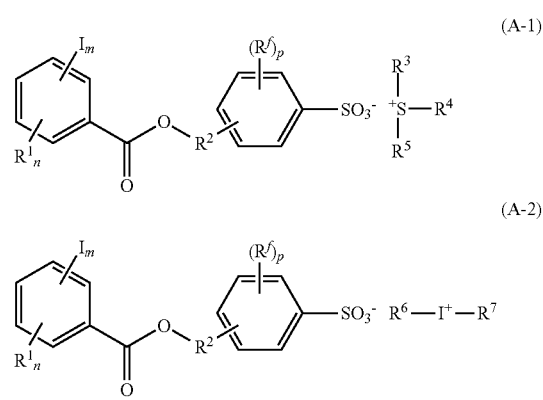

Herein $R^1$ is a hydroxyl group, carboxyl group, fluorine, chlorine, bromine, amino group, or a straight, branched or cyclic $C_1$-$C_{20}$ alkyl, $C_1$-$C_{20}$ alkoxy, $C_2$-$C_{20}$ alkoxycarbonyl or $C_2$-$C_{20}$ acyloxy group which may contain fluorine, chlorine, bromine, hydroxyl, amino or alkoxy moiety, or —$NR^9$—$C(=O)$—$R^{10}$ or —$NR^9$—$C(=O)$—$O$—$R^{10}$, $R^9$ is hydrogen, or a straight, branched or cyclic $C_1$-$C_6$ alkyl group, $R^{10}$ is a straight, branched or cyclic $C_1$-$C_{16}$ alkyl, straight, branched or cyclic $C_2$-$C_{16}$ alkenyl, or $C_6$-$C_{12}$ aryl group which may contain halogen, hydroxyl, alkoxy, acyl or acyloxy moiety. $R^2$ is a single bond, or a divalent $C_1$-$C_{20}$ linking group which may contain oxygen, sulfur or nitrogen. $R^f$ is fluorine or trifluoromethyl. $R^3$, $R^4$ and $R^5$ are each independently fluorine, chlorine, bromine, iodine, $C_1$-$C_{12}$ straight, branched or cyclic alkyl group, $C_2$-$C_{12}$ straight, branched or cyclic alkenyl group, $C_6$-$C_{20}$ aryl group, or $C_7$-$C_{12}$ aralkyl or aryloxyalkyl group, at least one hydrogen in the foregoing groups being optionally substituted by hydroxyl, carboxyl, halogen, oxo, cyano, amide, nitro, sultone, sulfone, or sulfonium salt-containing moiety, or at least one carbon in the foregoing groups being optionally substituted by an ether, ester, carbonyl, carbonate or sulfonate moiety, or $R^3$ and $R^4$ may bond together to form a ring with the sulfur atom to which they are attached. $R^6$ and $R^7$ are each independently trifluoromethyl, a $C_6$-$C_{10}$ aryl group, $C_2$-$C_6$ alkenyl group, or $C_2$-$C_6$ alkynyl group, at least one hydrogen in the foregoing groups being optionally substituted by a halogen, trifluoromethyl, $C_1$-$C_{10}$ straight, branched or cyclic alkyl or alkoxy, hydroxyl, carboxyl, alkoxycarbonyl, nitro or cyano moiety, m is an integer of 1 to 5, n is an integer of 0 to 3, and p is an integer of 1 to 4.

The resist composition may further comprise a quencher and an organic solvent.

In a preferred embodiment, the base polymer comprises recurring units having the formula (a1) or recurring units having the formula (a2).

(a1)

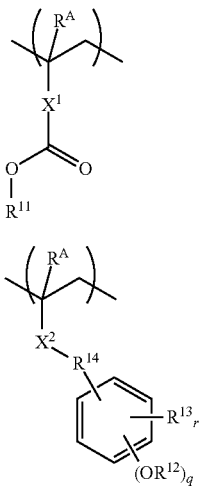

(a2)

(f3)

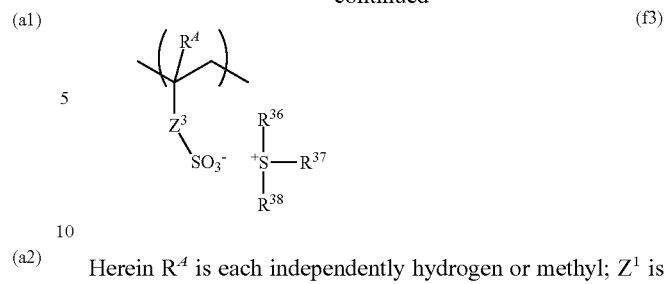

Herein $R^A$ is each independently hydrogen or methyl; $Z^1$ is a single bond, phenylene group, —O—$Z^{12}$— or —C(=O)—$Z^{11}$-$Z^{12}$—, $Z^{11}$ is —O— or —NH—, $Z^{12}$ is a $C_1$-$C_6$ straight, branched or cyclic alkylene group, $C_2$-$C_6$ straight, branched or cyclic alkenylene group or phenylene group, which may contain a carbonyl, ester, ether or hydroxy moiety; $R^{31}$ to $R^{38}$ are each independently a $C_1$-$C_{12}$ straight, branched or cyclic alkyl group which may contain a carbonyl, ester or ether moiety, or a $C_6$-$C_{12}$ aryl group or $C_7$-$C_{20}$ aralkyl group, in which at least one hydrogen may be substituted by a $C_1$-$C_{10}$ straight, branched or cyclic alkyl moiety, halogen, trifluoromethyl, cyano, nitro, hydroxyl, mercapto, $C_1$-$C_{10}$ straight, branched or cyclic alkoxy moiety, $C_2$-$C_{10}$ straight, branched or cyclic alkoxycarbonyl moiety, or $C_2$-$C_{10}$ straight, branched or cyclic acyloxy moiety, any two of $R^{33}$, $R^{34}$ and $R^{35}$, or any two of $R^{36}$, $R^{37}$ and $R^{38}$ may bond together to form a ring with the sulfur atom to which they are attached; $Z^2$ is a single bond, —$Z^{21}$—C(=O)—O—, —$Z^{21}$—O— or —$Z^{21}$—O—C(=O)—, $Z^{21}$ is a $C_1$-$C_{12}$ straight, branched or cyclic alkylene group which may contain a carbonyl, ester or ether moiety; A is hydrogen or trifluoromethyl; $Z^3$ is a single bond, methylene group, ethylene group, phenylene group, fluorinated phenylene group, —O—$Z^{32}$—, or —C(=O)—$Z^{31}$-$Z^{32}$—, $Z^{31}$ is —O— or —NH—, $Z^{32}$ is a $C_2$-$C_6$ straight, branched or cyclic alkylene group, a phenylene, fluorinated phenylene or trifluoromethyl-substituted phenylene group, or $C_2$-$C_6$ straight, branched or cyclic alkenylene group, which may contain a carbonyl, ester, ether or hydroxyl moiety; and $M^-$ is a non-nucleophilic counter ion.

Herein $R^A$ is each independently hydrogen or methyl, $X^1$ is a single bond, phenylene group, naphthylene group, or $C_1$-$C_{12}$ linking group containing an ester moiety and/or lactone ring, $X^2$ is a single bond or ester group, $R^{11}$ and $R^{12}$ each are an acid labile group, $R^{13}$ is fluorine, trifluoromethyl, cyano, $C_1$-$C_6$ straight, branched or cyclic alkyl or alkoxy group, or $C_2$-$C_7$ straight, branched or cyclic acyl, acyloxy or alkoxycarbonyl group, $R^{14}$ is a single bond or a $C_1$-$C_6$ straight or branched alkylene group in which at least one carbon may be substituted by an ether or ester moiety, q is 1 or 2, and r is an integer of 0 to 4.

The resist composition may further comprise a dissolution inhibitor.

In one embodiment, the resist composition is typically a chemically amplified positive resist composition.

In another embodiment, the base polymer is free of an acid labile group. The resist composition may further comprise a crosslinker. The resist composition is typically a chemically amplified negative resist composition.

The resist composition may further comprise a surfactant.

In a preferred embodiment, the base polymer further comprises recurring units of at least one type selected from the formulae (f1) to (f3).

In another aspect, the invention provides a process for forming a pattern comprising the steps of applying the resist composition defined above onto a substrate, baking to form a resist film, exposing the resist film to high-energy radiation, and developing the exposed film in a developer.

In a preferred embodiment, the high-energy radiation is ArF excimer laser radiation of wavelength 193 nm, KrF excimer laser radiation of wavelength 248 nm, EB, or EUV of wavelength 3 to 15 nm.

(f1)

Advantageous Effects of Invention

A sulfonium or iodonium salt of fluorobenzenesulfonic acid bonded to iodized benzoic acid has the advantage of suppressed acid diffusion because of the large atomic weight of iodine. Since iodine is highly absorptive to EUV of wavelength 13.5 nm, it generates numerous secondary electrons during exposure, contributing to a higher sensitivity. A resist material having a high sensitivity, reduced LWR, and improved CDU is obtainable.

(f2)

DESCRIPTION OF EMBODIMENTS

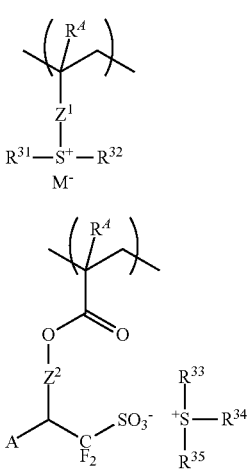

As used herein, the singular forms "a," "an" and "the" include plural referents unless the context clearly dictates otherwise. The notation ($C_n$-$C_m$) means a group containing from n to m carbon atoms per group. As used herein, the term "iodized" compound means an iodine-containing compound. In chemical formulae, Me stands for methyl, Ac for acetyl, and Ph for phenyl.

The abbreviations and acronyms have the following meaning.
EB: electron beam
EUV: extreme ultraviolet
Mw: weight average molecular weight
Mn: number average molecular weight
Mw/Mn: molecular weight distribution or dispersity
GPC: gel permeation chromatography
PEB: post-exposure bake
PAG: photoacid generator
LWR: line width roughness
CDU: critical dimension uniformity
Resist Composition The resist composition of the invention is defined as comprising a base polymer and a sulfonium salt or iodonium salt of a fluorobenzenesulfonic acid bonded to iodized benzoic acid. The sulfonium or iodonium salt is an acid generator capable of generating a fluorobenzenesulfonic acid bonded to iodized benzoic acid upon light exposure. In the resist composition, an acid generator capable of generating another sulfonic acid, imide acid or methide acid may be either added as a separate component or bound in the base polymer.

Ie;.5qWhen a resist composition containing the sulfonium salt of fluorobenzenesulfonic acid bonded to iodized benzoic acid in admixture with a sulfonium salt of weaker acid in the form of sulfonic or carboxylic acid is exposed to radiation, fluorobenzenesulfonic acid bonded to iodized benzoic acid and weaker acid in the form of sulfonic or carboxylic acid generate. Since the acid generator is not entirely decomposed, the undecomposed acid generator is present nearby. When the fluorobenzenesulfonic acid bonded to iodized benzoic acid co-exists with the sulfonium salt of weaker acid in the form of sulfonic or carboxylic acid, ion exchange takes place therebetween, whereby a sulfonium salt of fluorobenzenesulfonic acid bonded to iodized benzoic acid is created and a weaker acid in the form of sulfonic or carboxylic acid is released. This is because the salt of fluorobenzenesulfonic acid bonded to iodized benzoic acid having a higher acid strength is more stable. In contrast, when a sulfonium salt of fluorobenzenesulfonic acid bonded to iodized benzoic acid co-exists with a weaker acid in the form of sulfonic or carboxylic acid, no ion exchange takes place. The ion exchange reaction according to the acid strength series occurs not only with sulfonium salts, but also similarly with iodonium salts. When combined with an acid generator of fluorosulfonic acid, a sulfonium or iodonium salt of weak acid functions as a quencher. Since iodine is highly absorptive to EUV of wavelength 13.5 nm, it generates secondary electrons upon EUV exposure. The energy of secondary electrons is transferred to the acid generator to promote its decomposition, contributing to a higher sensitivity. The effect becomes significant when the number of iodine substitution is 3 or more.

For the LWR improving purpose, it is effective to prevent a polymer and/or acid generator from agglomeration. Effective means for preventing agglomeration of a polymer is by reducing the difference between hydrophobic and hydrophilic properties, by lowering the glass transition temperature (Tg) thereof, or by reducing the molecular weight thereof. Specifically, it is effective to reduce the polarity difference between a hydrophobic acid labile group and a hydrophilic adhesive group or to lower the Tg by using a compact adhesive group like monocyclic lactone. One effective means for preventing agglomeration of an acid generator is by introducing a substituent into the triphenylsulfonium cation. In particular, with respect to a methacrylate polymer containing an alicyclic protective group and a lactone adhesive group for ArF lithography, a triphenylsulfonium composed solely of aromatic groups has a heterogeneous structure and low compatibility. As the substituent to be introduced into triphenylsulfonium, an alicyclic group or lactone similar to those used in the base polymer is regarded adequate.

When lactone is introduced into a sulfonium salt which is hydrophilic, the resulting sulfonium salt becomes too hydrophilic and thus less compatible with a polymer, with a likelihood that the sulfonium salt will agglomerate. When a hydrophobic alkyl group is introduced, the sulfonium salt may be uniformly dispersed within the resist film. WO 2011/048919 discloses the technique for improving LWR by introducing an alkyl group into a sulfonium salt capable of generating an α-fluorinated sulfone imide acid.

The sulfonium or iodonium salt of fluorobenzenesulfonic acid bonded to iodized benzoic acid having iodine of a high atomic weight introduced into its anion moiety is less diffusible, highly compatible with a polymer, and thus highly dispersible. There are obtained advantages of low LWR and improved CDU.

The sulfonium or iodonium salt of fluorobenzenesulfonic acid bonded to iodized benzoic acid exerts LWR reducing and CDU improving effects, which may stand good either in positive and negative tone pattern formation by alkaline aqueous solution development or in negative tone pattern formation by organic solvent development.

Acid Generator

The acid generator in the inventive resist composition contains a sulfonium salt having the formula (A-1) or an iodonium salt having the formula (A-2).

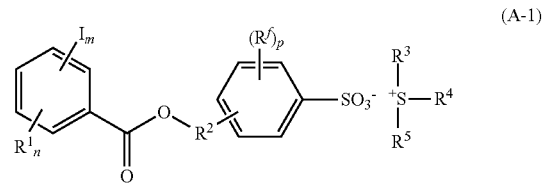

(A-1)

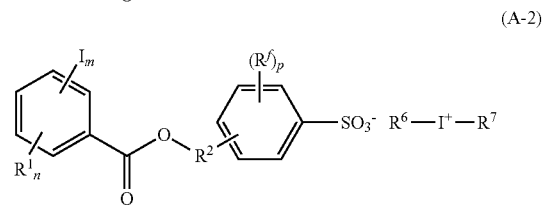

(A-2)

Herein $R^1$ is a hydroxyl group, carboxyl group, fluorine, chlorine, bromine, amino group, or a straight, branched or cyclic $C_1$-$C_{20}$ alkyl, $C_1$-$C_{20}$ alkoxy, $C_2$-$C_{20}$ alkoxycarbonyl or $C_2$-$C_{20}$ acyloxy group which may contain fluorine, chlorine, bromine, hydroxyl, amino or alkoxy moiety, or —$NR^9$—C(=O)—$R^{10}$ or —$NR^9$—C(=O)—O—$R^{10}$, wherein $R^9$ is hydrogen, or a straight, branched or cyclic $C_1$-$C_6$ alkyl group, $R^{10}$ is a straight, branched or cyclic $C_1$-$C_{16}$ alkyl, straight, branched or cyclic $C_2$-$C_{16}$ alkenyl, or $C_6$-$C_{12}$ aryl group which may contain halogen, hydroxyl, alkoxy, acyl or acyloxy moiety. $R^2$ is a single bond, or a divalent $C_1$-$C_{20}$ linking group which may contain oxygen, sulfur or nitrogen. $R^f$ is fluorine or trifluoromethyl. $R^3$, $R^4$ and $R^5$ are each independently fluorine, chlorine, bromine, iodine, $C_1$-$C_{12}$ straight, branched or cyclic alkyl group, $C_2$-$C_{12}$ straight, branched or cyclic alkenyl group, $C_6$-$C_{20}$ aryl group, or $C_7$-$C_{12}$ aralkyl or aryloxyalkyl group, at least one hydrogen (i.e., one or more or even all hydrogen atoms) in the foregoing groups may be substituted by hydroxyl, carboxyl, halogen, oxo, cyano, amide, nitro, sultone, sulfone, or sulfonium salt-containing moiety, or at least one carbon (i.e., one or more carbon atoms) in the foregoing groups may be substituted by an ether, ester, carbonyl, carbonate or sulfonate moiety, or $R^3$ and $R^4$ may bond together to form a ring with the sulfur atom to which they are attached. $R^6$ and $R^7$ are each independently trifluoromethyl, a $C_6$-$C_{10}$ aryl group, $C_2$-$C_6$ alkenyl group, or $C_2$-$C_6$ alkynyl group, at least one hydrogen (i.e., one or more or even all hydrogen atoms) in the foregoing groups may be substituted by a halogen, trifluoromethyl, $C_1$-$C_{10}$ straight, branched or cyclic alkyl or alkoxy, hydroxyl, carboxyl, alkoxycarbonyl, nitro or cyano moiety. The subscript m is an integer of 1 to 5, n is an integer of 0 to 3, and p is an integer of 1 to 4.

Examples of the cation moiety in the sulfonium salt having formula (A-1) are given below, but not limited thereto.

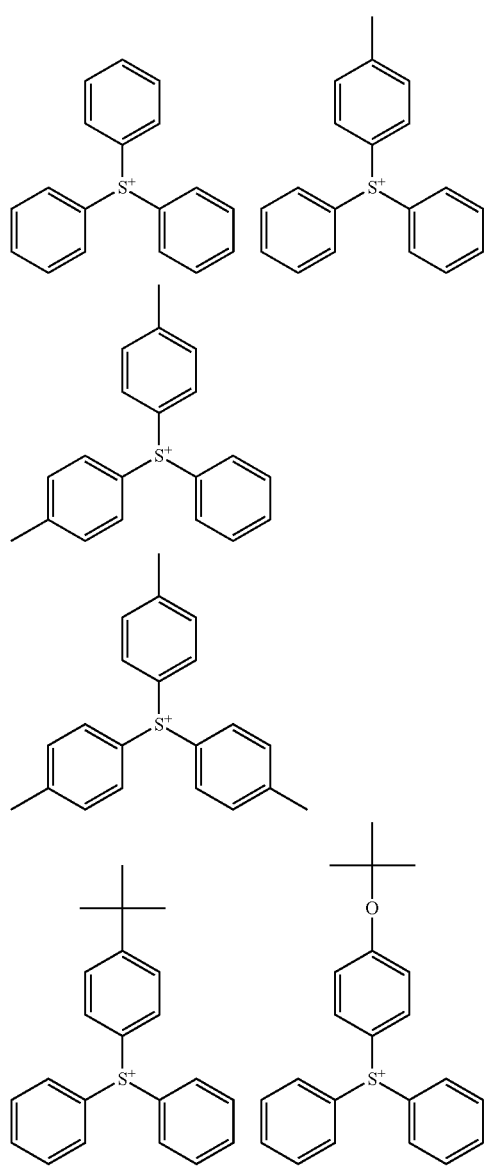

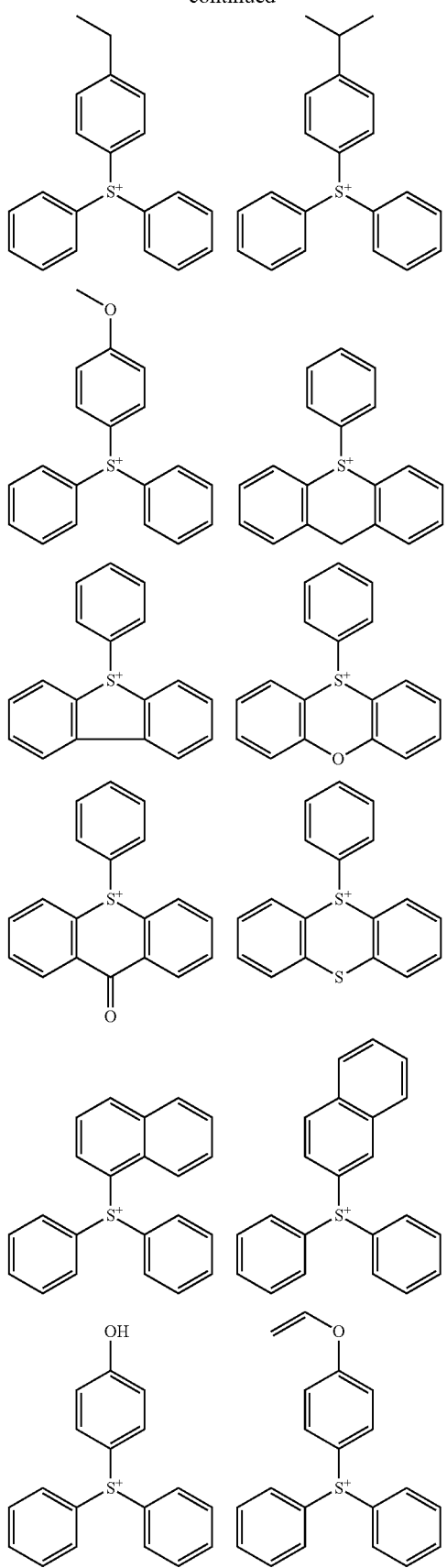

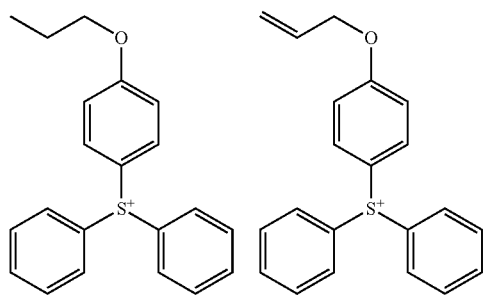
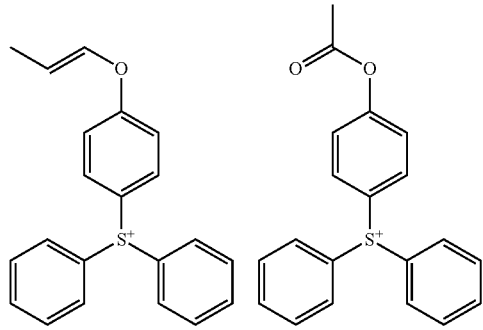
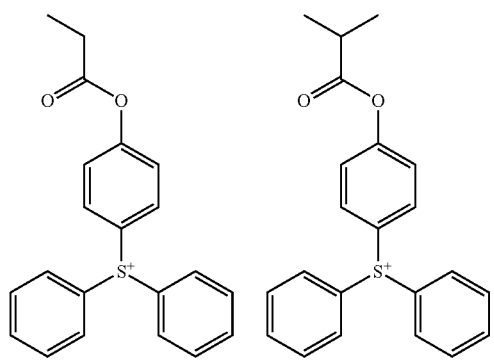
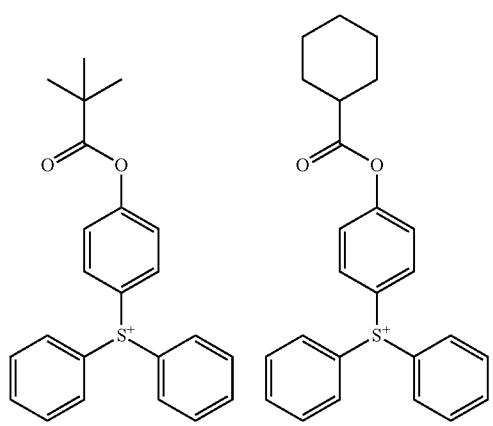
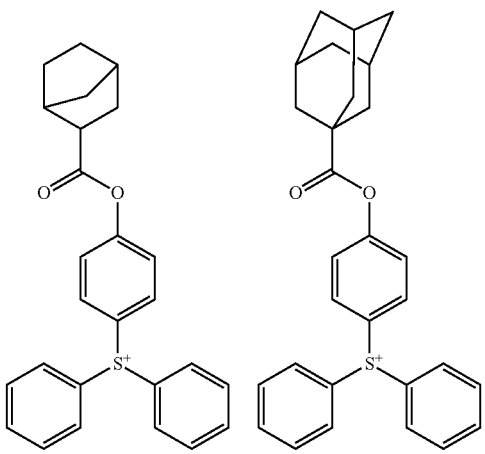
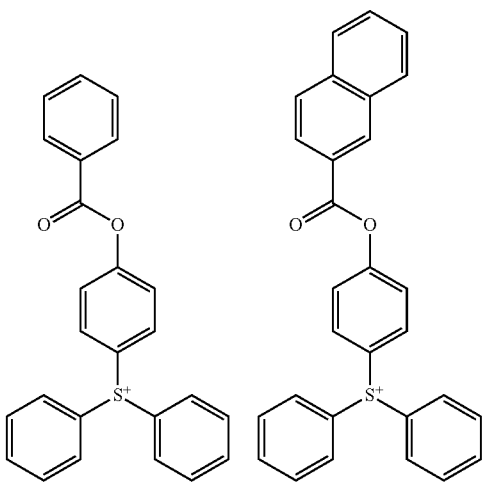
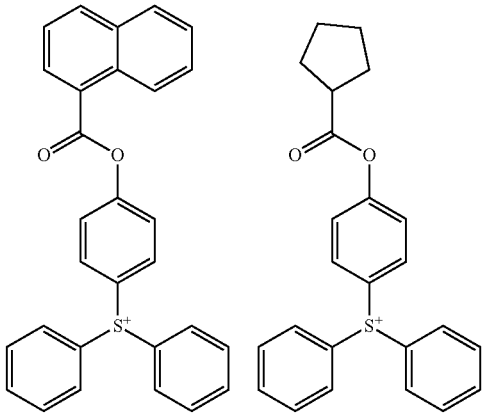

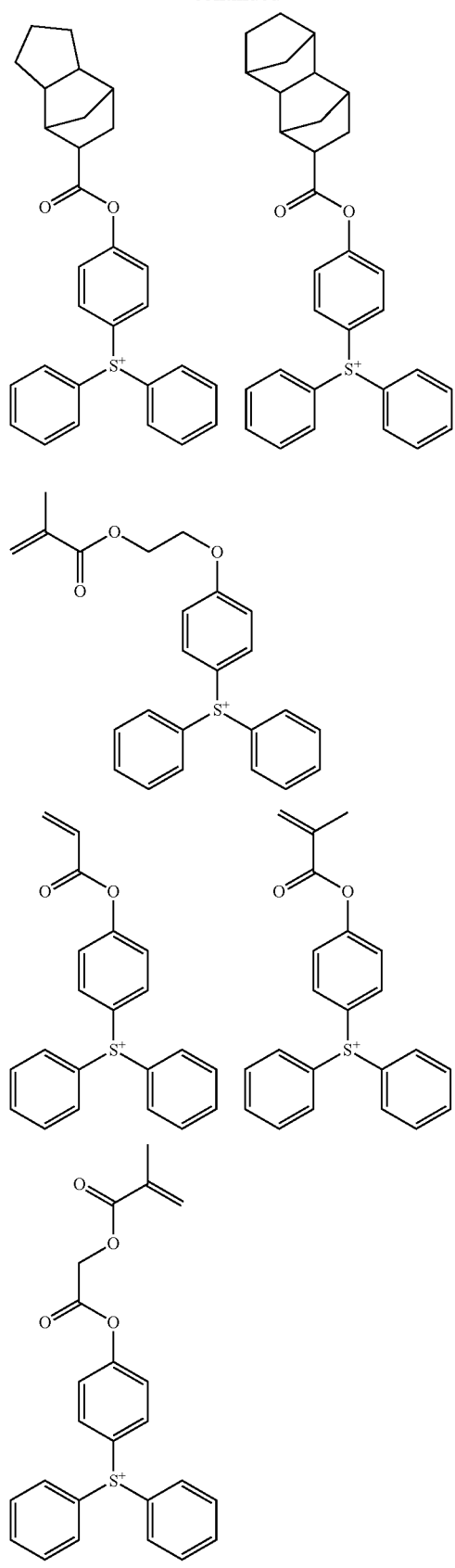
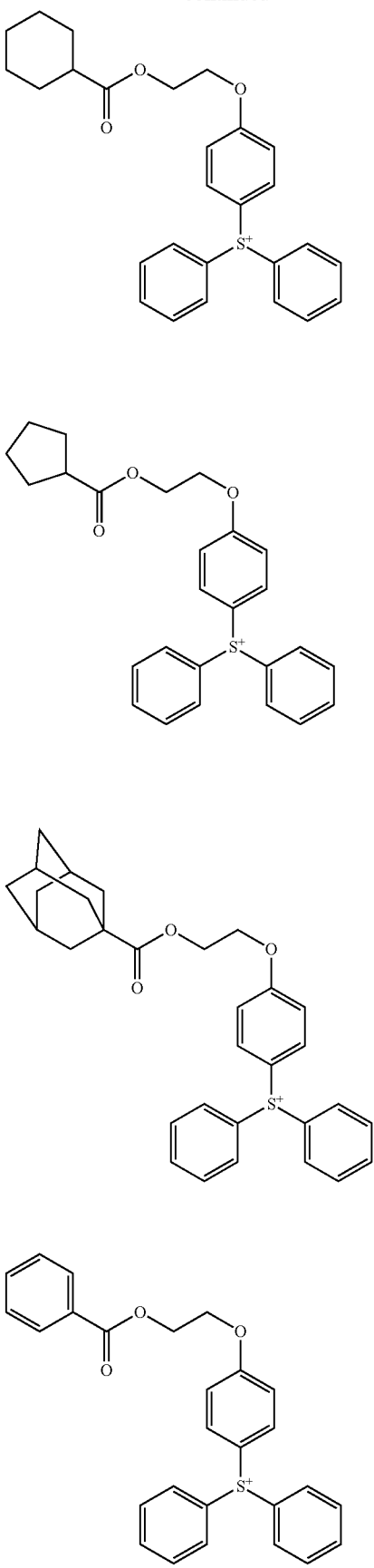

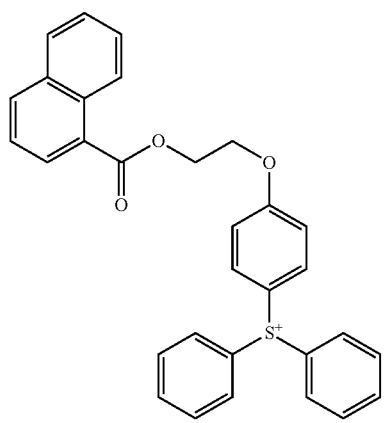
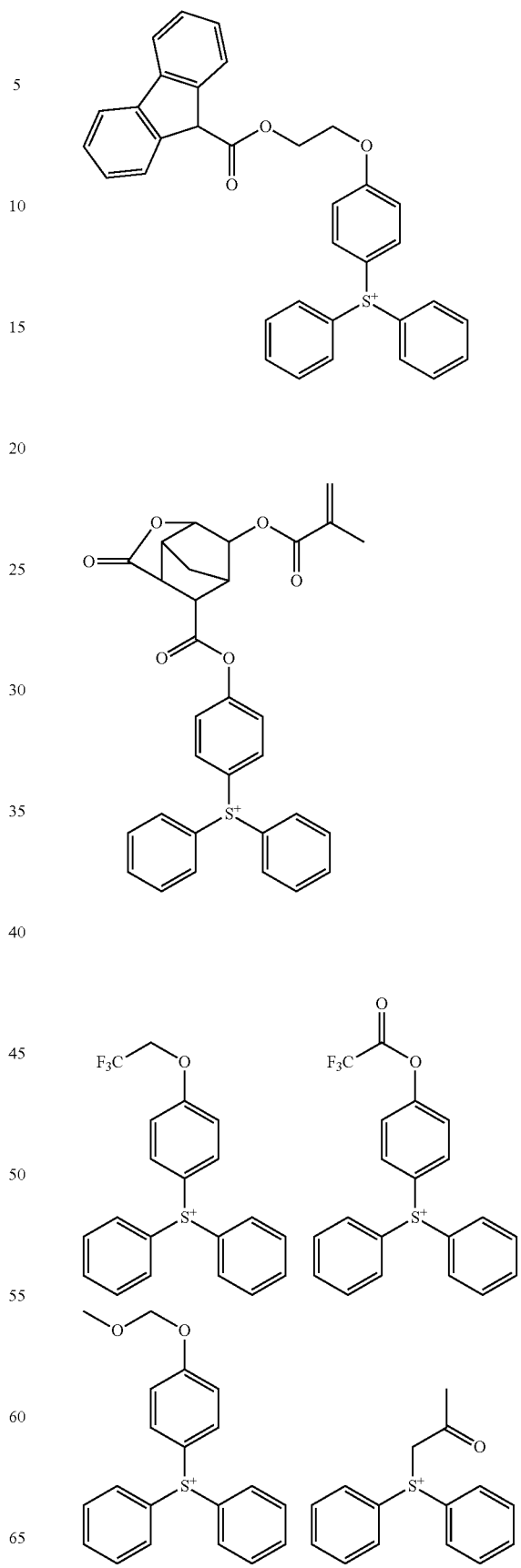

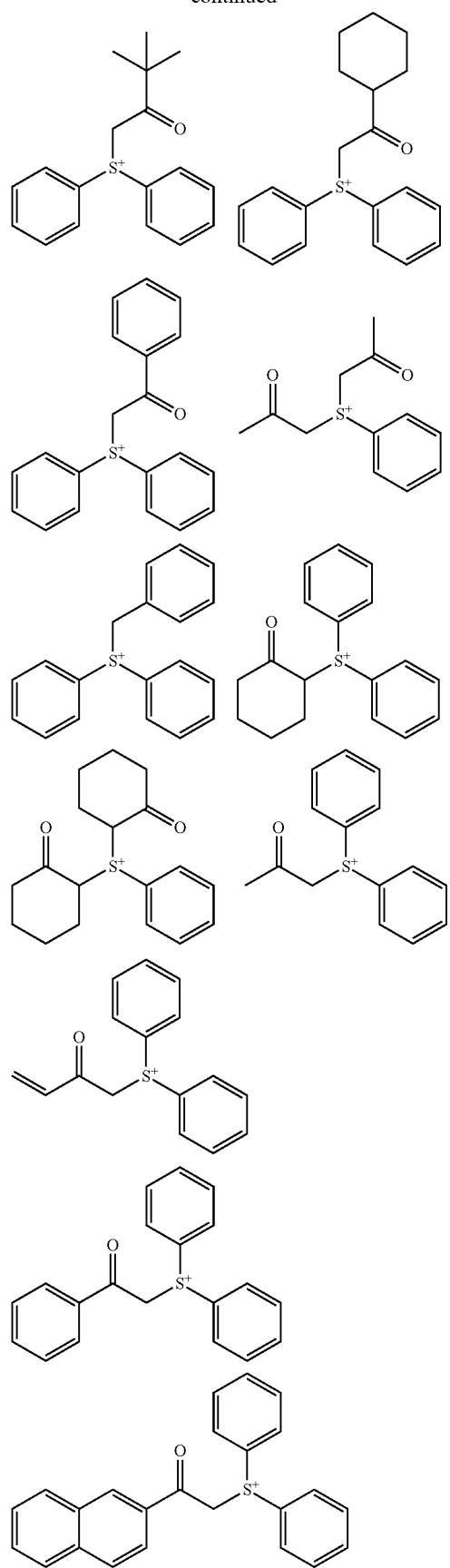
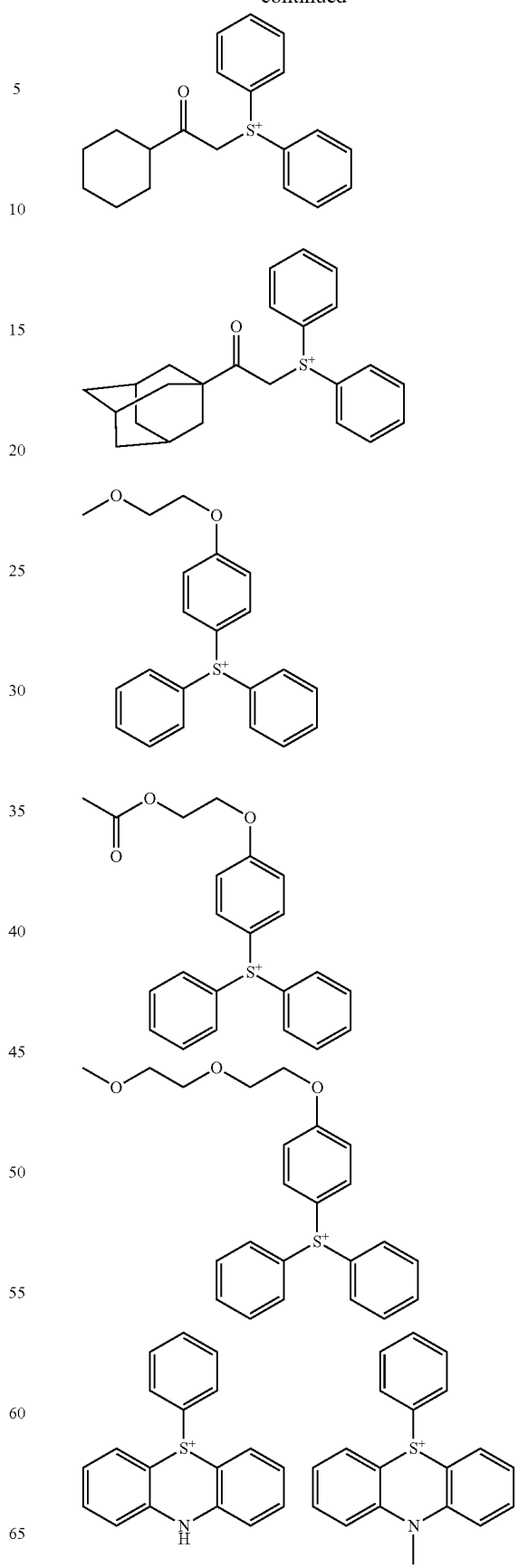

-continued
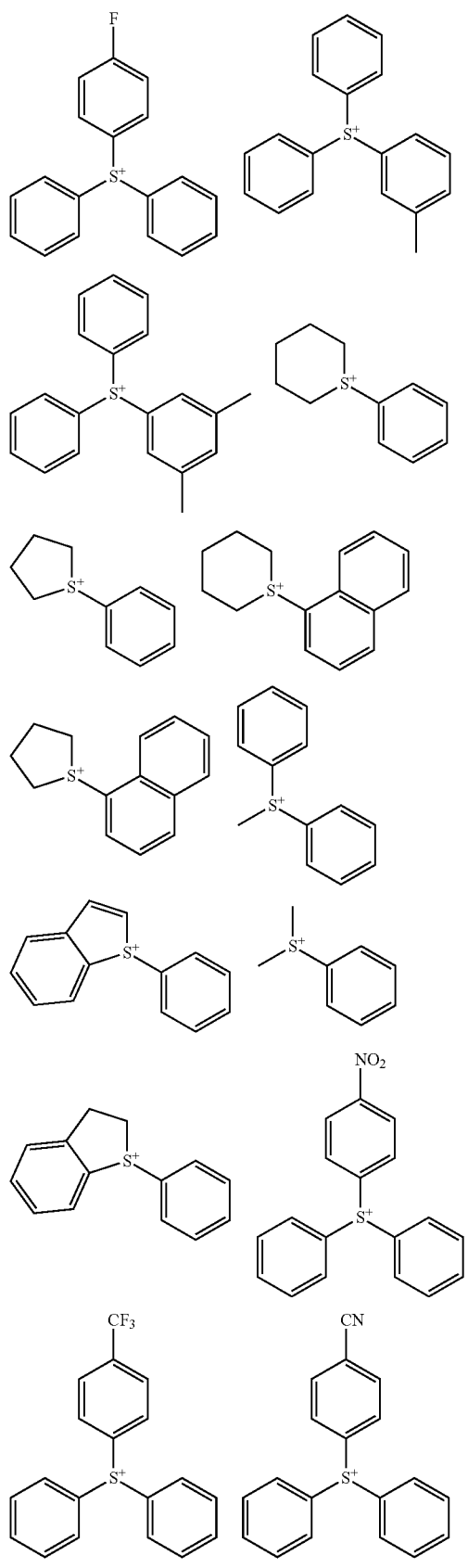
-continued
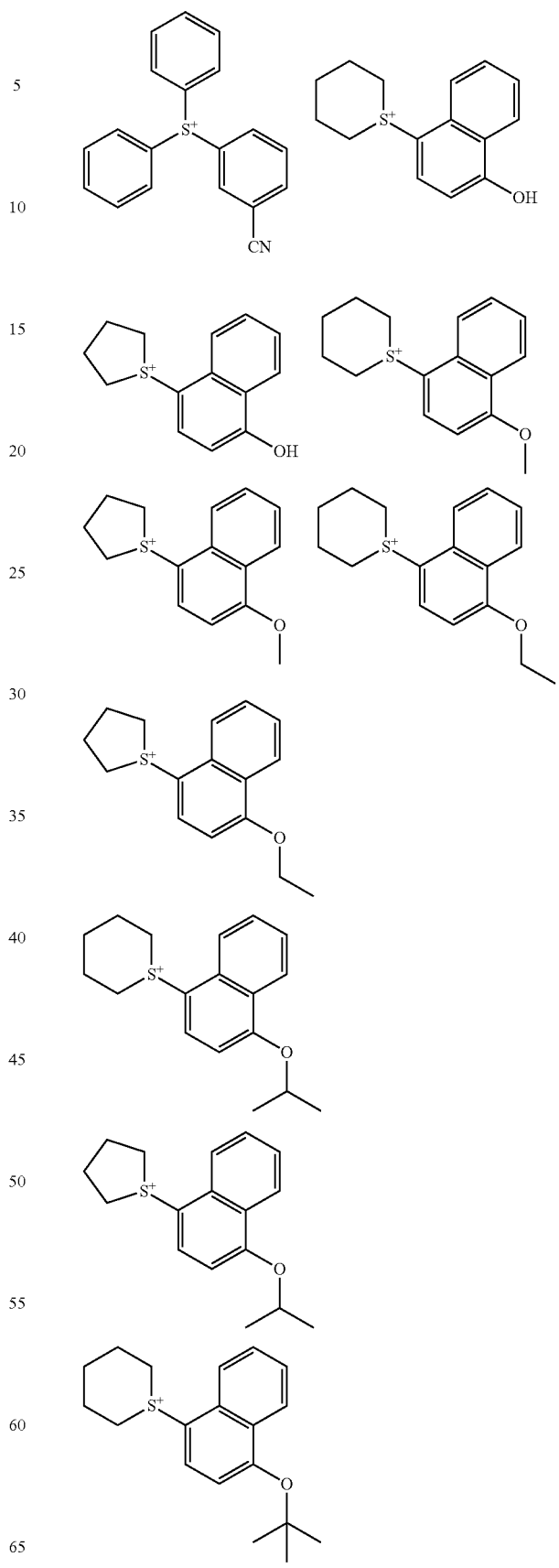

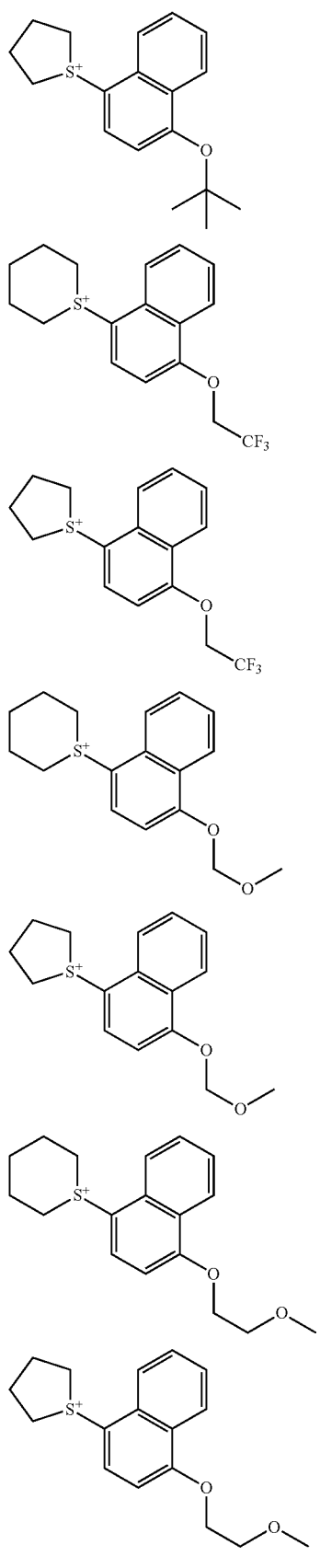
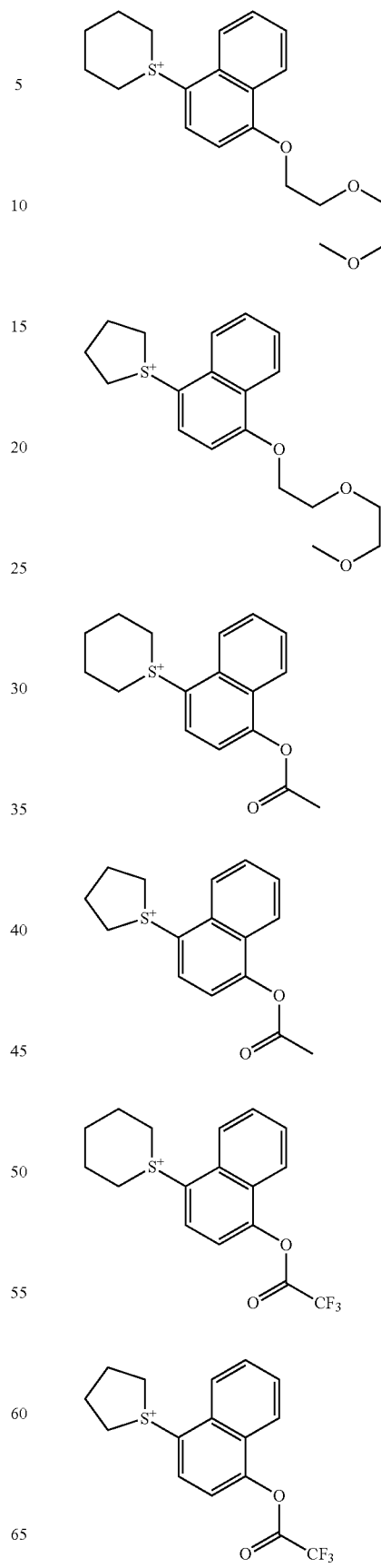

21
-continued
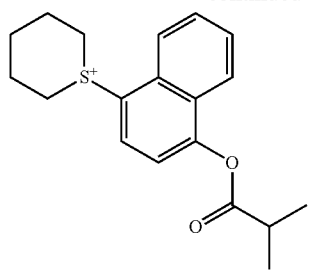
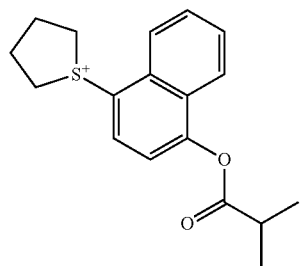
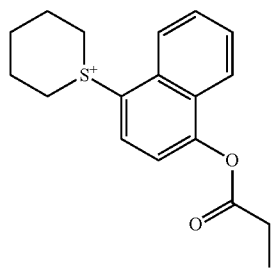
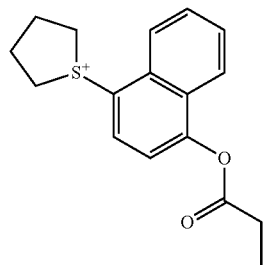
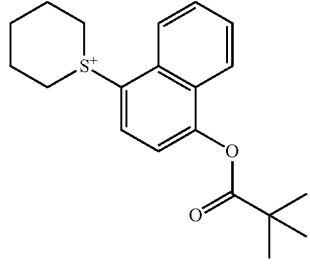
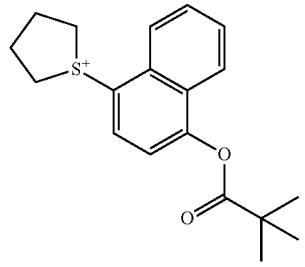
22
-continued
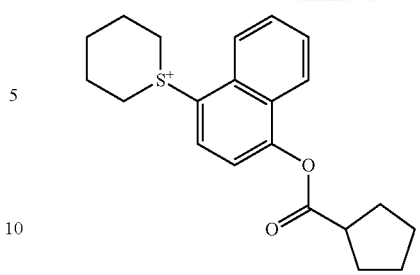
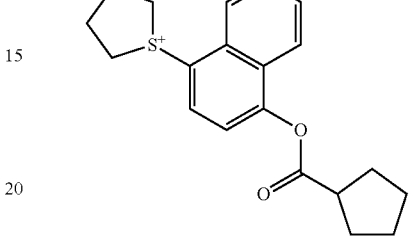
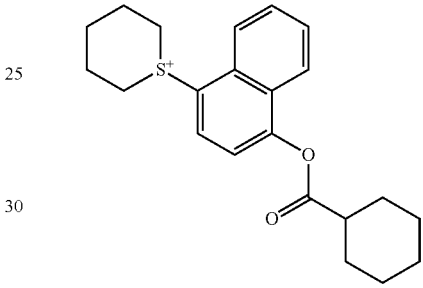
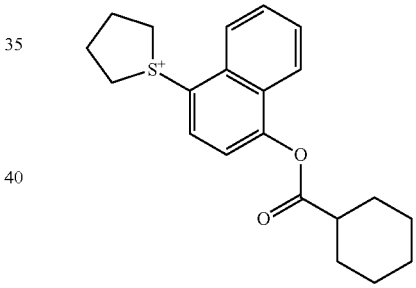
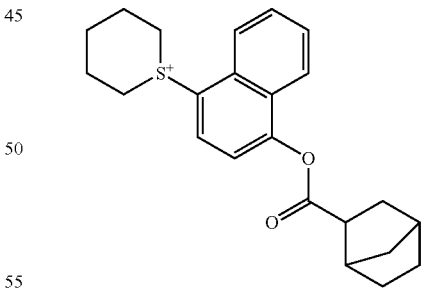
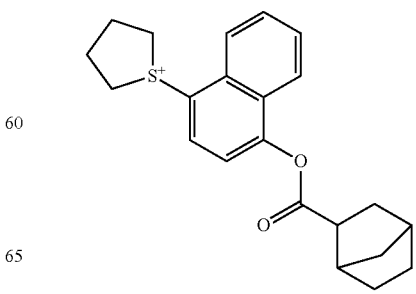

23
-continued
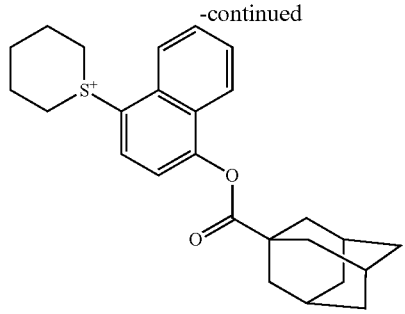
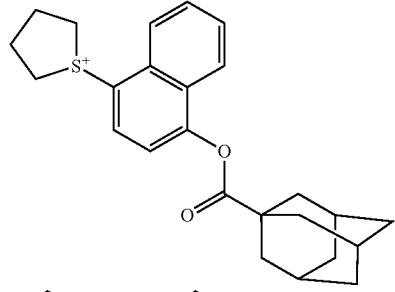
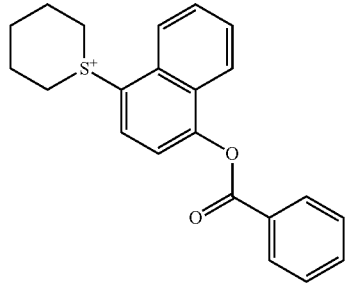
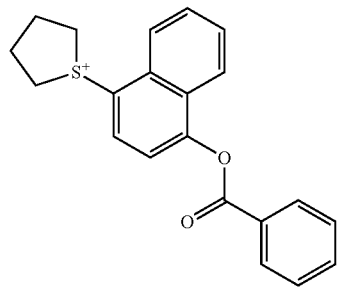
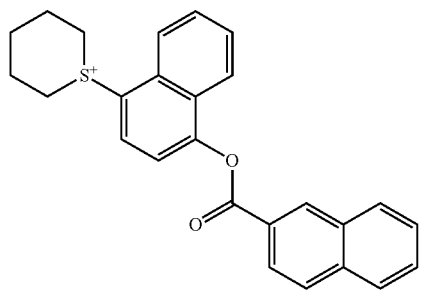
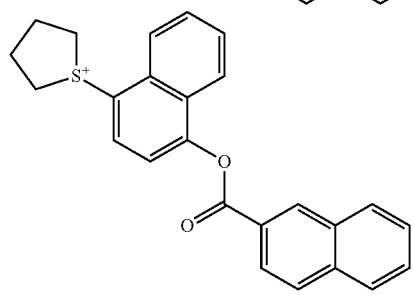
24
-continued
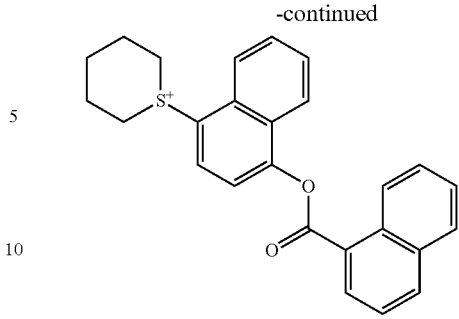
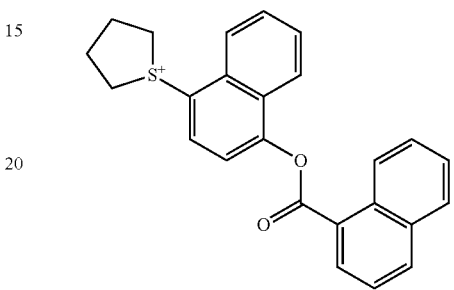
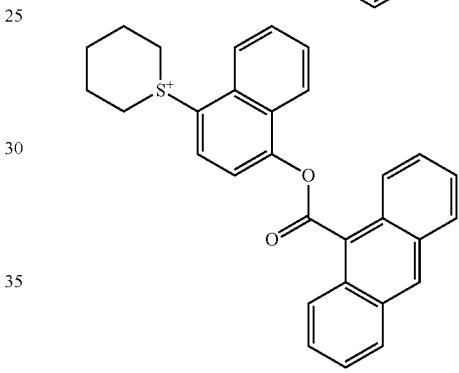
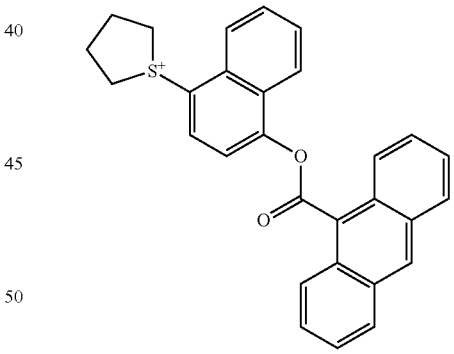
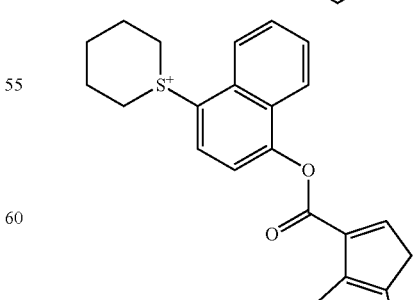

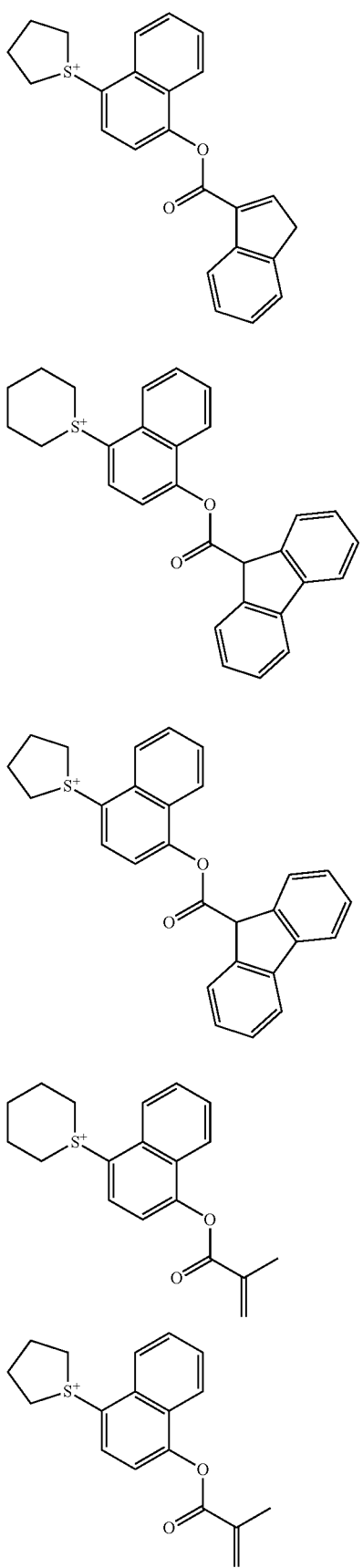
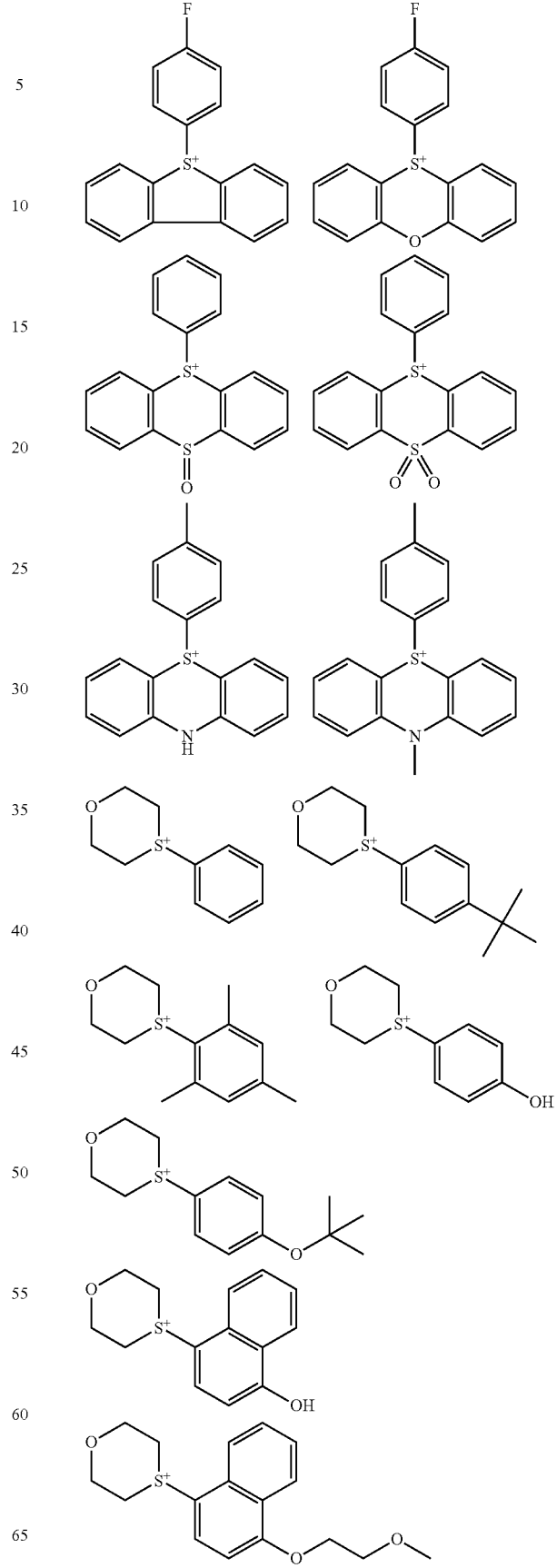

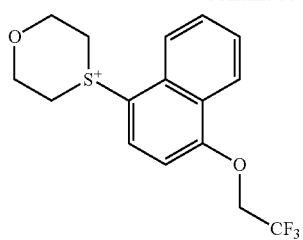
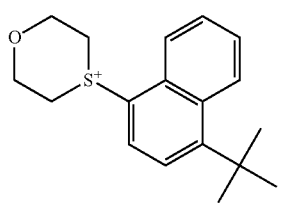
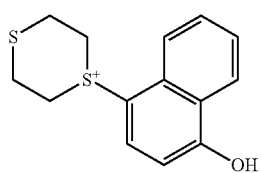
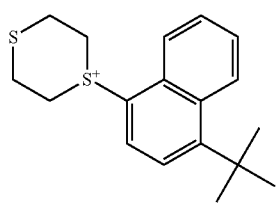
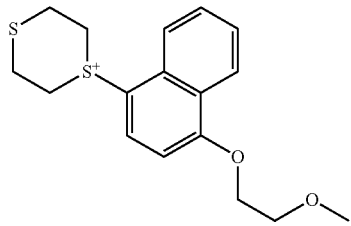
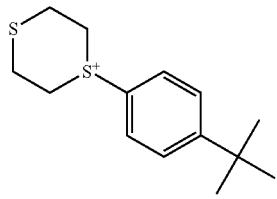
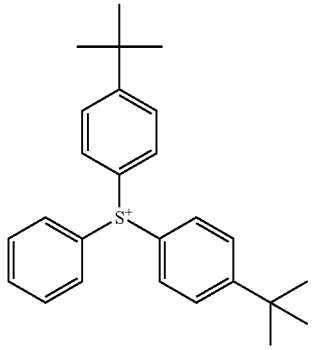
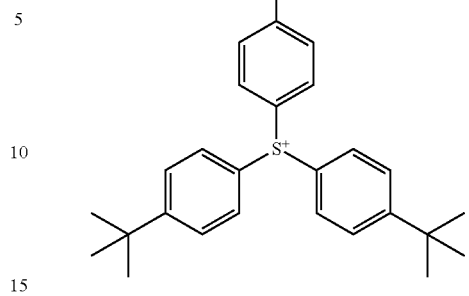
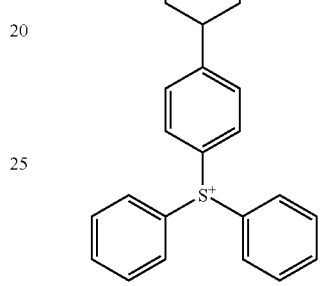
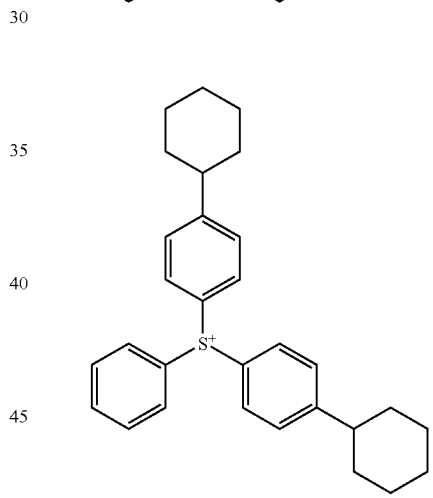
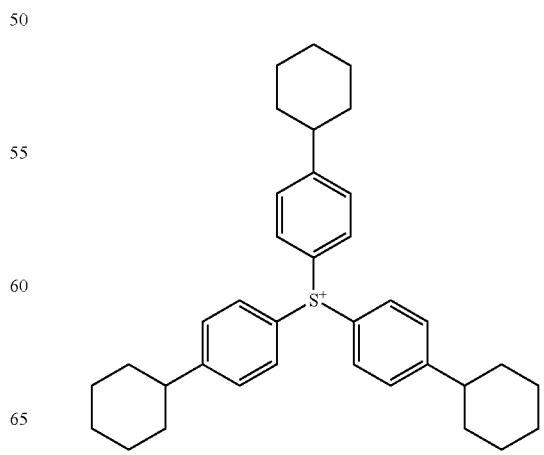

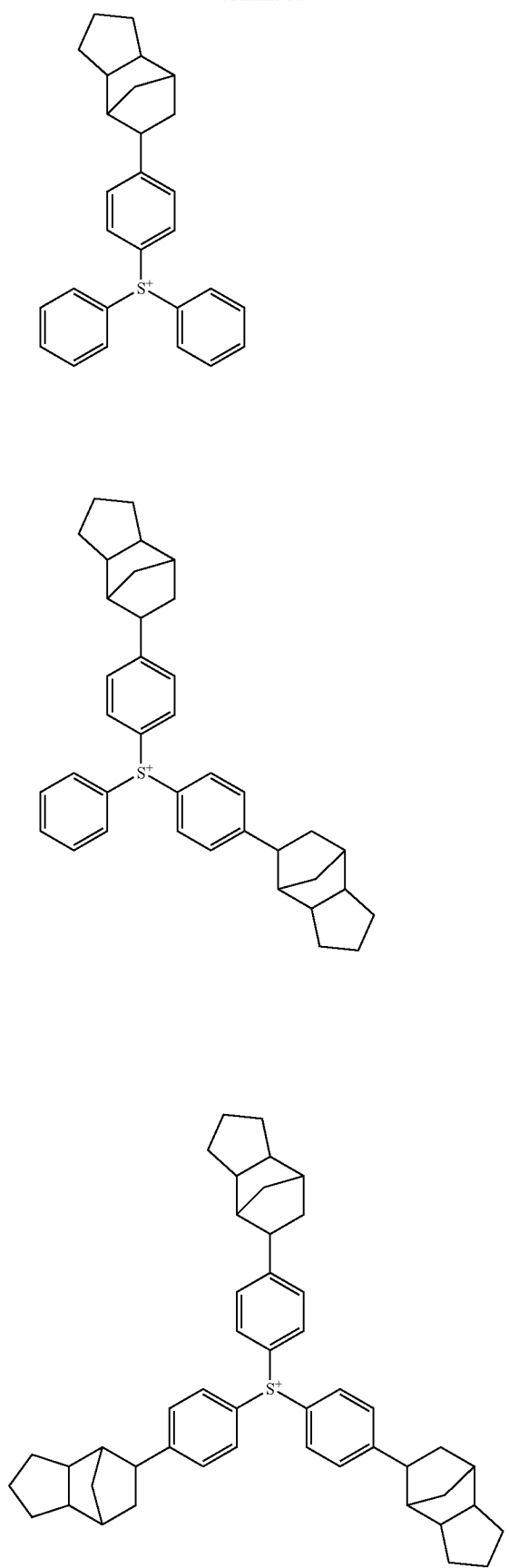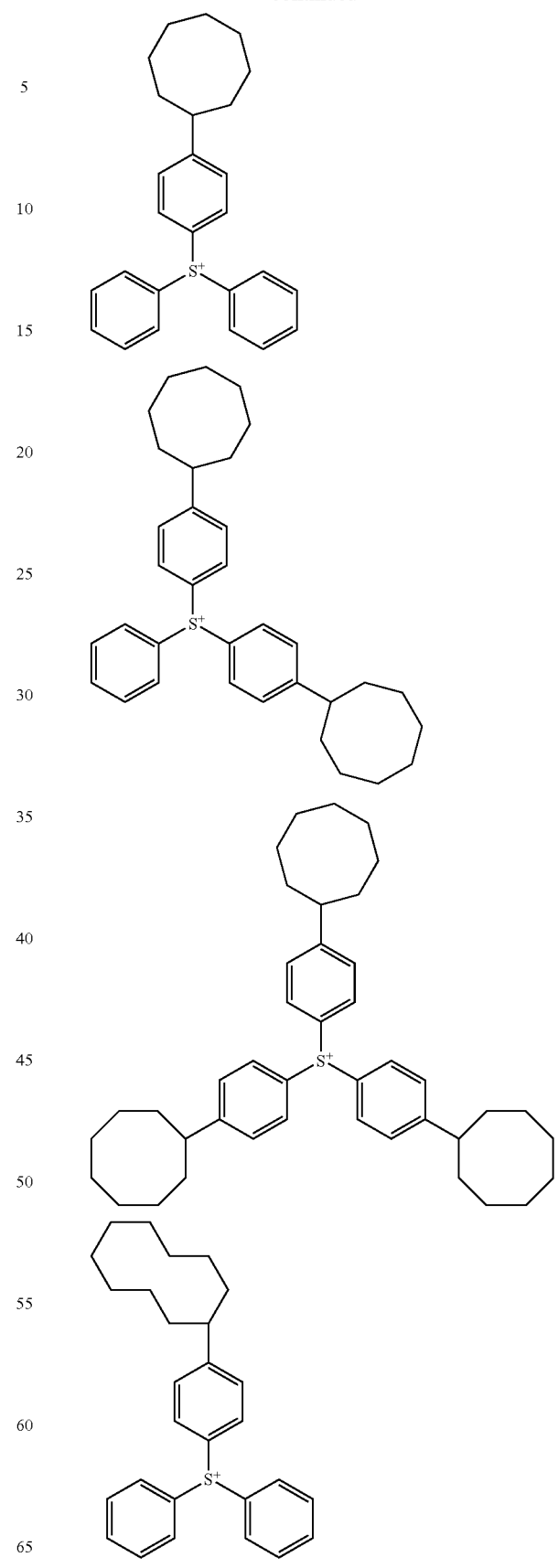

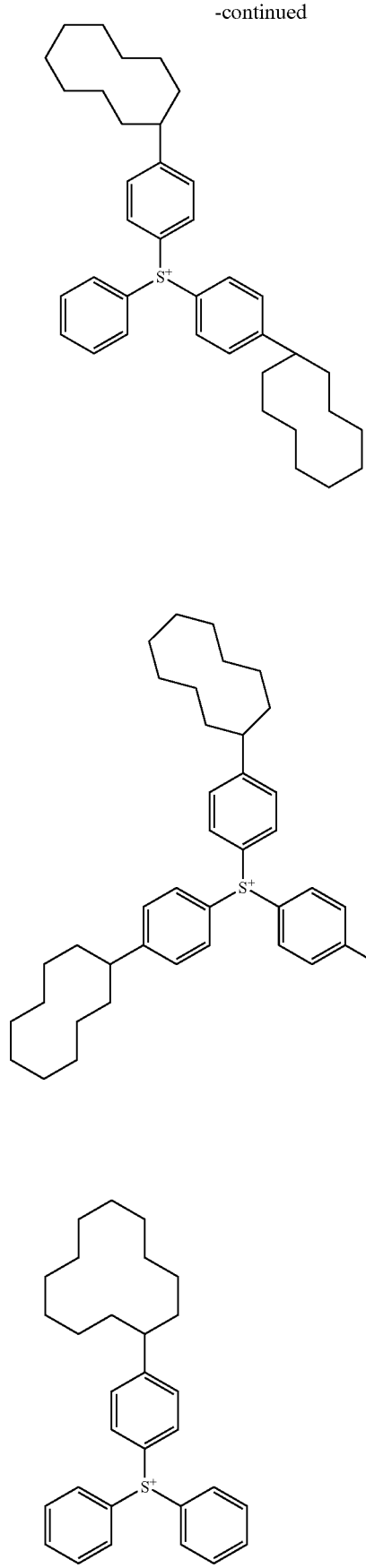
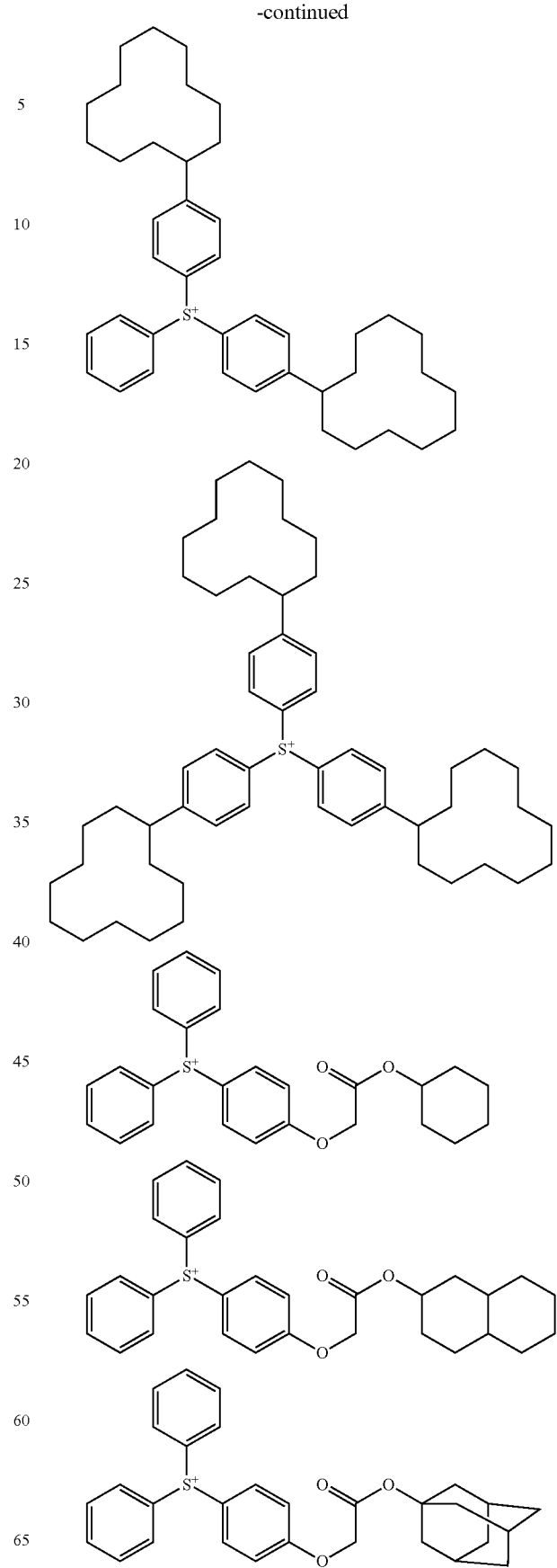

33
-continued
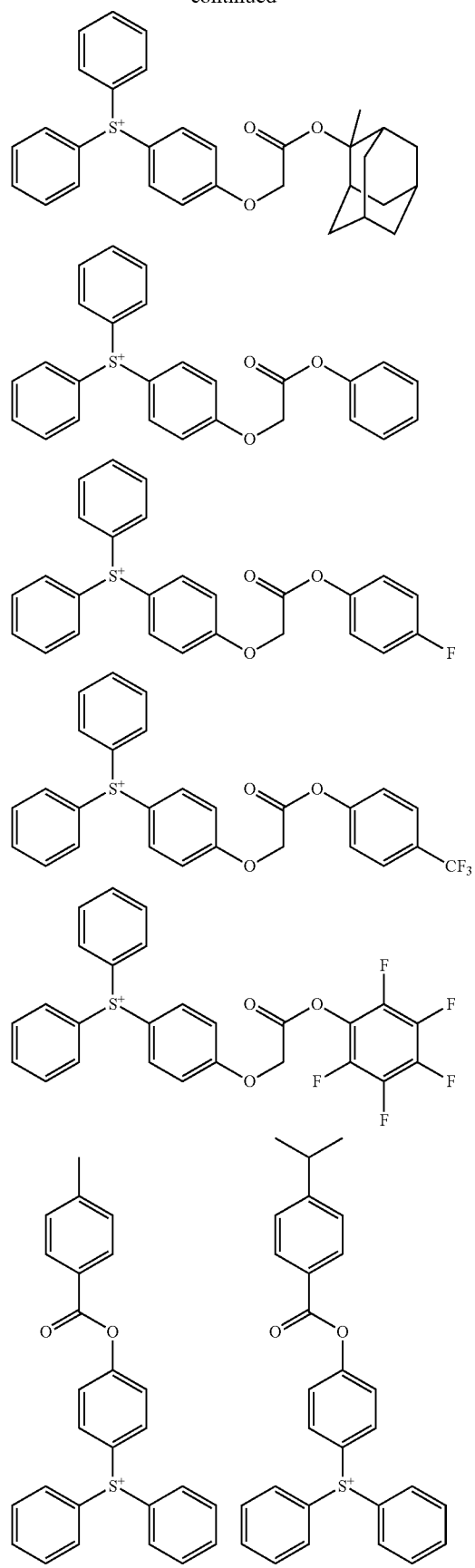
34
-continued
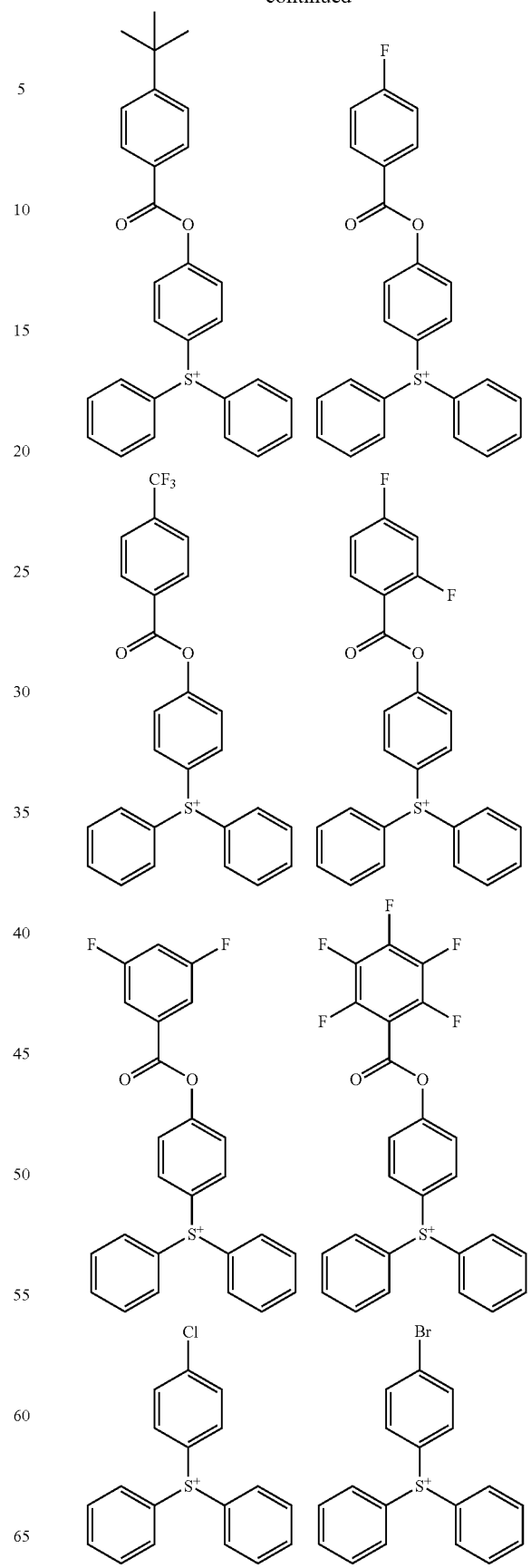

-continued
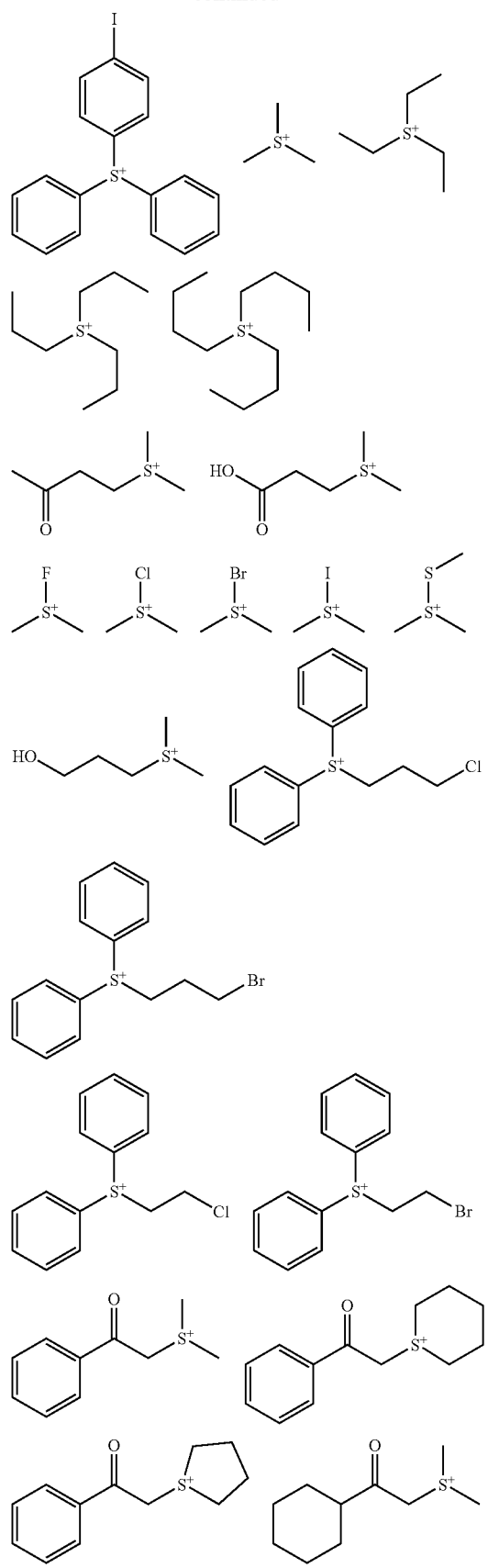
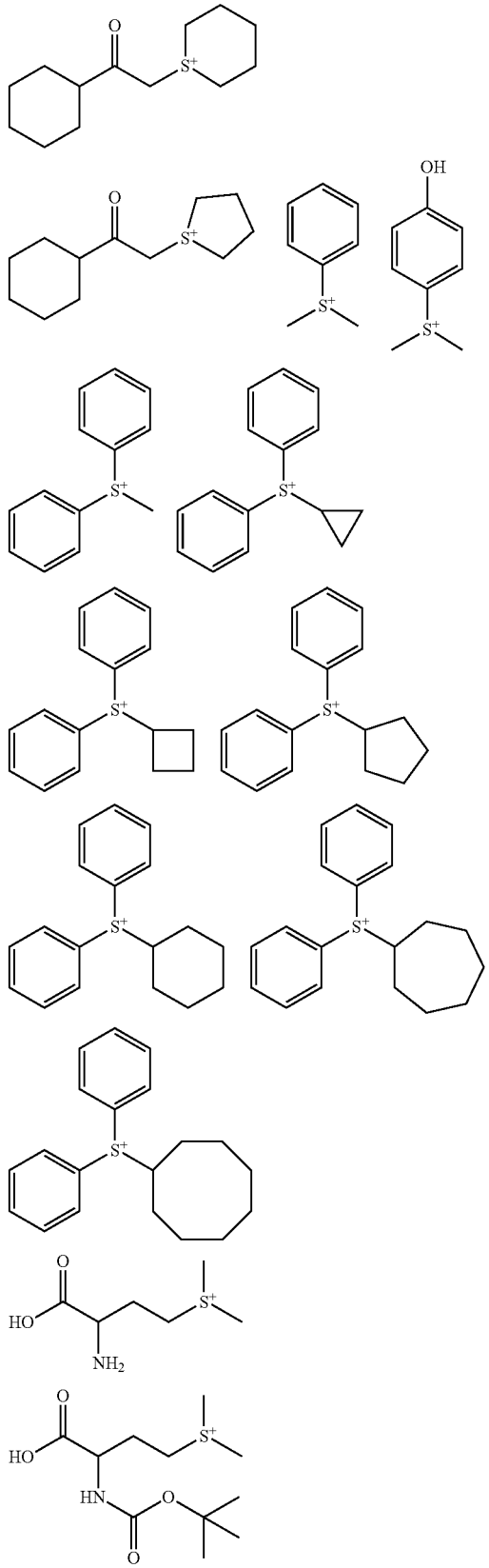
Examples of the cation moiety in the iodonium salt having formula (A-2) are given below, but not limited thereto.

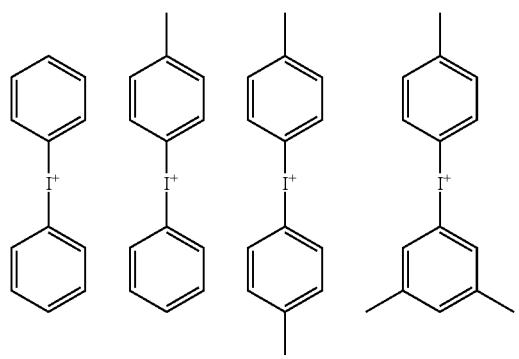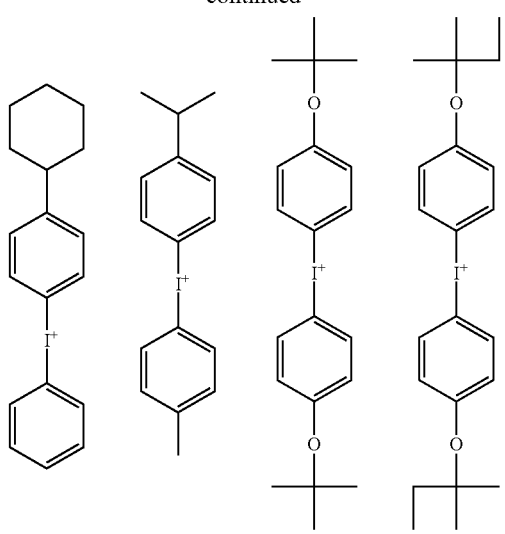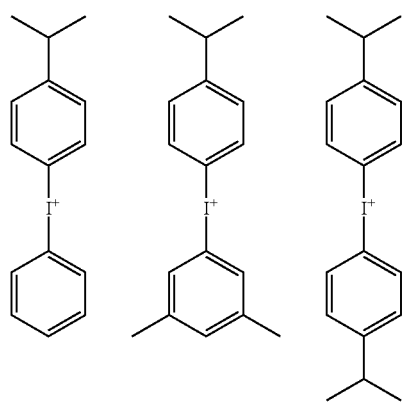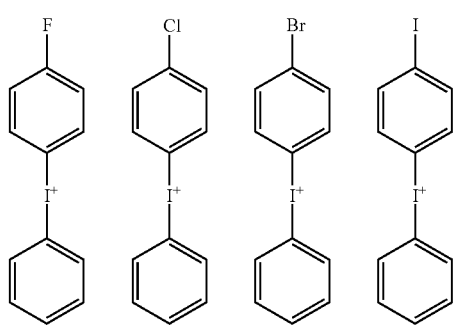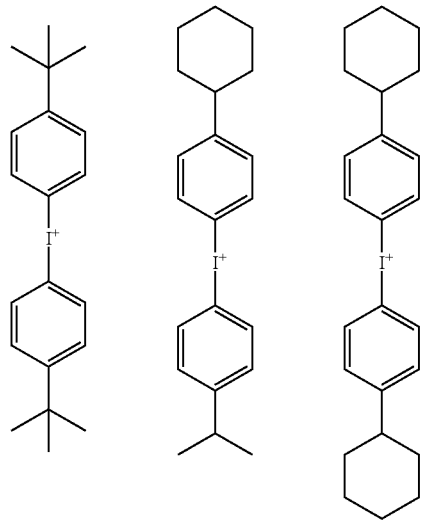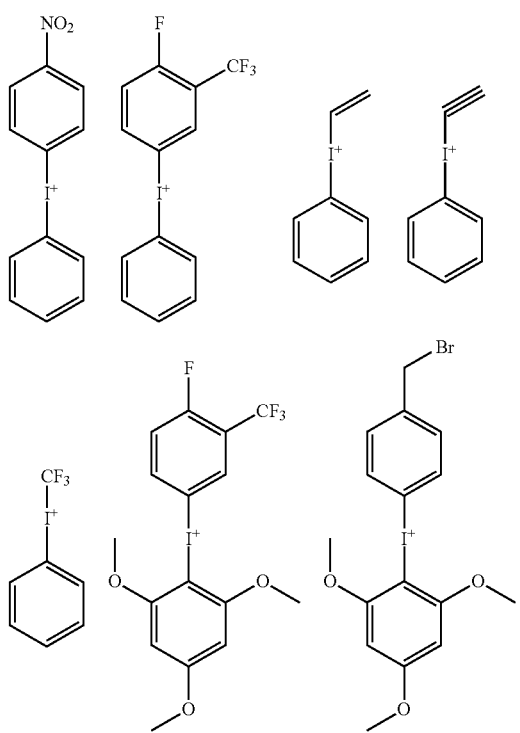

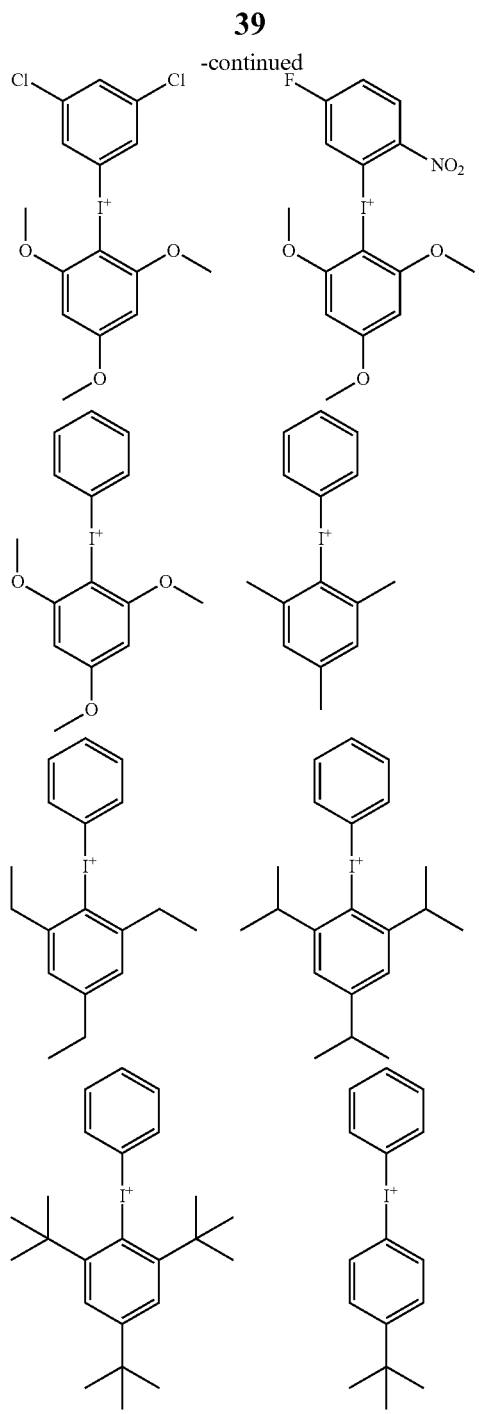
Examples of the anion moiety in the sulfonium salt having formula (A-1) and the iodonium salt having formula (A-2) are given below, but not limited thereto.
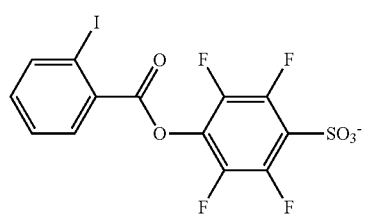
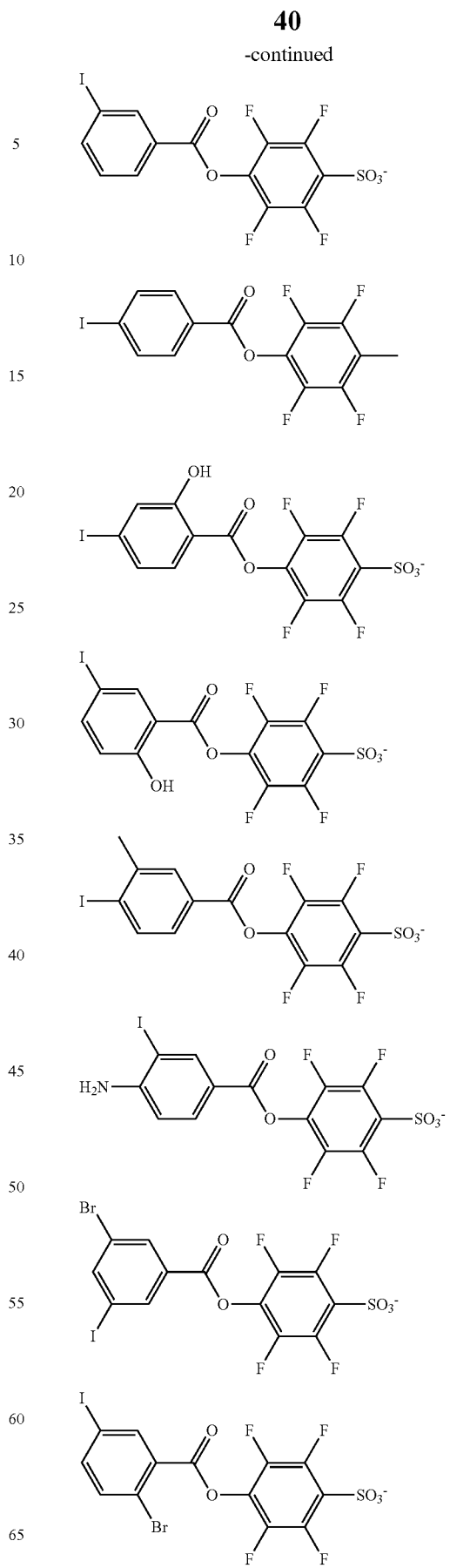

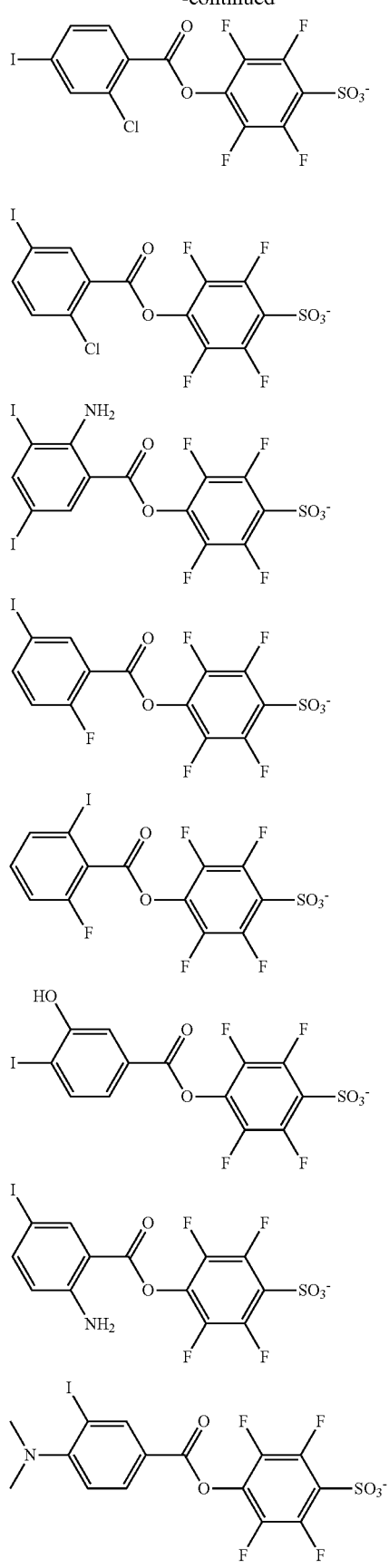
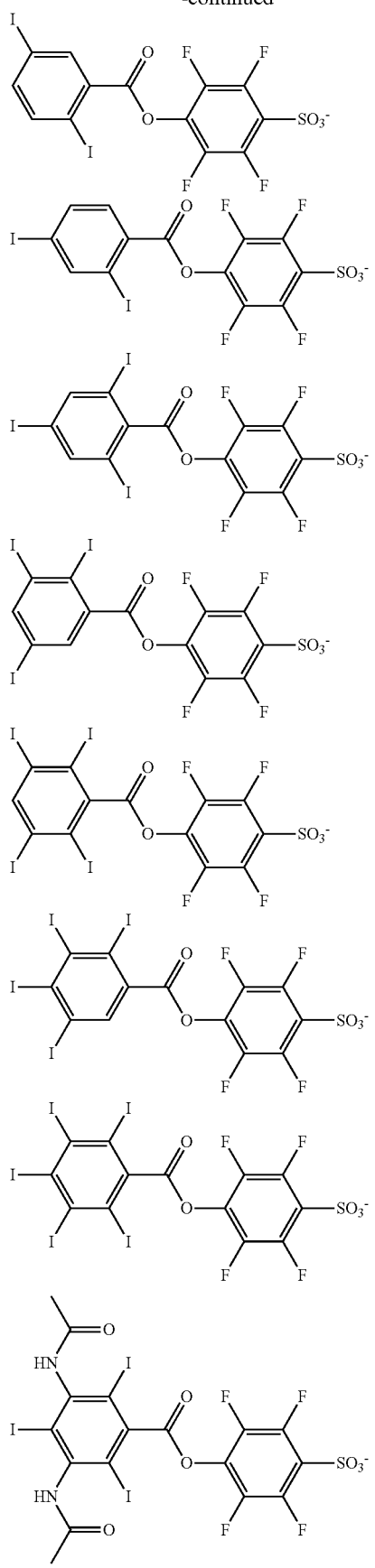

43
-continued
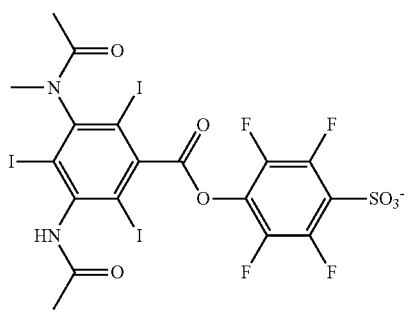
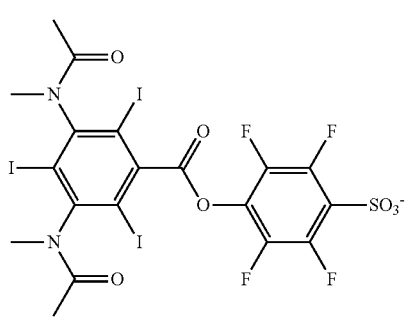
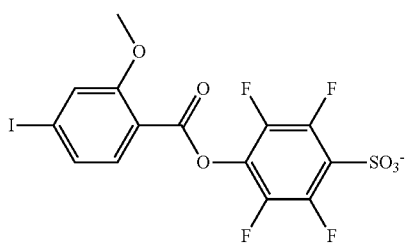
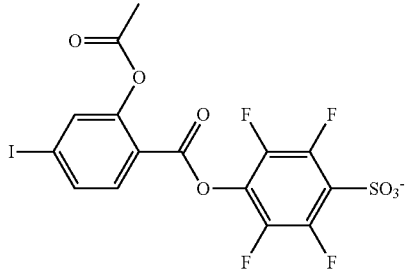
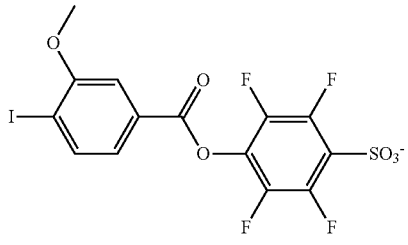
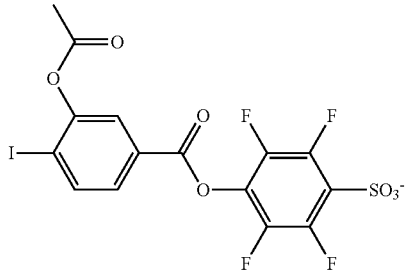
44
-continued
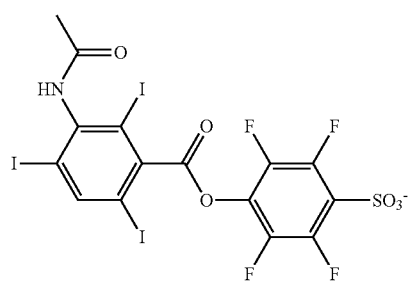
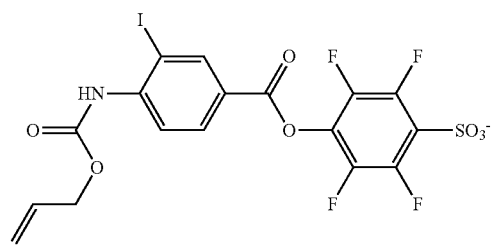
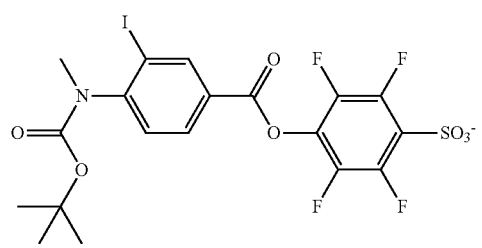
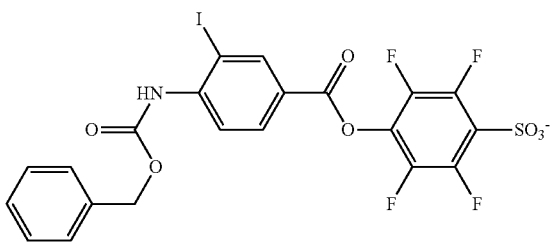
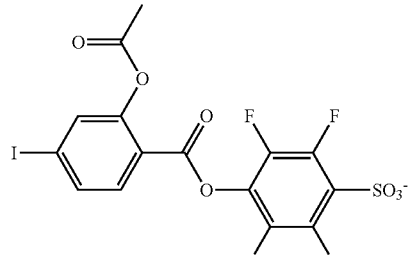
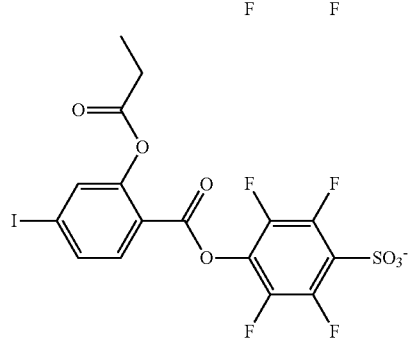

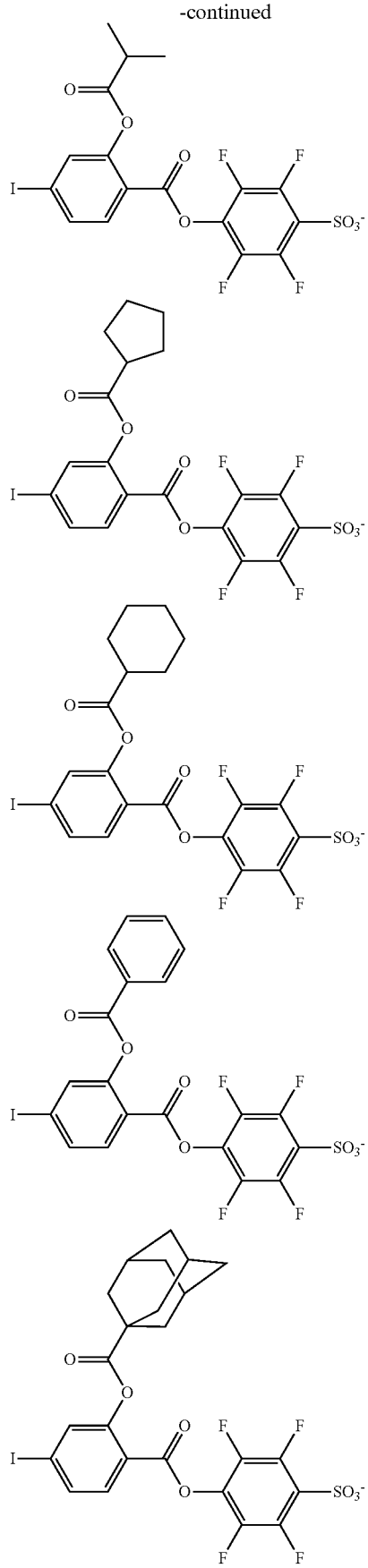
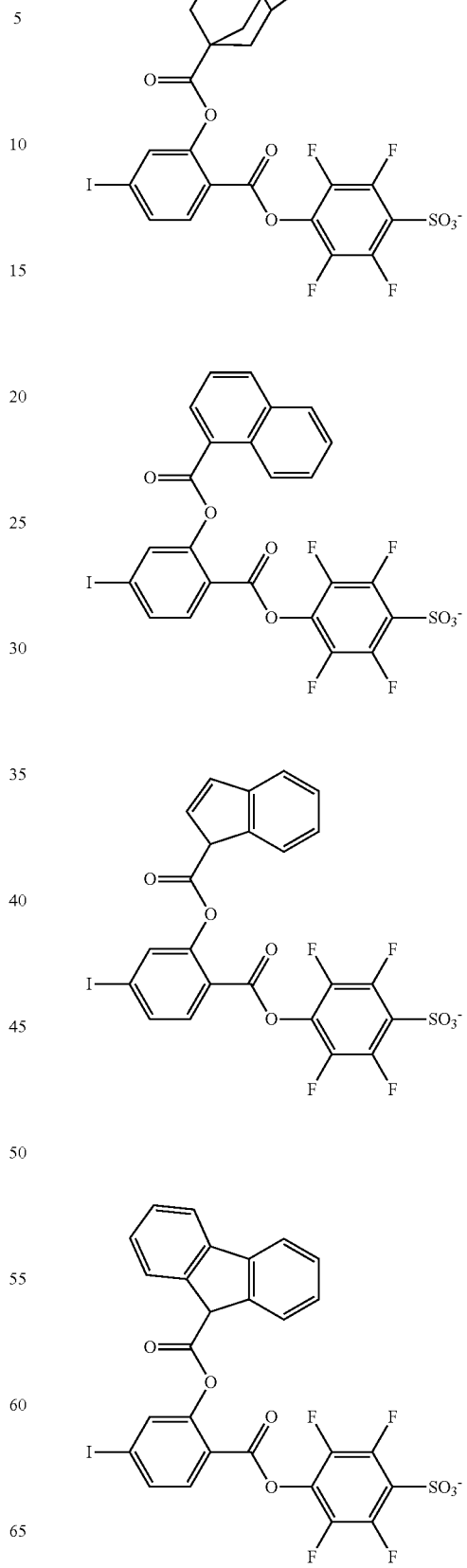

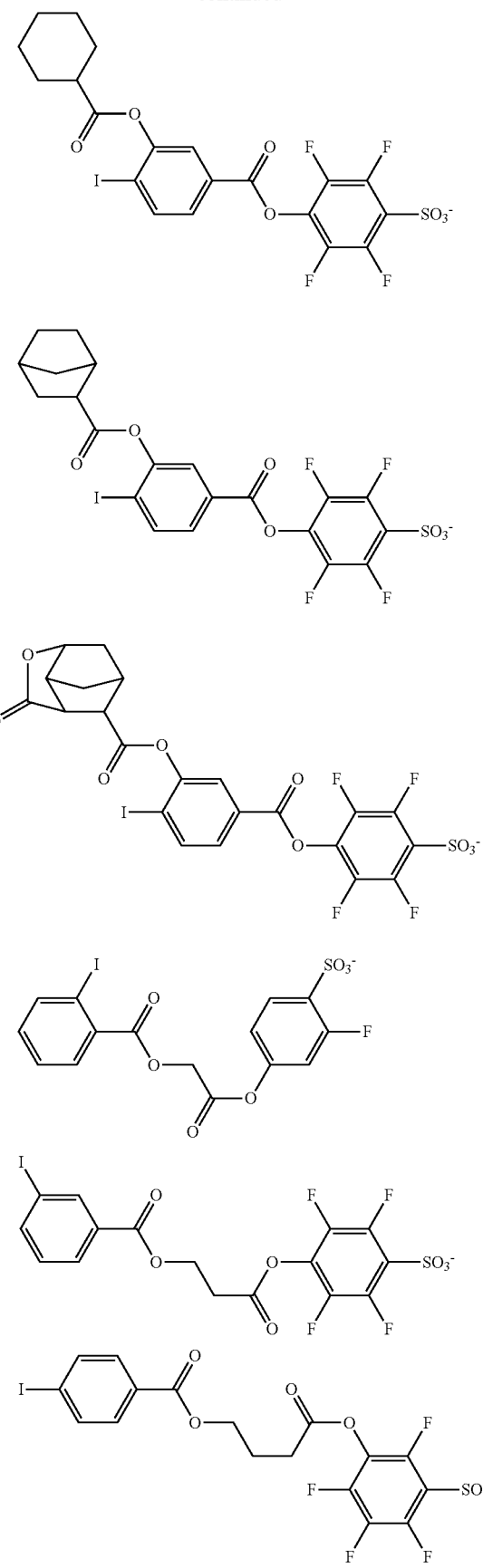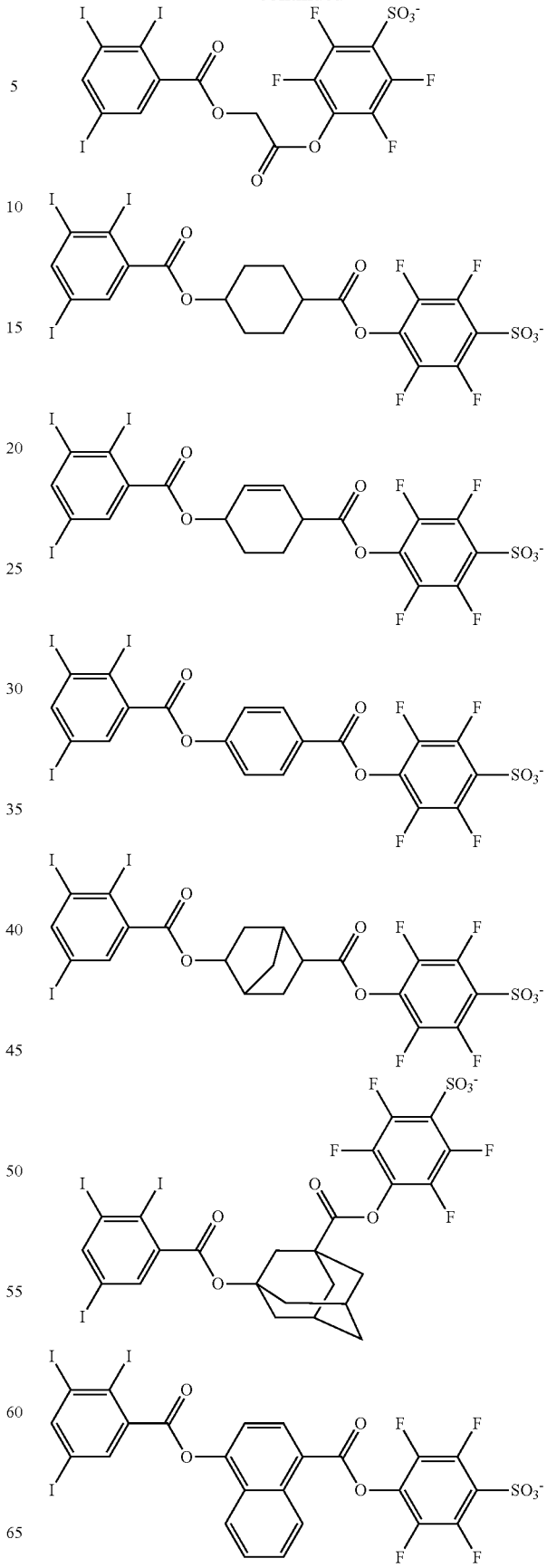

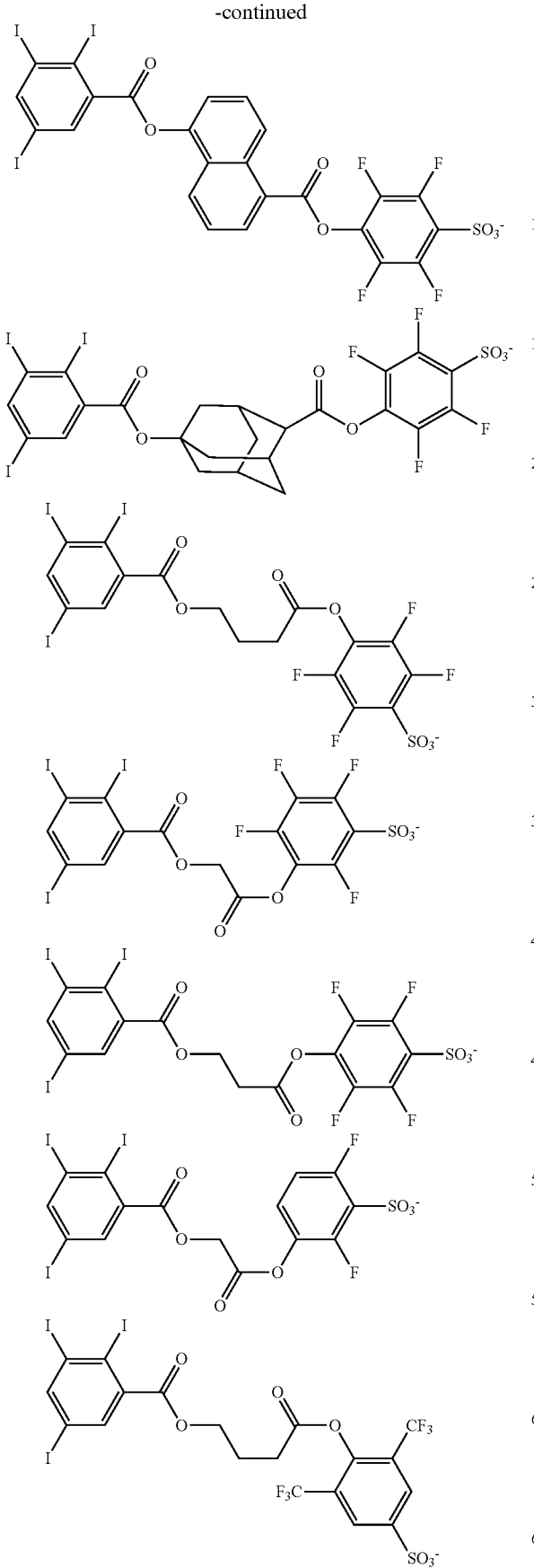
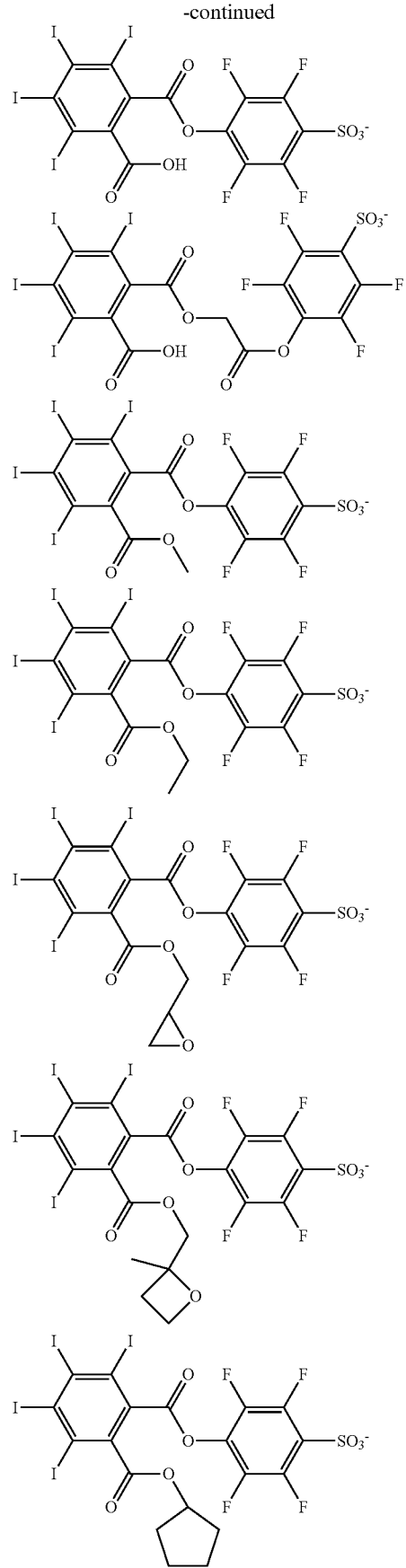

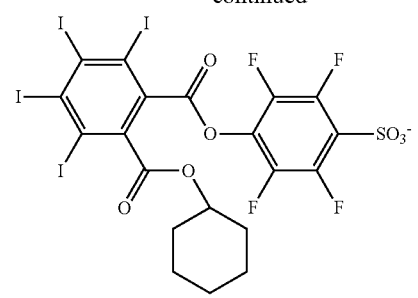
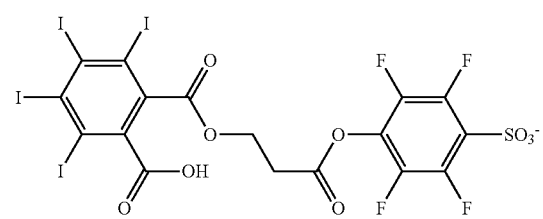
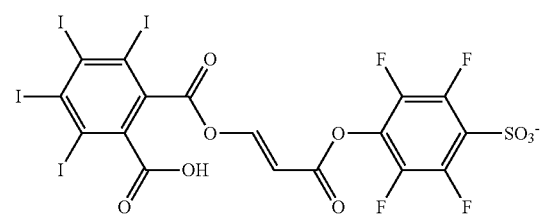
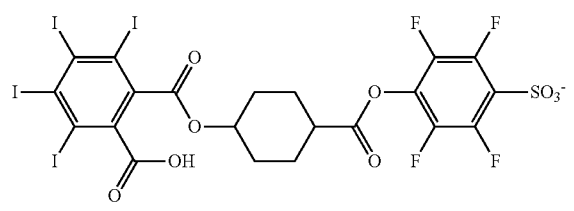
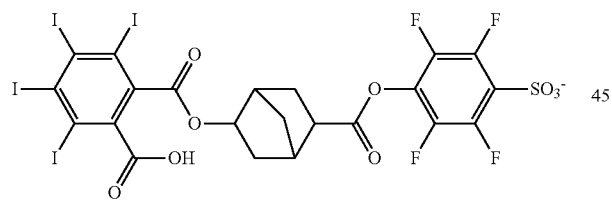
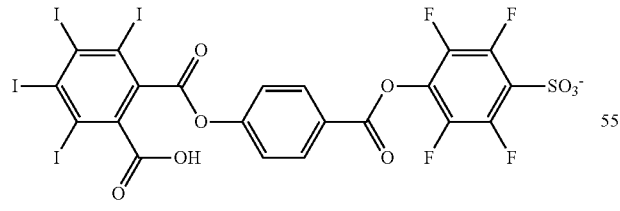
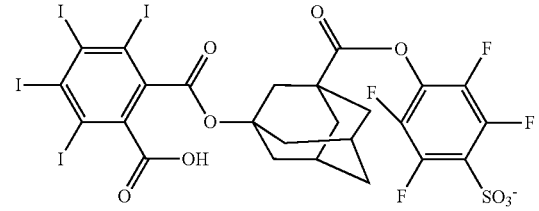
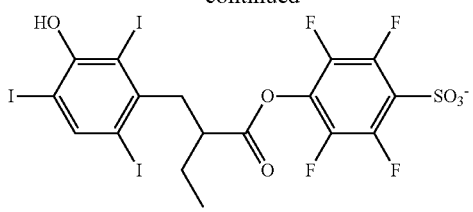
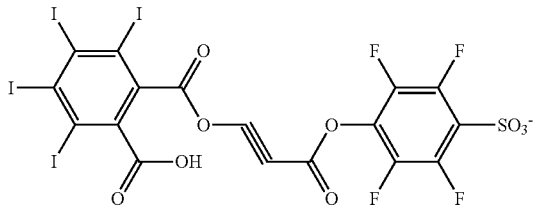
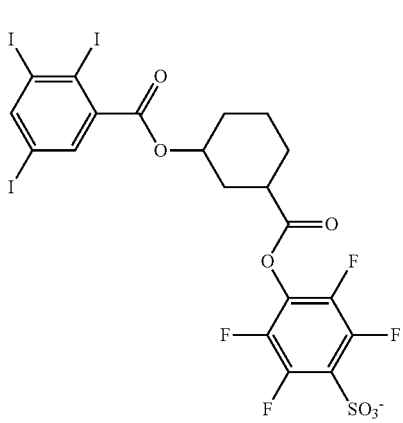
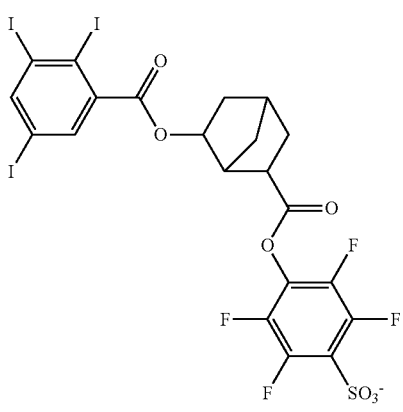
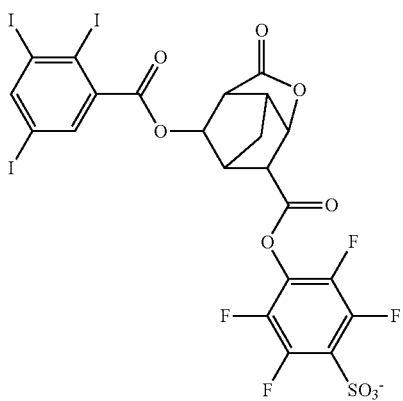

-continued

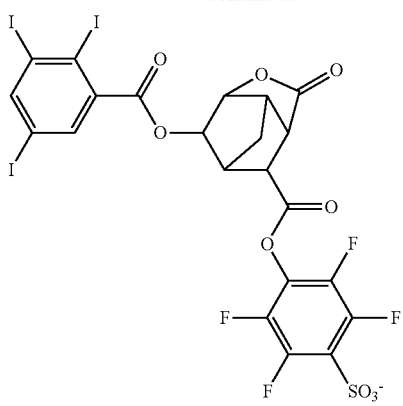

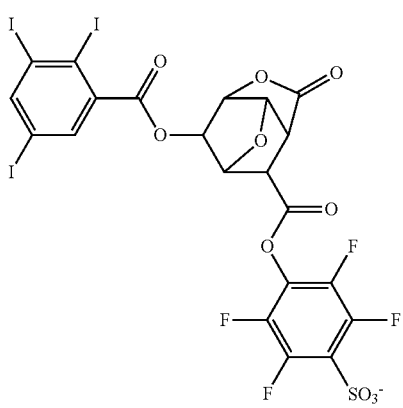

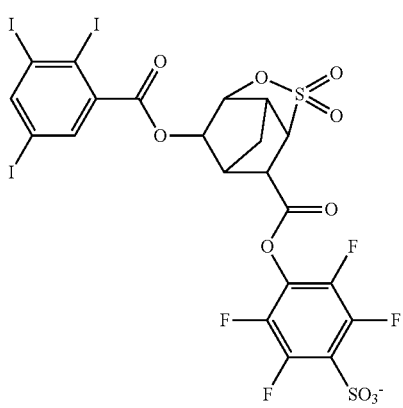

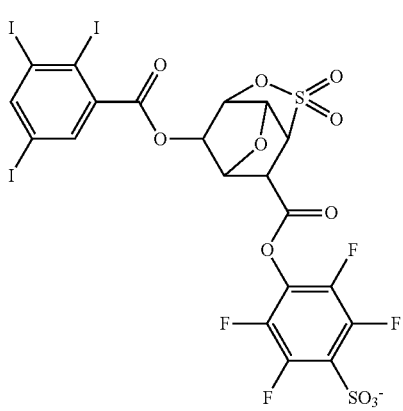

-continued

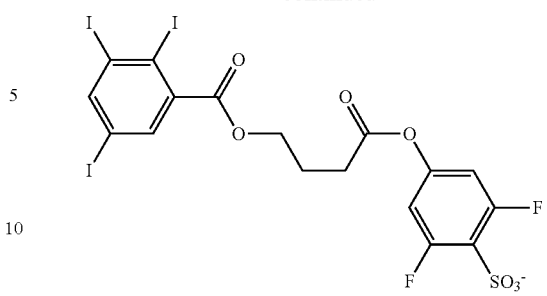

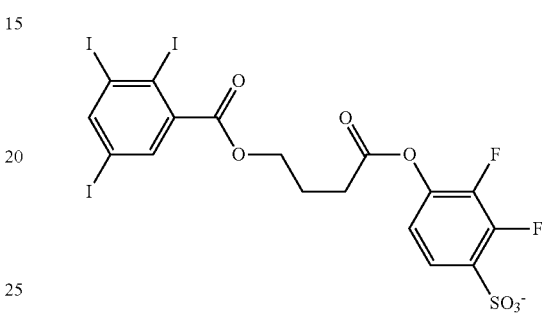

The sulfonium salt having formula (A-1) and the iodonium salt having formula (A-2) may be synthesized, for example, by ion exchange with a sulfonium or iodonium salt of weaker acid than the fluorobenzenesulfonic acid bonded to iodized benzoic acid. Examples of the weaker acid include carbonic acid, hydrochloric acid, and carboxylic acids. Alternatively, the sulfonium or iodonium salt may be synthesized by ion exchange of a sodium or ammonium salt of a fluorobenzenesulfonic acid bonded to iodized benzoic acid with a sulfonium chloride or iodonium chloride.

In the resist composition, the sulfonium salt having formula (A-1) or iodonium salt having formula (A-2) is preferably used in an amount of 0.01 to 1,000 parts, more preferably 0.05 to 500 parts by weight per 100 parts by weight of the base polymer, as viewed from sensitivity and acid diffusion suppressing effect.

Base Polymer

Where the resist composition is of positive tone, the base polymer comprises recurring units containing an acid labile group, preferably recurring units having the formula (a1) or recurring units having the formula (a2). These units are simply referred to as recurring units (a1) and (a2).

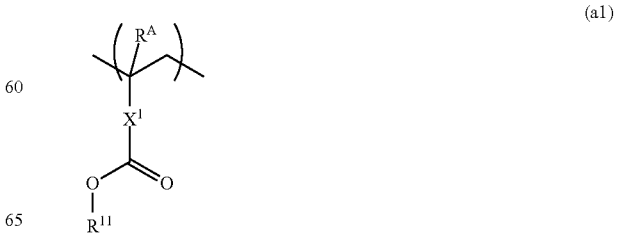

(a1)

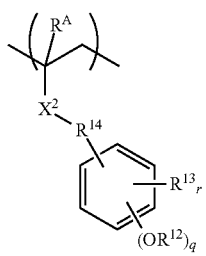
(a2)

Herein $R^A$ is each independently hydrogen or methyl. $X^1$ is a single bond, phenylene group, naphthylene group, or $C_1$-$C_{12}$ linking group containing an ester moiety and/or lactone ring. $X^2$ is a single bond or ester group. $R^{11}$ and $R^{12}$ each are an acid labile group. $R^{13}$ is fluorine, trifluoromethyl, cyano, $C_1$-$C_6$ straight, branched or cyclic alkyl or alkoxy group, or $C_2$-$C_7$ straight, branched or cyclic acyl, acyloxy or alkoxycarbonyl group. $R^{14}$ is a single bond or a $C_1$-$C_6$ straight or branched alkylene group in which at least one carbon (i.e., one or more carbon atoms) may be substituted by an ether or ester moiety, q is 1 or 2, and r is an integer of 0 to 4.

Examples of the recurring units (a1) are shown below, but not limited thereto. $R^A$ and $R^{11}$ are as defined above.

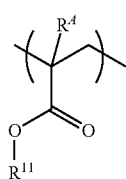 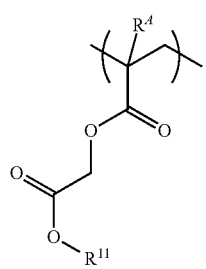

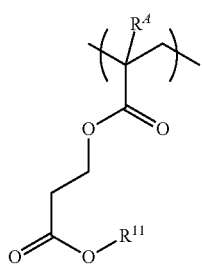 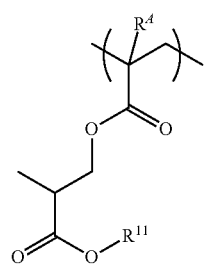

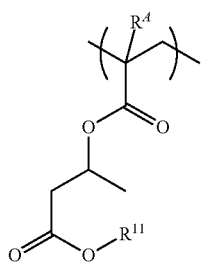 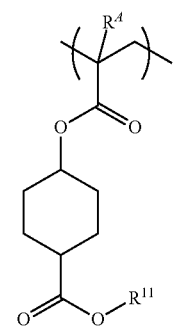

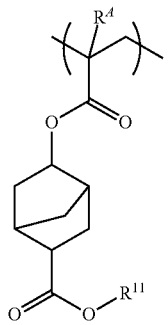 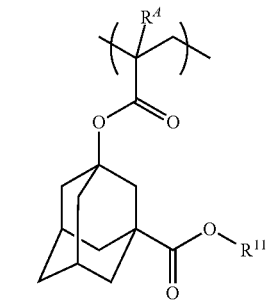

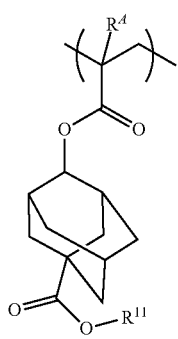 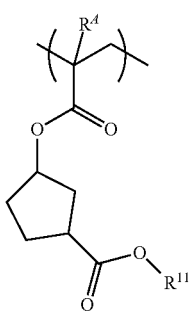

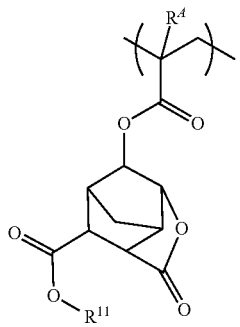

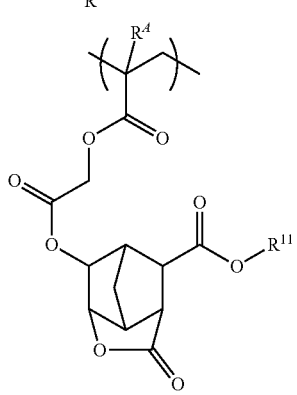 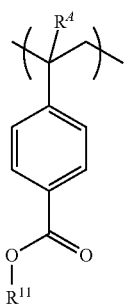

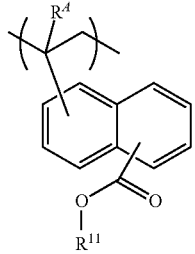

Examples of the recurring units (a2) are shown below, but not limited thereto. $R^A$ and $R^{12}$ are as defined above.

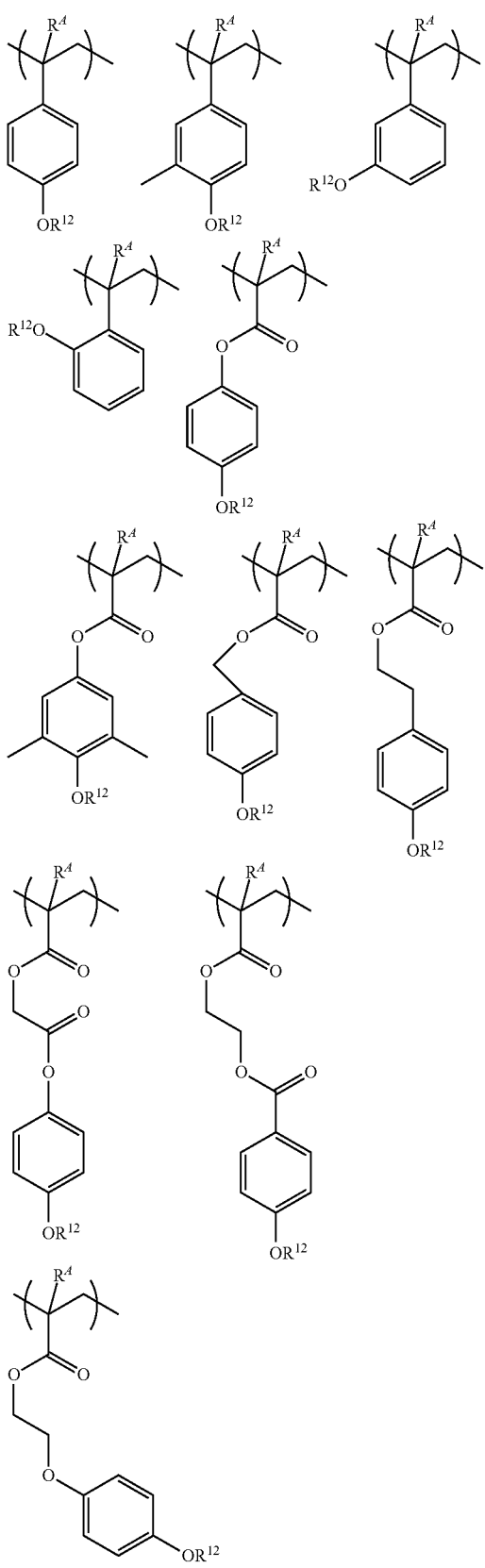

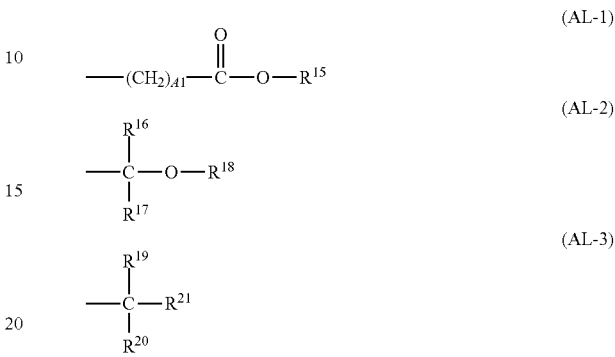

of such groups, for example, those groups described in JP-A 2013-080033 (U.S. Pat. No. 8,574,817) and JP-A 2013-083821 (U.S. Pat. No. 8,846,303).

Typical of the acid labile group are groups of the following formulae (AL-1) to (AL-3).

In formulae (AL-1) and (AL-2), $R^{15}$ and $R^{18}$ are each independently a monovalent hydrocarbon group of 1 to 40 carbon atoms, preferably 1 to 20 carbon atoms, typically straight, branched or cyclic alkyl, which may contain a heteroatom such as oxygen, sulfur, nitrogen or fluorine. $R^{16}$ and $R^{17}$ are each independently hydrogen or a monovalent hydrocarbon group of 1 to 20 carbon atoms, typically straight, branched or cyclic alkyl, which may contain a heteroatom such as oxygen, sulfur, nitrogen or fluorine. Any two of $R^{16}$, $R^{17}$, and $R^{18}$ may bond together to form a ring, typically alicyclic, with the carbon atom or carbon and oxygen atoms to which they are attached, the ring containing 3 to 20 carbon atoms, preferably 4 to 16 carbon atoms. A1 is an integer of 0 to 10, especially 1 to 5.

In formula (AL-3), $R^{19}$, $R^{20}$ and $R^{21}$ are each independently a monovalent hydrocarbon group of 1 to 20 carbon atoms, typically straight, branched or cyclic alkyl, which may contain a heteroatom such as oxygen, sulfur, nitrogen or fluorine. Any two of $R^{19}$, $R^{20}$, and $R^{21}$ may bond together to form a ring, typically alicyclic, with the carbon atom to which they are attached, the ring containing 3 to 20 carbon atoms, preferably 4 to 16 carbon atoms.

The base polymer may further comprise recurring units (b) having a phenolic hydroxyl group as an adhesive group. Examples of suitable monomers from which recurring units (b) are derived are given below, but not limited thereto. Herein $R^A$ is as defined above.

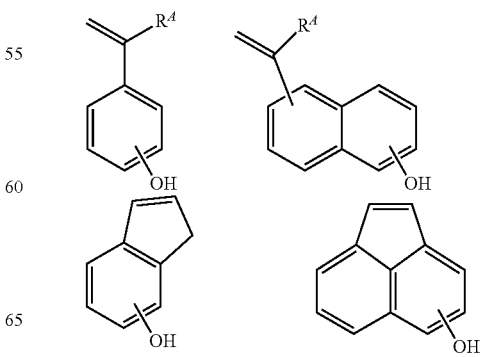

The acid labile groups represented by $R^{11}$ and $R^{12}$ in the recurring units (a1) and (a2) may be selected from a variety

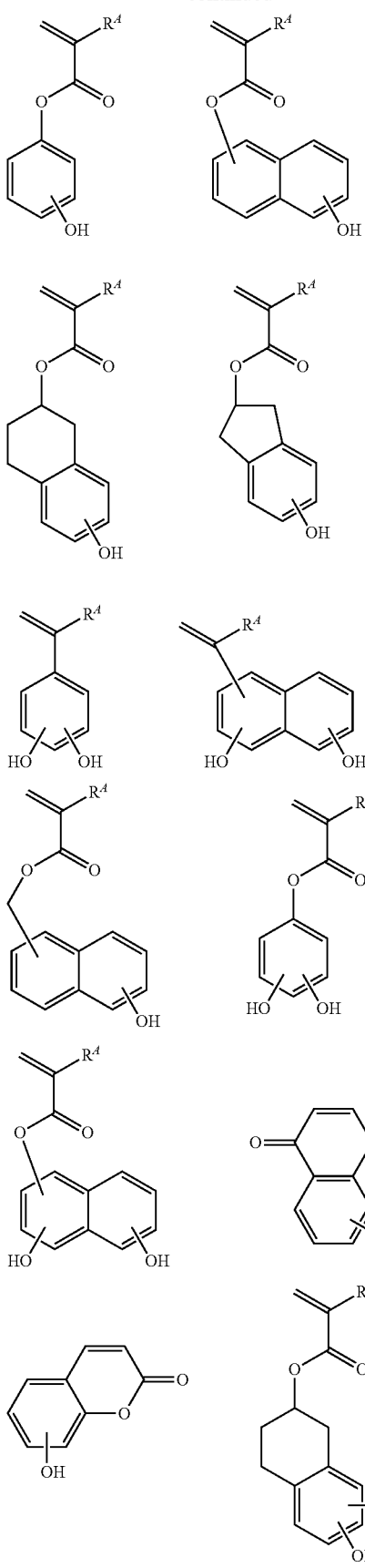

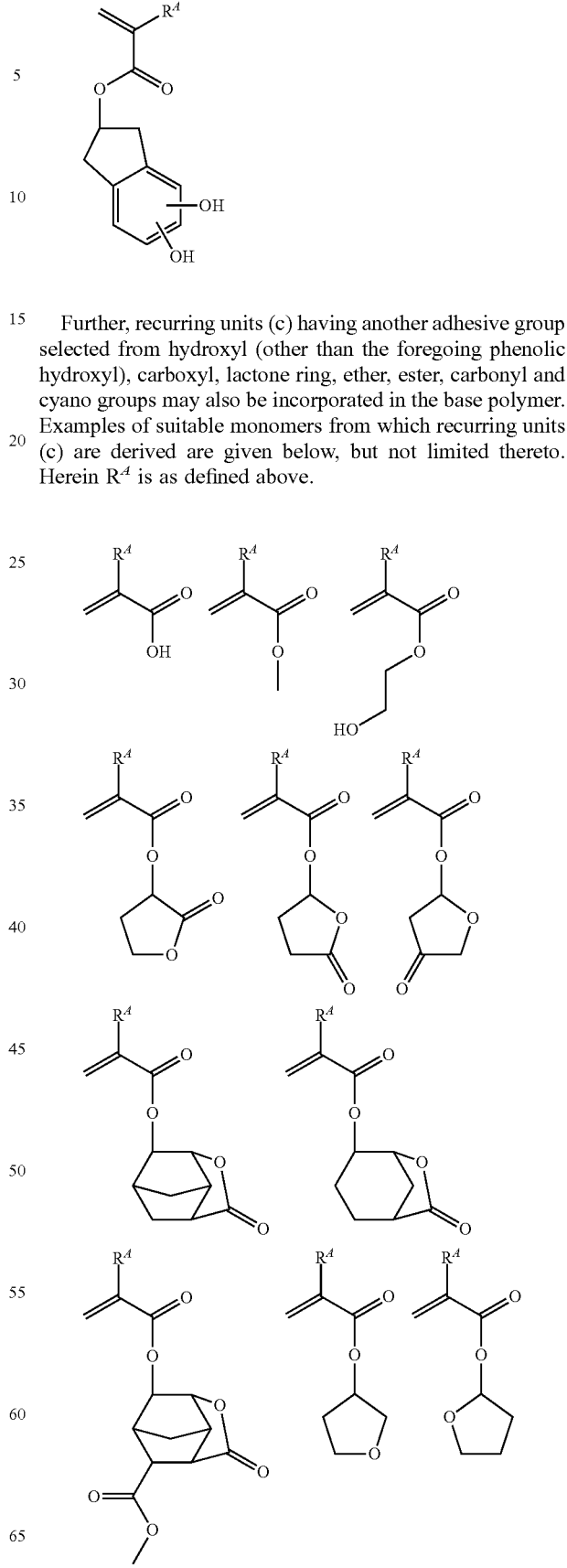

Further, recurring units (c) having another adhesive group selected from hydroxyl (other than the foregoing phenolic hydroxyl), carboxyl, lactone ring, ether, ester, carbonyl and cyano groups may also be incorporated in the base polymer. Examples of suitable monomers from which recurring units (c) are derived are given below, but not limited thereto. Herein $R^A$ is as defined above.

-continued
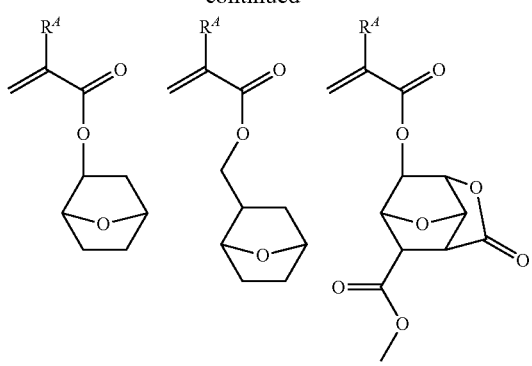
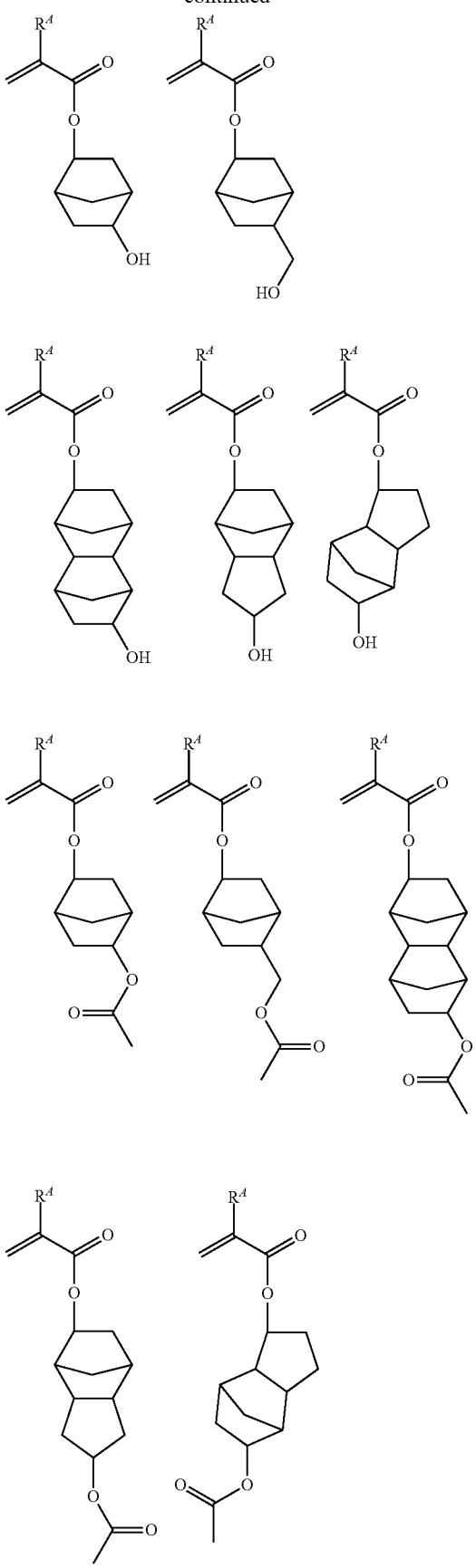

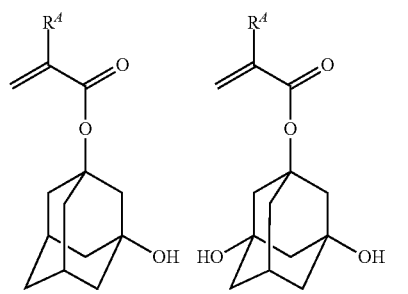
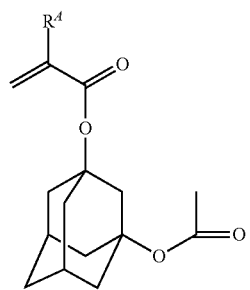
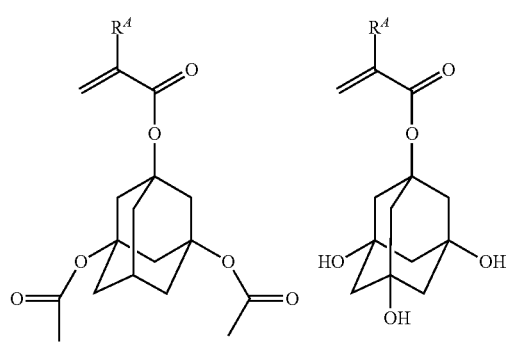
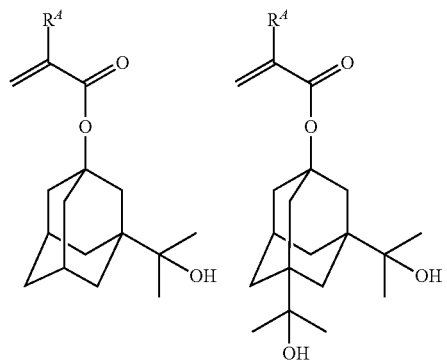
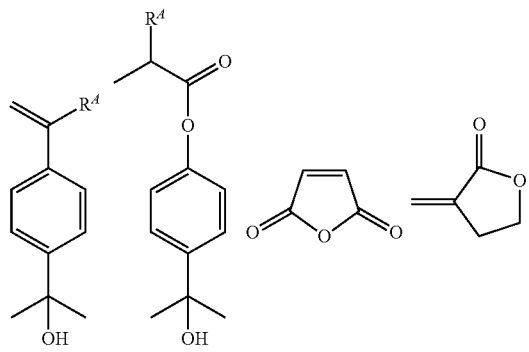
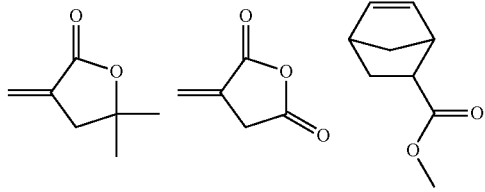
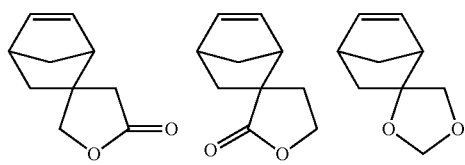
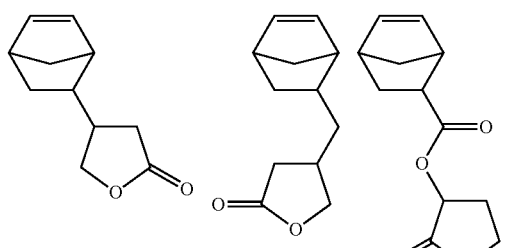
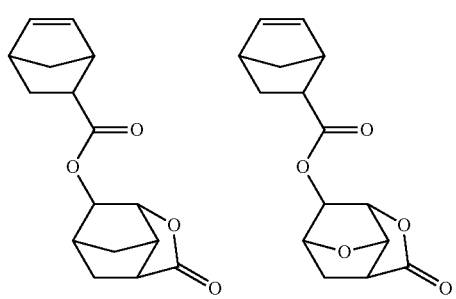
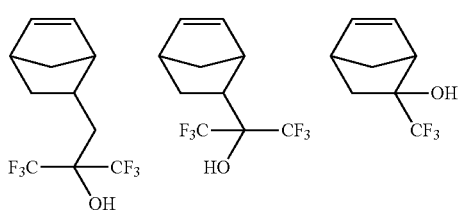
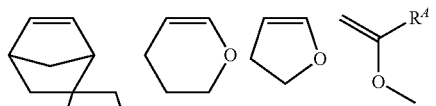
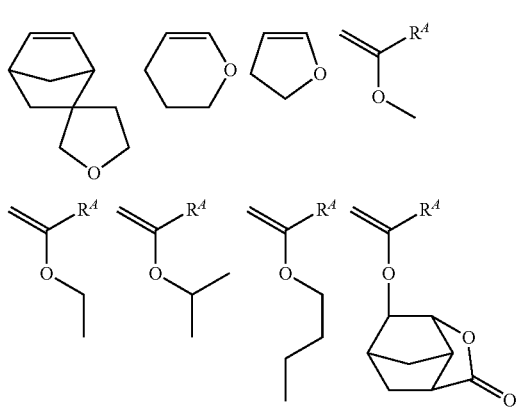

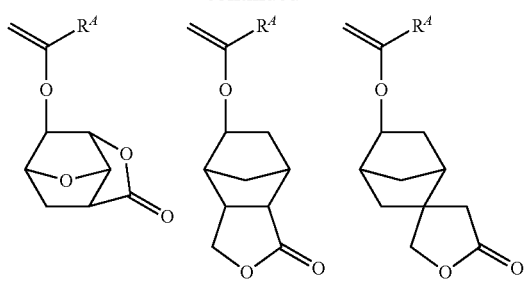
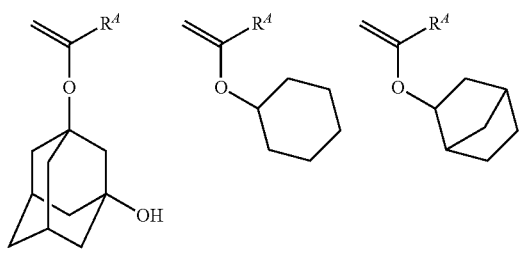
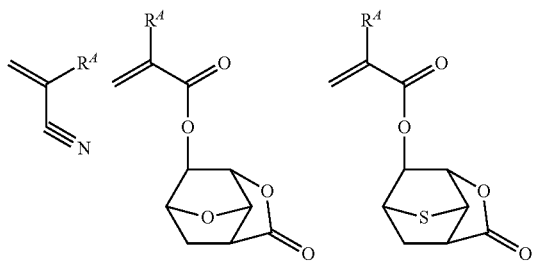
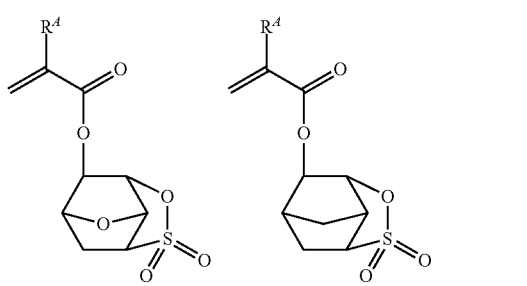
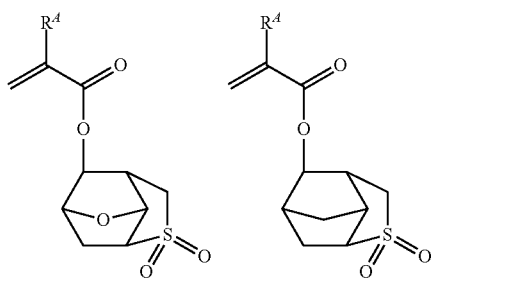
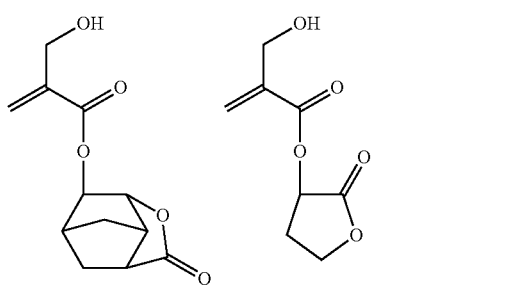
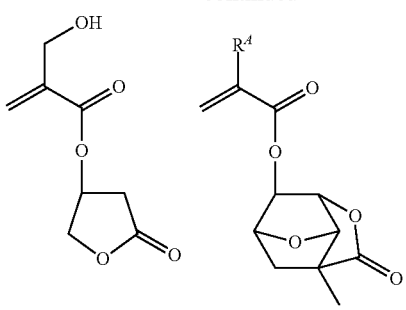
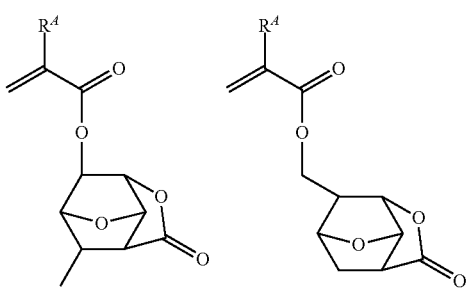
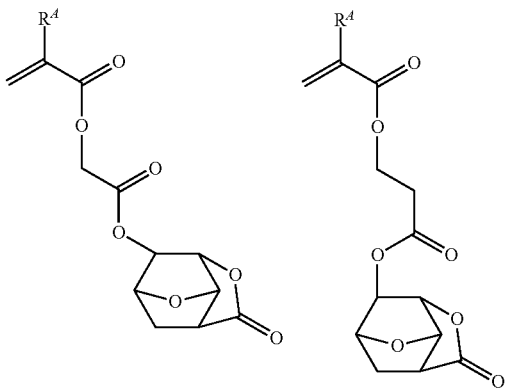
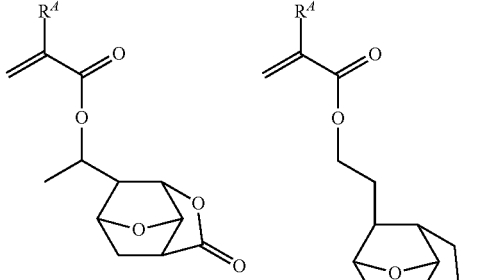
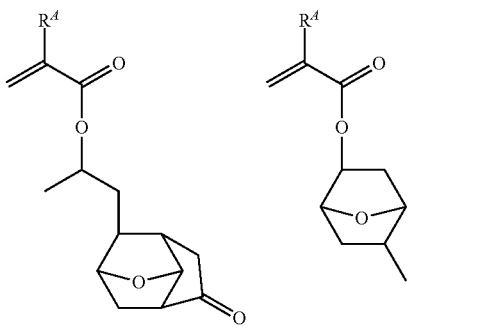

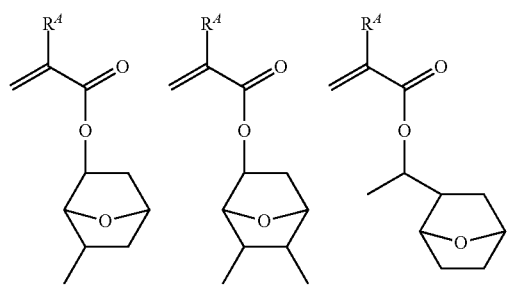
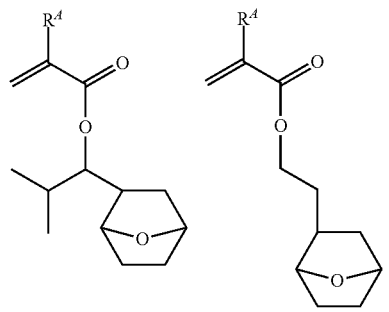
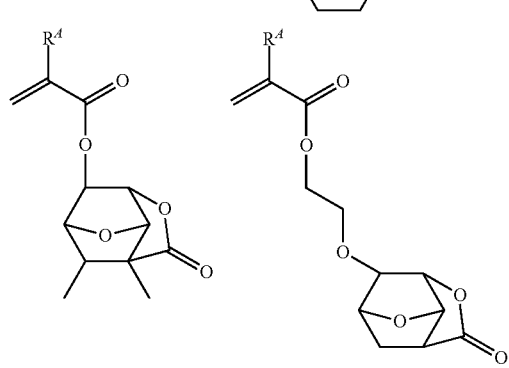
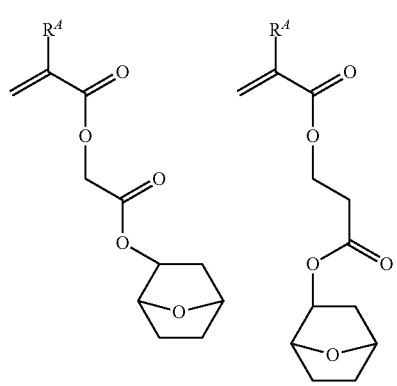
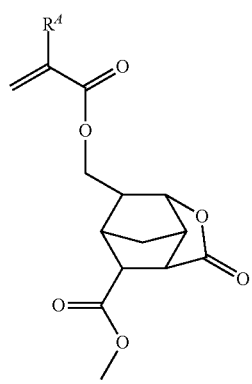
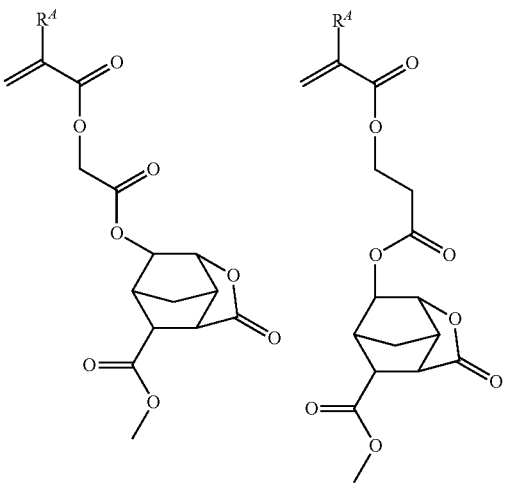
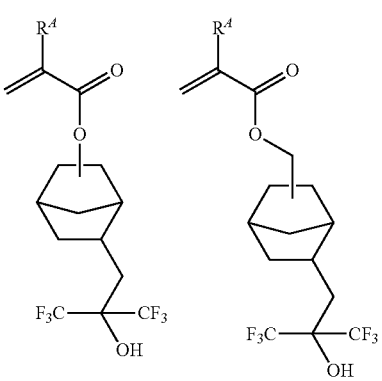
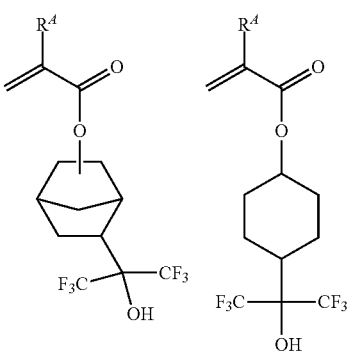
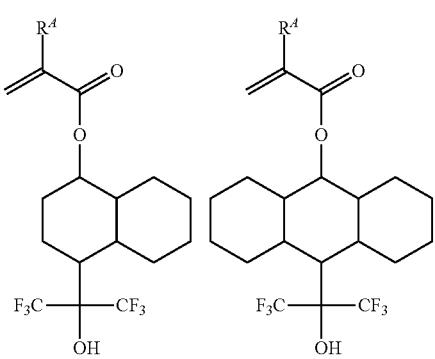

-continued
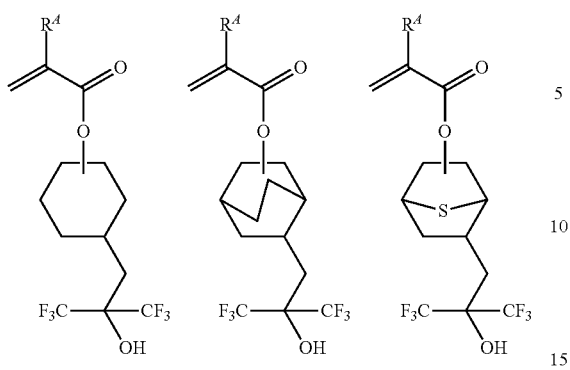
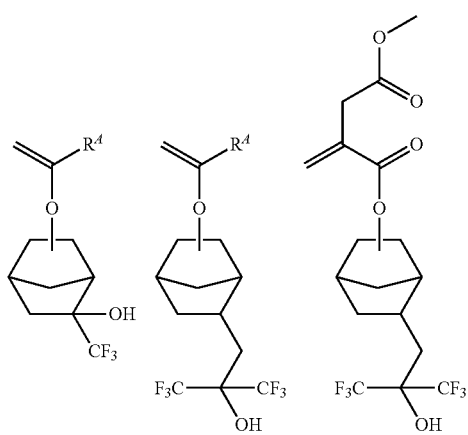
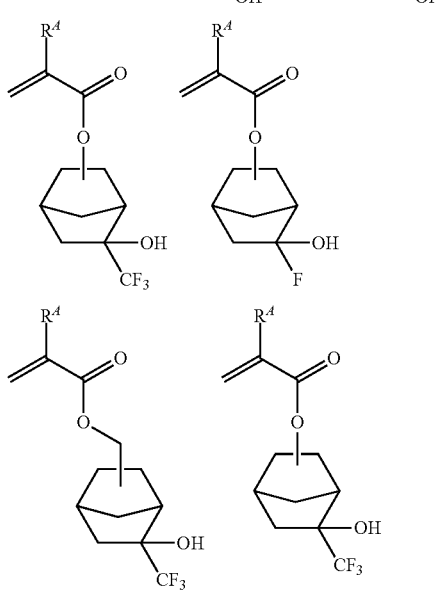
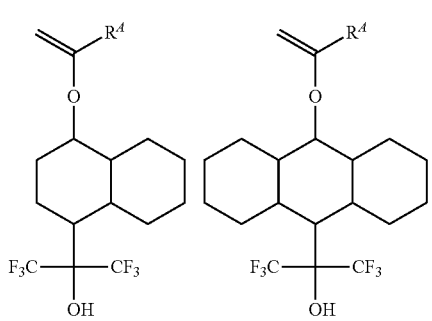
-continued
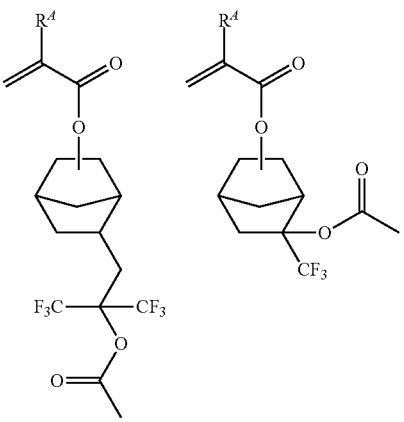
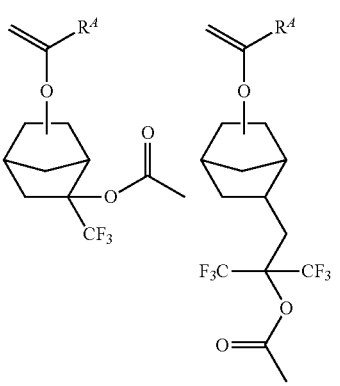
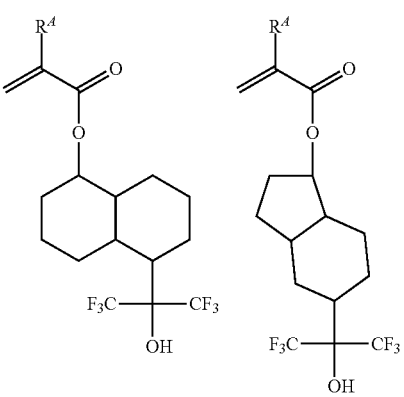
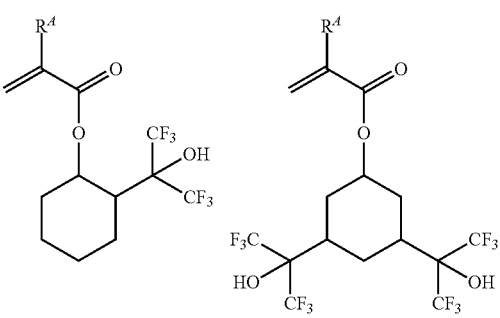

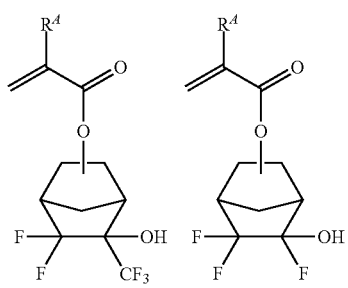
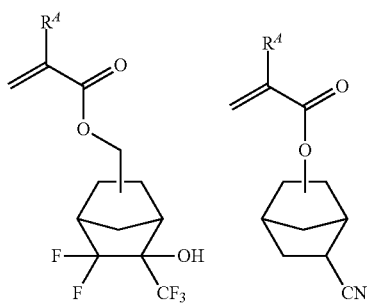
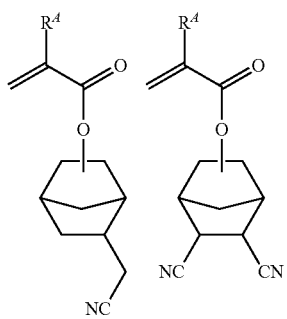
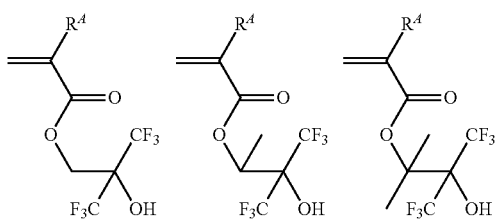
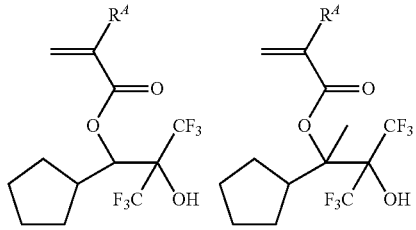
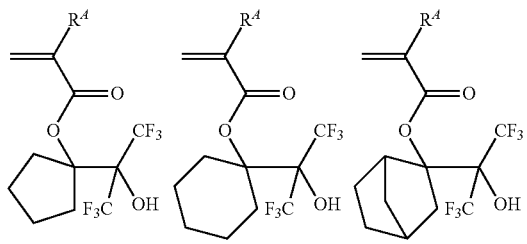
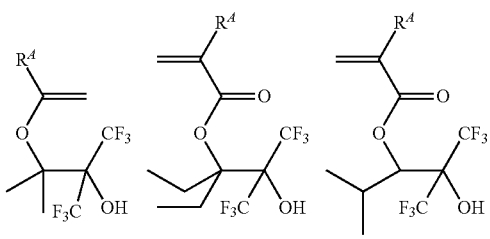
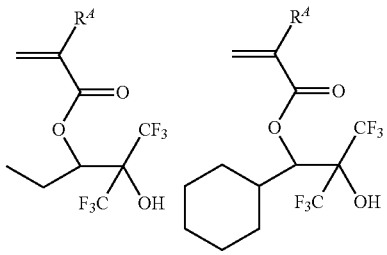
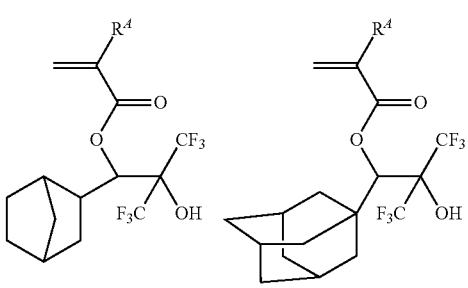
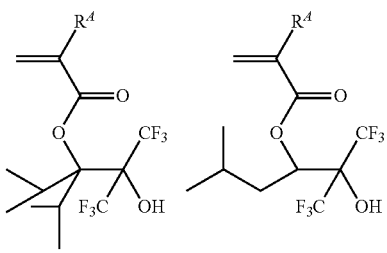
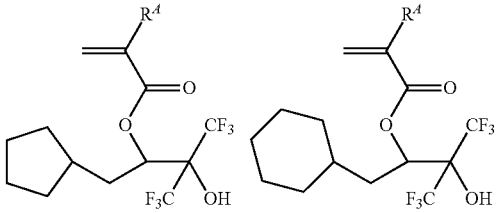
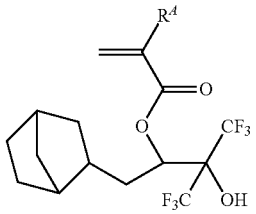
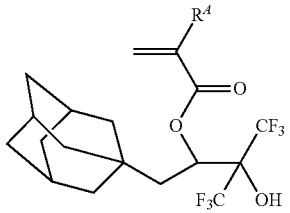

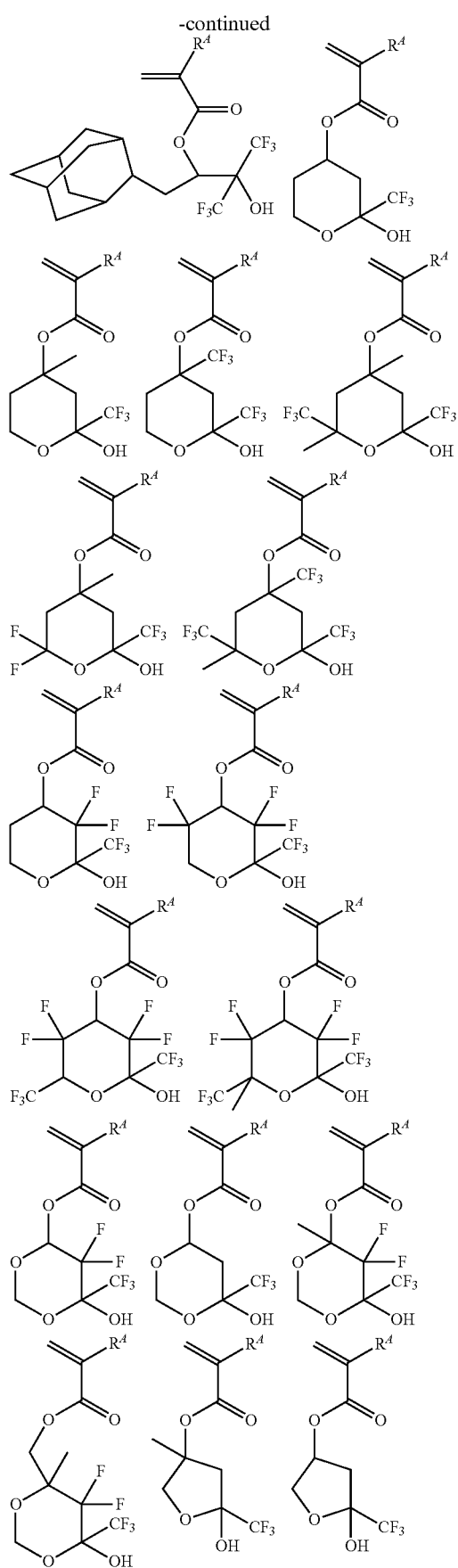
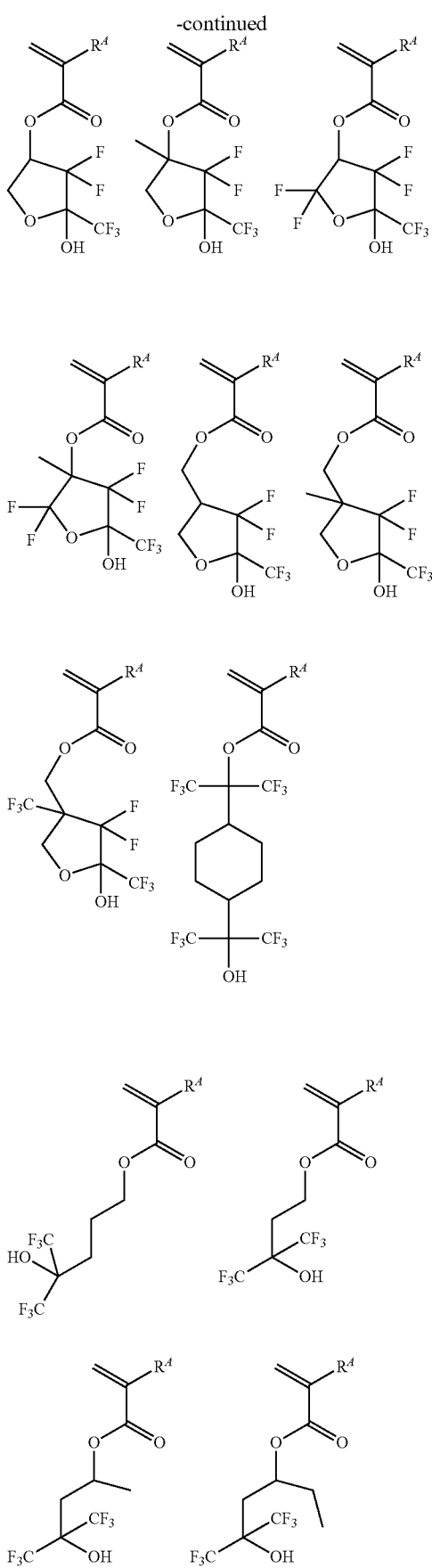

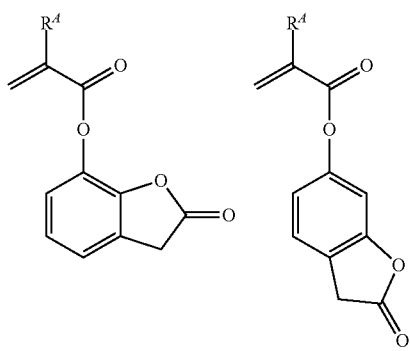
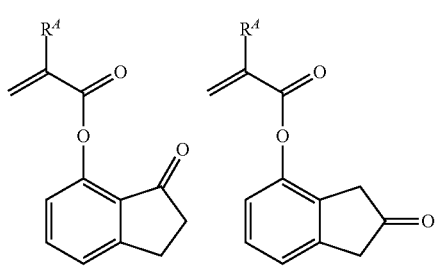
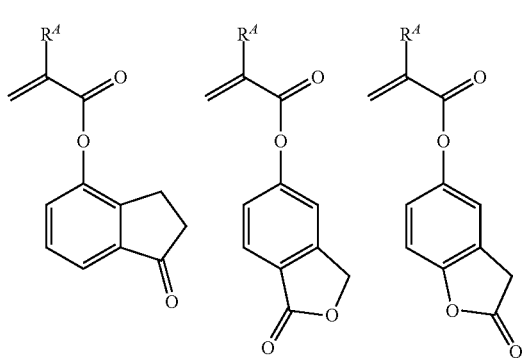
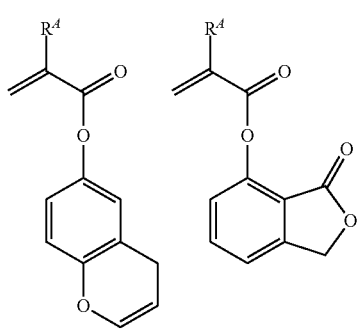
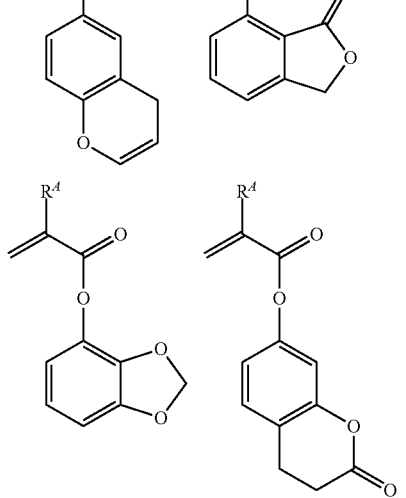
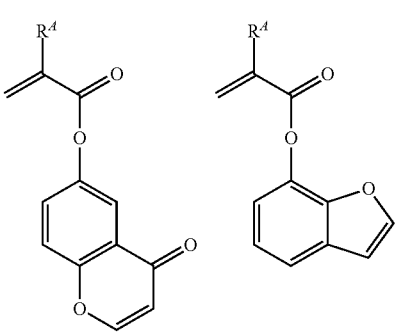
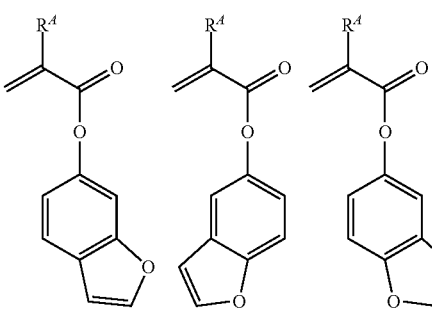
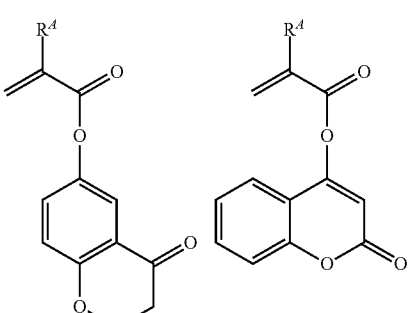
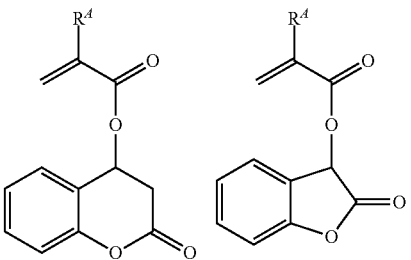

-continued

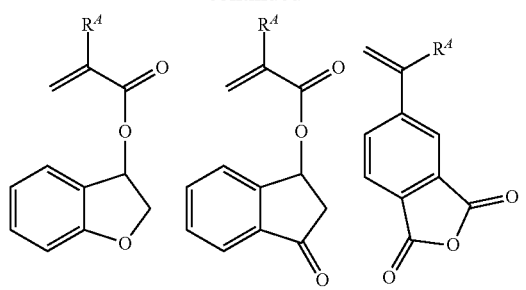
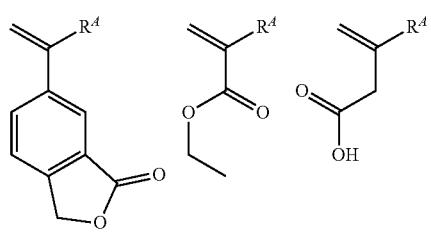
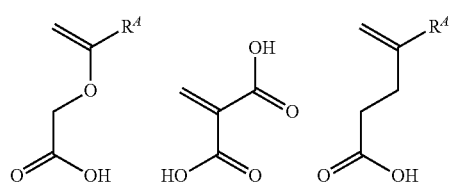
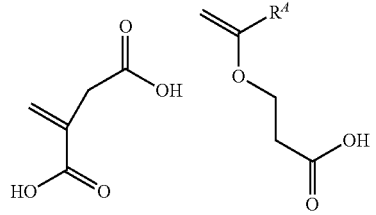
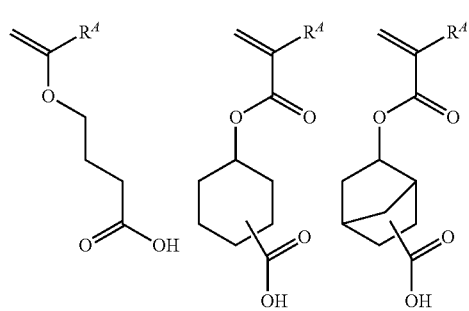
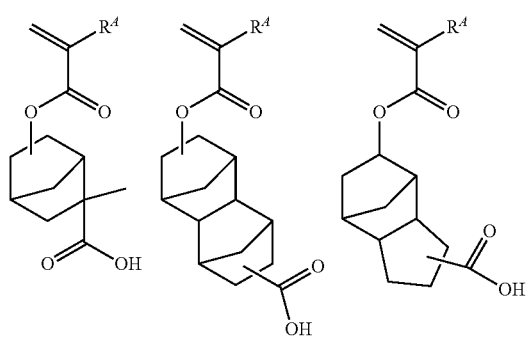

-continued

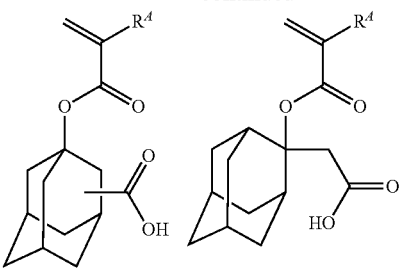
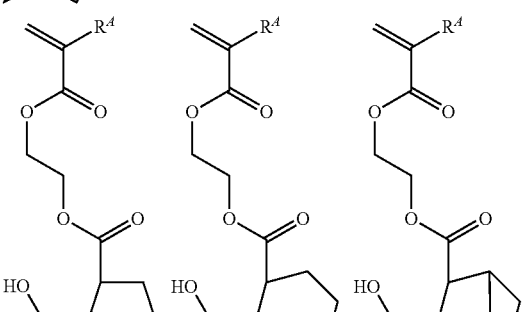
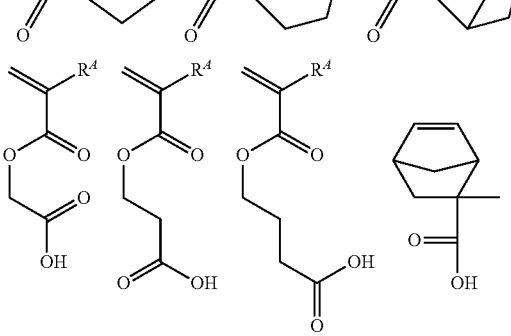
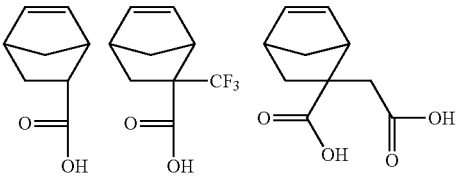
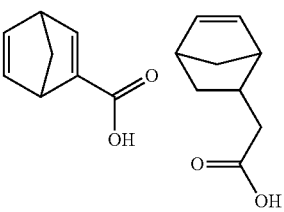

In the case of a monomer having a hydroxyl group, the hydroxyl group may be replaced by an acetal group susceptible to deprotection with acid, typically ethoxyethoxy, prior to polymerization, and the polymerization be followed by deprotection with weak acid and water. Alternatively, the hydroxyl group may be replaced by an acetyl, formyl, pivaloyl or similar group prior to polymerization, and the polymerization be followed by alkaline hydrolysis.

In another preferred embodiment, the base polymer may further comprise recurring units (d) selected from units of indene, benzofuran, benzothiophene, acenaphthylene, chromone, coumarin, and norbornadiene, or derivatives thereof. Suitable monomers are exemplified below.

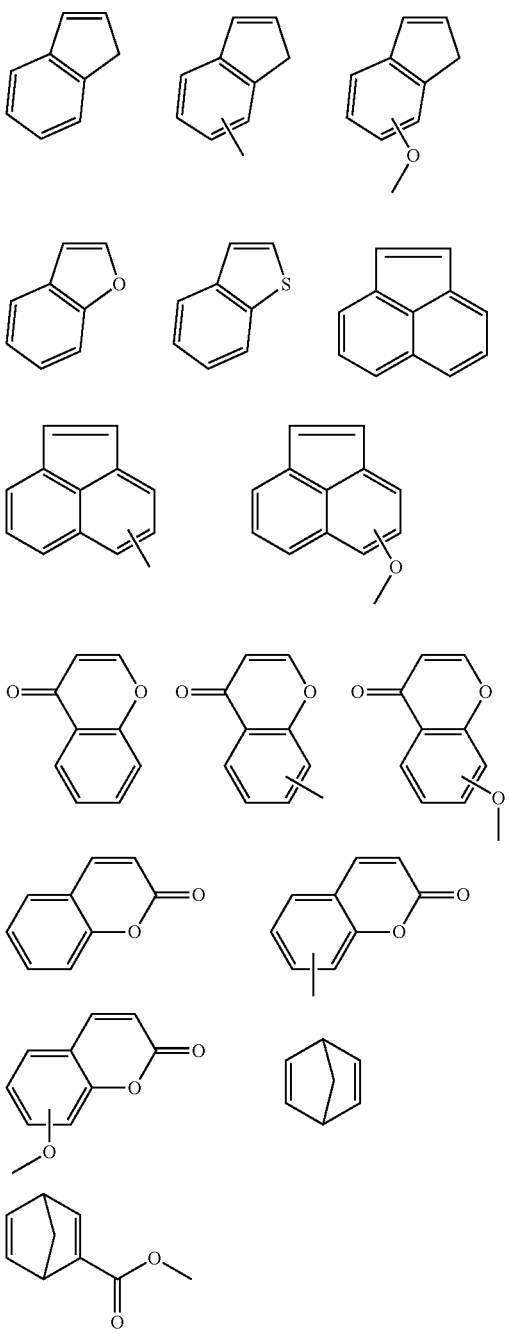

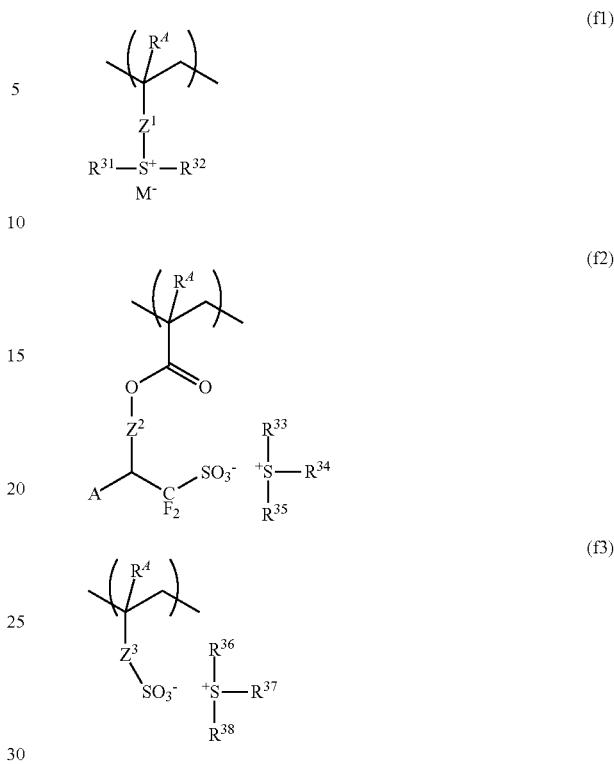

Besides the recurring units described above, further recurring units (e) may be incorporated in the base polymer, examples of which include styrene, vinylnaphthalene, vinylanthracene, vinylpyrene, methyleneindane, vinylpyridine, and vinylcarbazole.

In a further embodiment, recurring units (f) derived from an onium salt having a polymerizable unsaturated bond may be incorporated in the base polymer. The preferred recurring units (f) include recurring units having formula (f1), recurring units having formula (f2), and recurring units having formula (f3). These units are simply referred to as recurring units (f1), (f2) and (13), which may be used alone or in combination of two or more types.

Herein $R^A$ is each independently hydrogen or methyl. $Z^1$ is a single bond, phenylene group, —O—$Z^2$—, or —C(=O)—$Z^{11}$-$Z^{12}$—, wherein $Z^{11}$ is —O— or —NH— and $Z^{12}$ is a $C_1$-$C_6$ straight, branched or cyclic alkylene group, $C_2$-$C_6$ straight, branched or cyclic alkenylene group, or phenylene group, which may contain a carbonyl, ester, ether or hydroxyl moiety. $R^{31}$ to $R^{38}$ are each independently a $C_1$-$C_{12}$ straight, branched or cyclic alkyl group which may contain a carbonyl, ester or ether moiety, or a $C_6$-$C_{12}$ aryl group or $C_7$-$C_{20}$ aralkyl group, in which at least one hydrogen (i.e., one or more or even all hydrogen atoms) may be substituted by a $C_1$-$C_{10}$ straight, branched or cyclic alkyl moiety, halogen, trifluoromethyl, cyano, nitro, hydroxyl, mercapto, $C_1$-$C_{10}$ straight, branched or cyclic alkoxy moiety, $C_2$-$C_{10}$ straight, branched or cyclic alkoxycarbonyl moiety, or $C_2$-$C_{10}$ straight, branched or cyclic acyloxy moiety. Also, any two of $R^{33}$, $R^{34}$, and $R^{35}$, or any two of $R^{36}$, $R^{37}$ and $R^{38}$ may bond together to form a ring with the sulfur atom to which they are attached. $Z^2$ is a single bond, —$Z^{21}$—C(=O)—O—, —$Z^{21}$—O— or —$Z^{21}$—O—C(=O)—, wherein $Z^{21}$ is a straight, branched or cyclic $C_1$-$C_{12}$ alkylene group which may contain a carbonyl, ester or ether moiety. A is hydrogen or trifluoromethyl. $Z^3$ is a single bond, methylene group, ethylene group, phenylene group, fluorinated phenylene group, —O—$Z^{32}$—, or —C(=O)—$Z^{31}$-$Z^{32}$—, wherein $Z^{31}$ is —O— or —NH— and $Z^{32}$ is a $C_1$-$C_6$ straight, branched or cyclic alkylene group, phenylene, fluorinated phenylene, trifluoromethyl-substituted phenylene group, or $C_2$-$C_6$ straight, branched or cyclic alkenylene group, which may contain a carbonyl, ester, ether or hydroxyl moiety. $M^-$ is a non-nucleophilic counter ion.

Examples of the monomer from which recurring unit (f1) is derived are shown below, but not limited thereto. $R^A$ and $M^-$ are as defined above.

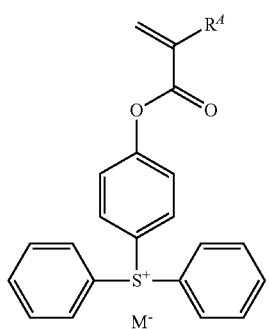
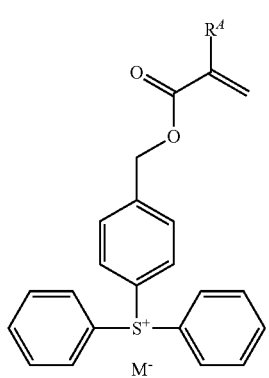
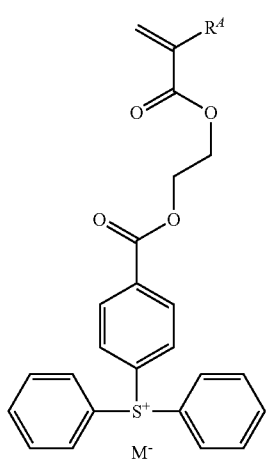
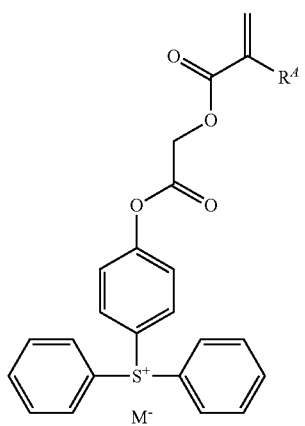
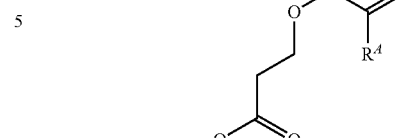
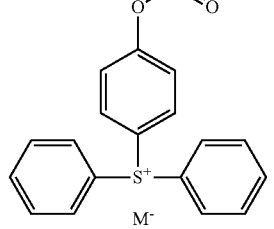
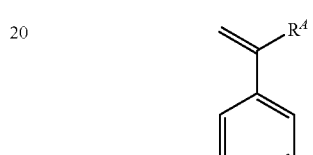
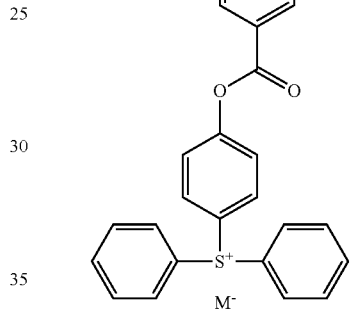
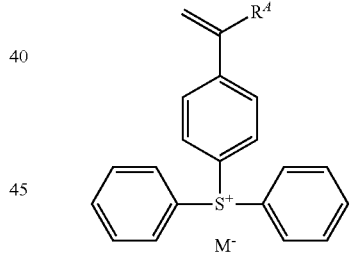
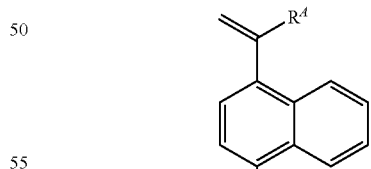
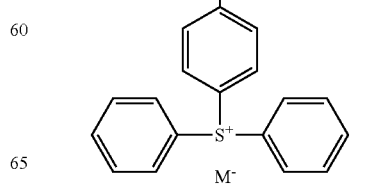

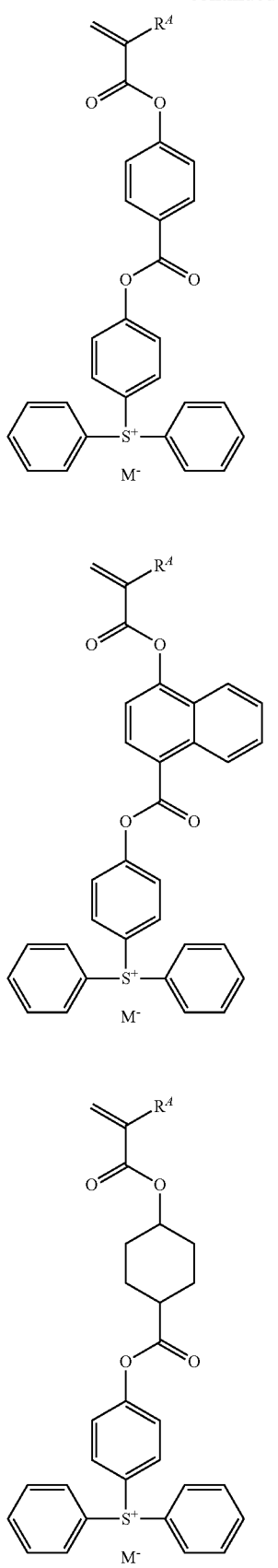

Examples of the non-nucleophilic counter ion M⁻ include halide ions such as chloride and bromide ions; fluoroalkylsulfonate ions such as triflate, 1,1,1-trifluoroethanesulfonate, and nonafluorobutanesulfonate; arylsulfonate ions such as tosylate, benzenesulfonate, 4-fluorobenzenesulfonate, and 1,2,3,4,5-pentafluorobenzenesulfonate; alkylsulfonate ions such as mesylate and butanesulfonate; imidates such as bis(trifluoromethylsulfonyl)imide, bis(perfluoroethylsulfonyl)imide and bis(perfluorobutylsulfonyl)imide; methidates such as tris(trifluoromethylsulfonyl)methide and tris(perfluoroethylsulfonyl)methide.

Also included are sulfonates having fluorine substituted at α-position as represented by the formula (K-1) and sulfonates having fluorine substituted at α- and β-positions as represented by the formula (K-2).

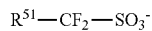  (K-1)

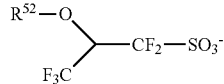  (K-2)

In formula (K-1), $R^{51}$ is hydrogen, or a $C_1$-$C_{20}$ straight, branched or cyclic alkyl group, $C_2$-$C_{20}$ straight, branched or cyclic alkenyl group, or $C_6$-$C_{20}$ aryl group, which may contain an ether, ester, carbonyl moiety, lactone ring, or fluorine atom. In formula (K-2), $R^{52}$ is hydrogen, or a $C_1$-$C_{30}$ straight, branched or cyclic alkyl group, $C_2$-$C_{20}$ straight, branched or cyclic acyl group, $C_2$-$C_{20}$ straight, branched or cyclic alkenyl group, $C_6$-$C_{20}$ aryl group or $C_6$-$C_{20}$ aryloxy group, which may contain an ether, ester, carbonyl moiety or lactone ring.

Examples of the monomer from which recurring unit (f2) is derived are shown below, but not limited thereto. $R^A$ is as defined above.

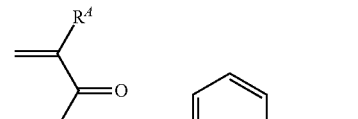

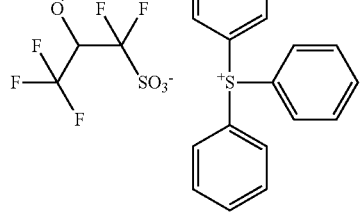

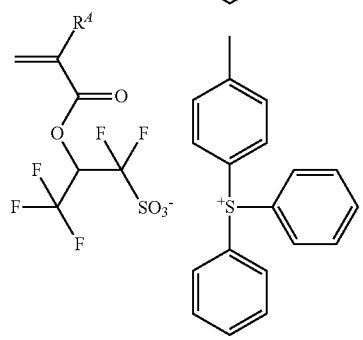

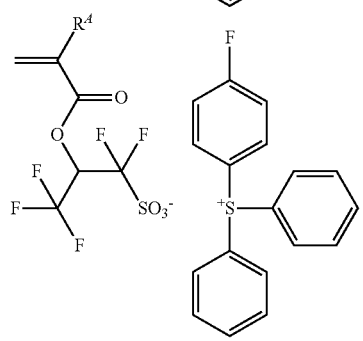

-continued

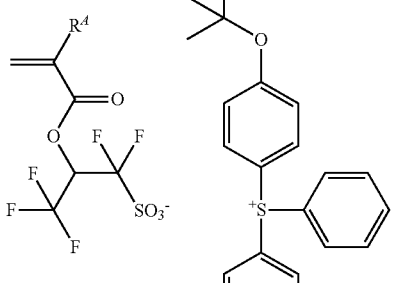

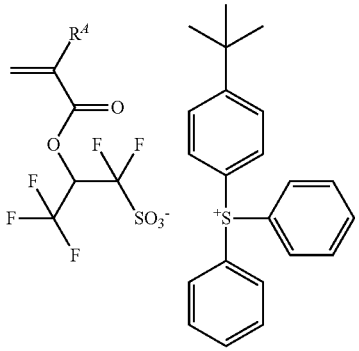

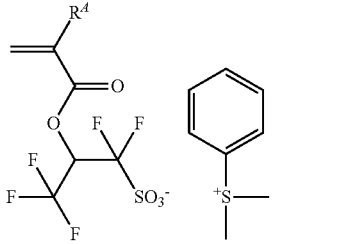

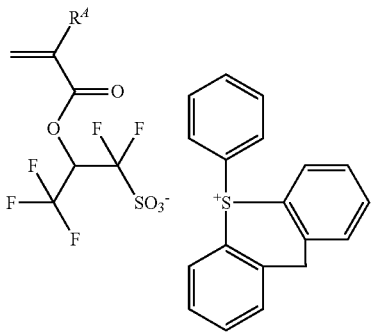

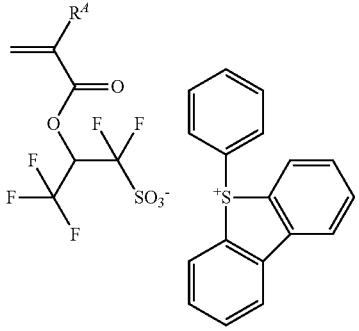

87
-continued
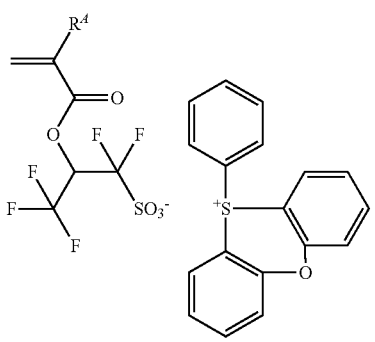
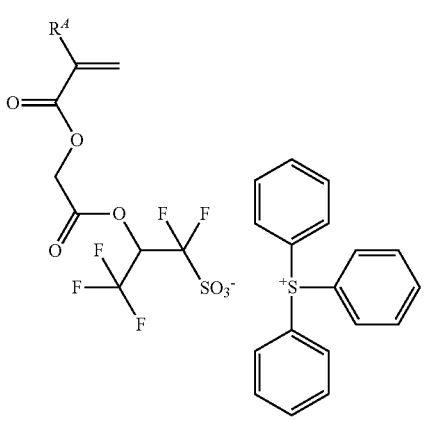
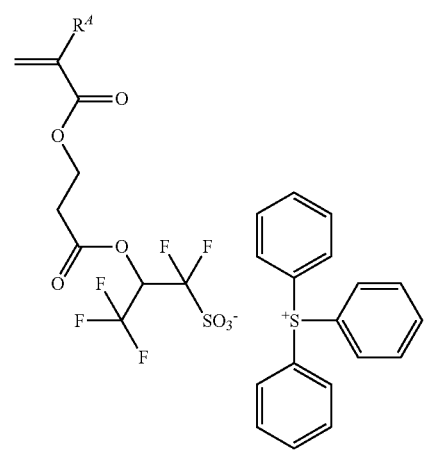
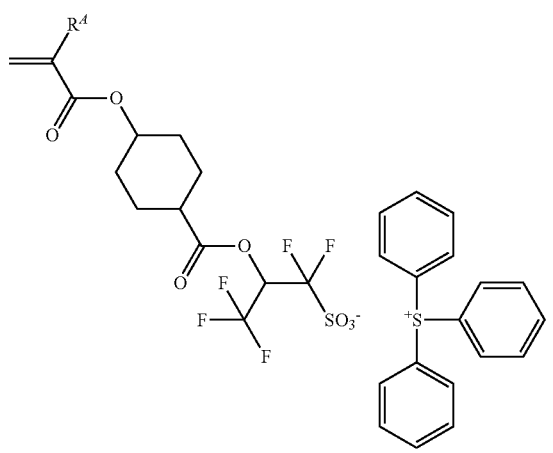
88
-continued
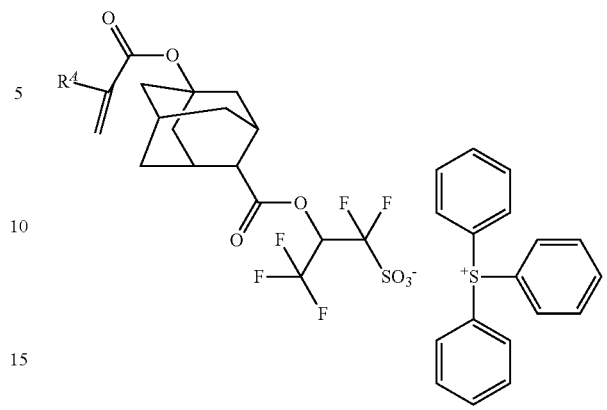
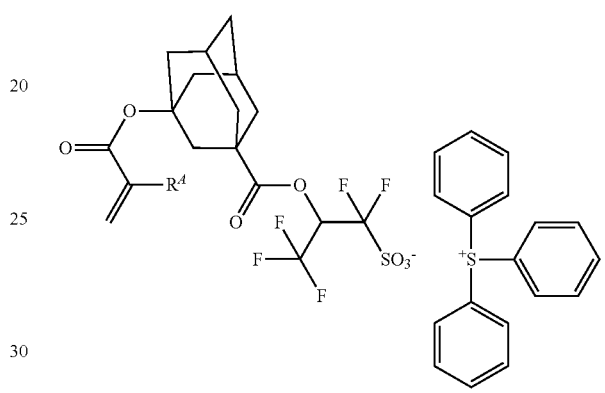
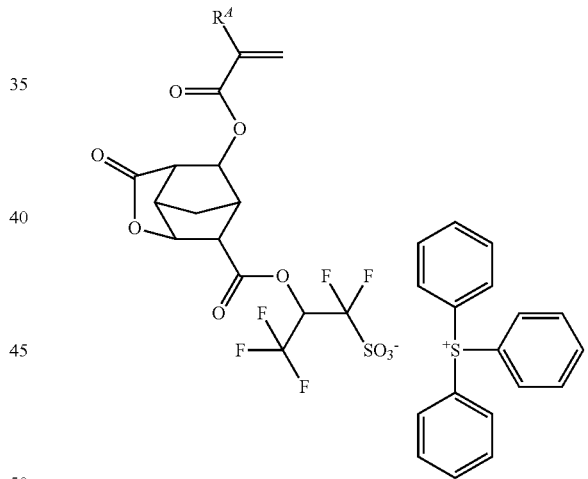
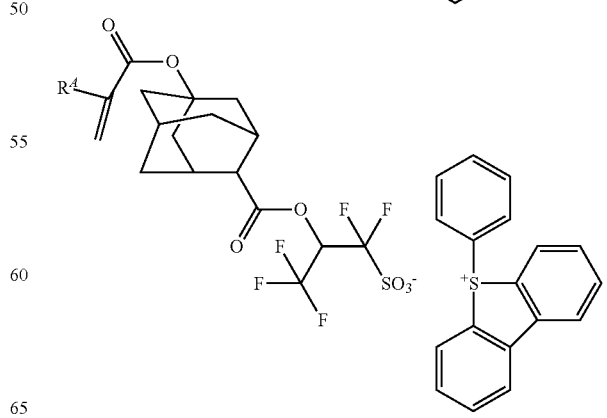

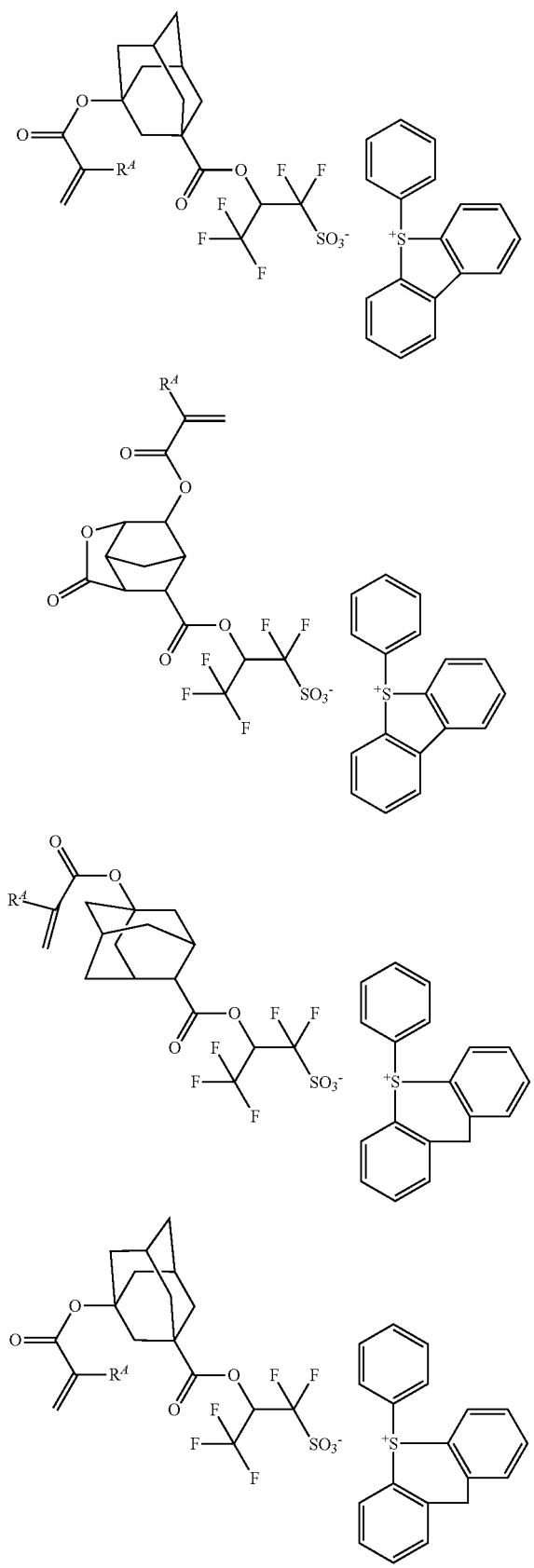
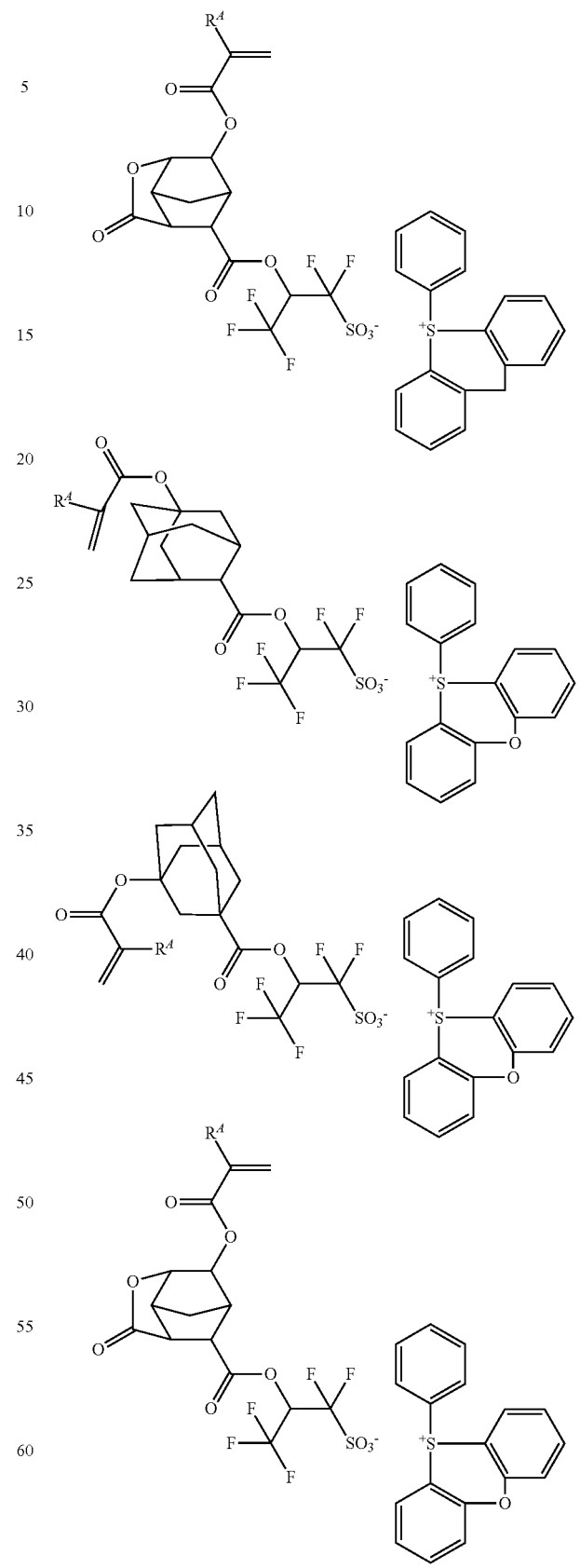

91
-continued
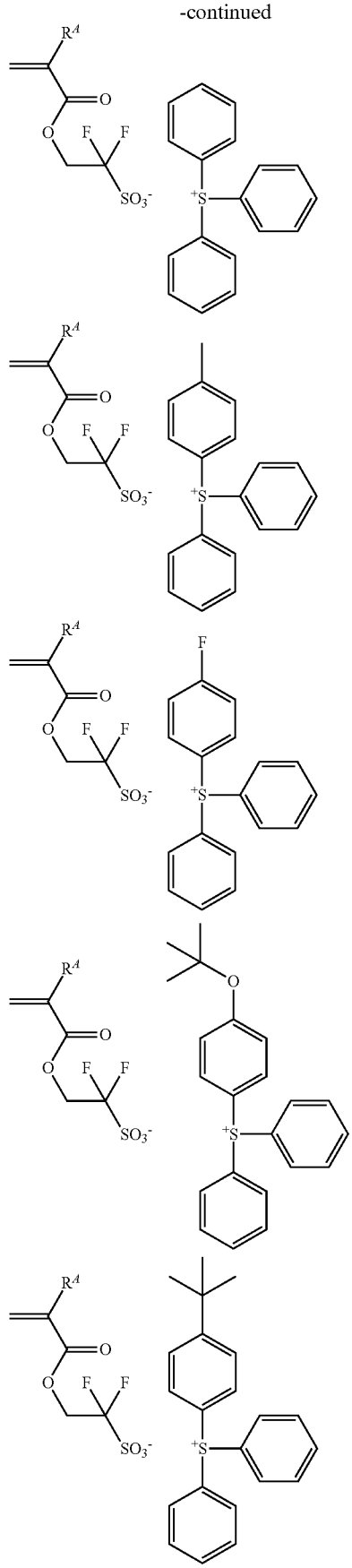
92
-continued
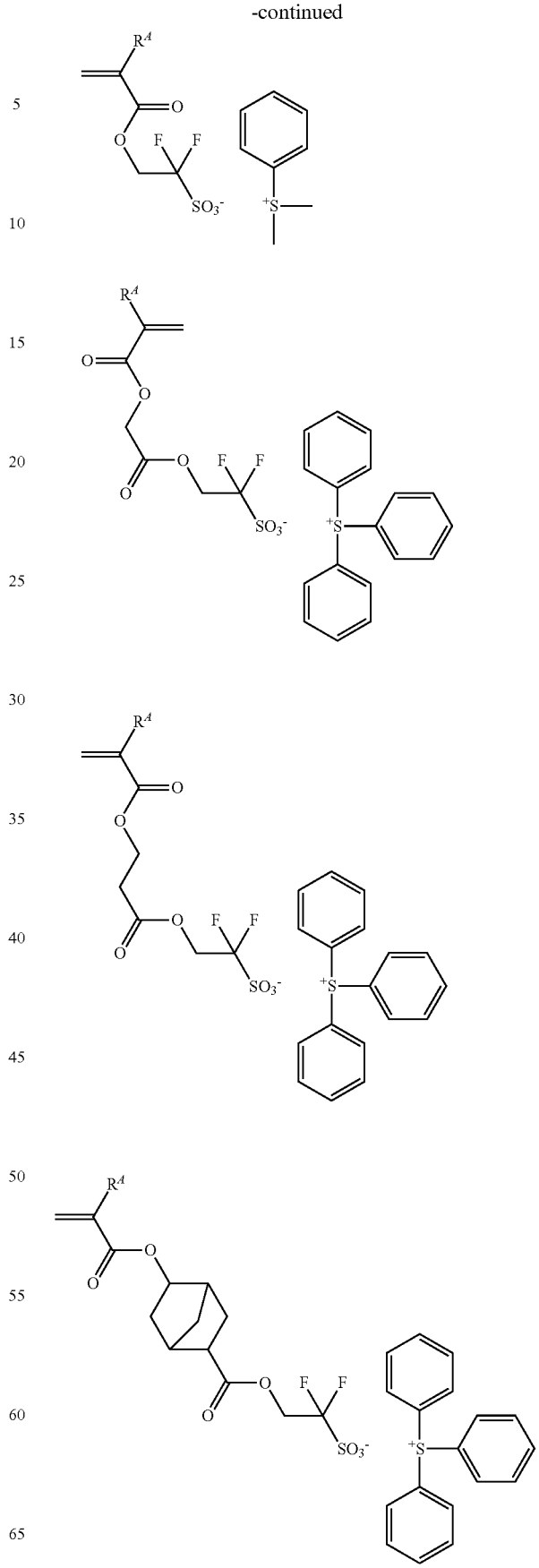

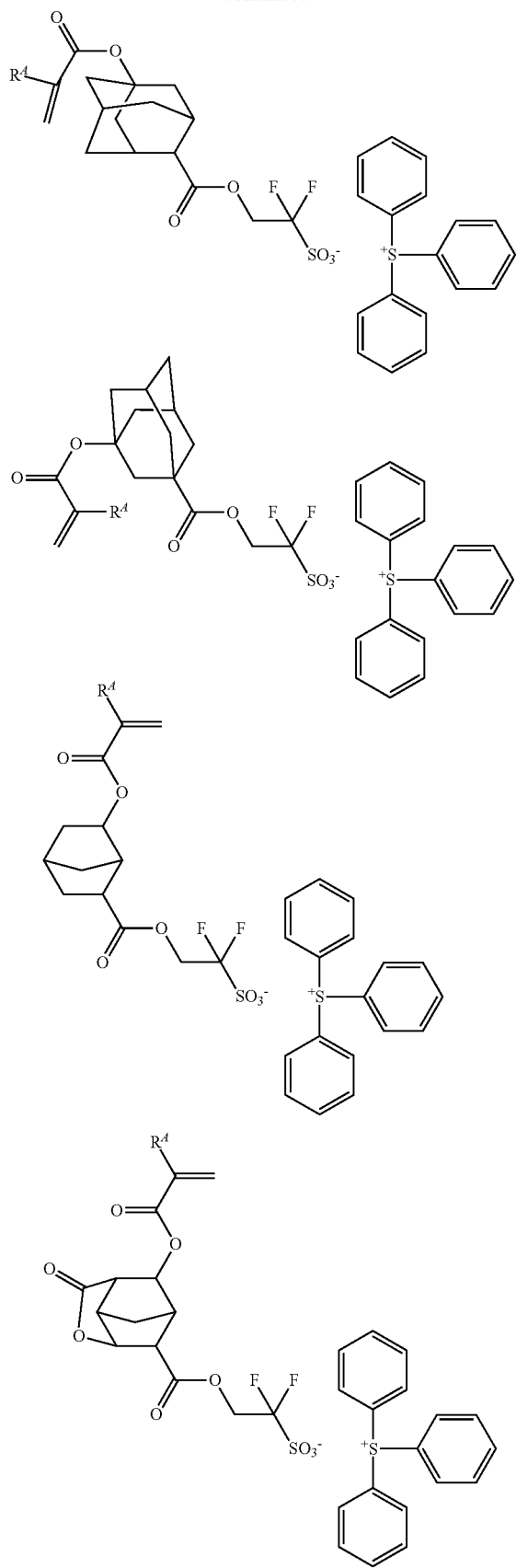
Examples of the monomer from which recurring unit (f3) is derived are shown below, but not limited thereto. $R^A$ is as defined above.
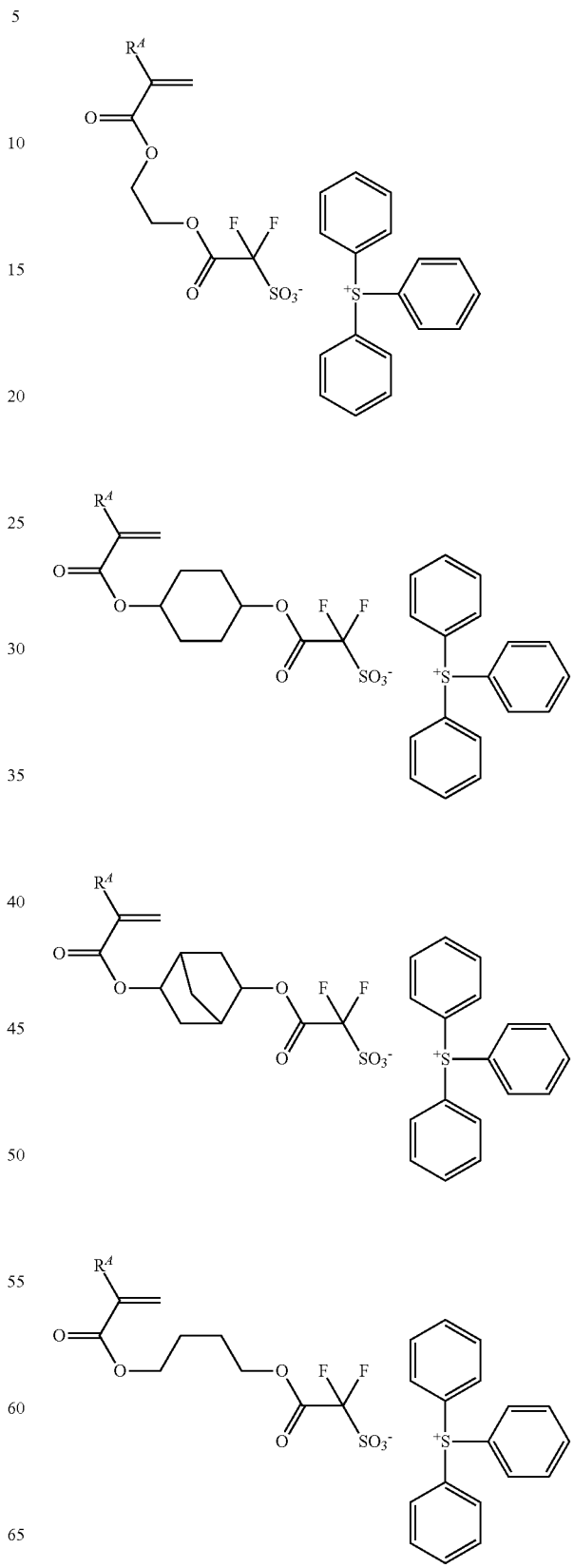

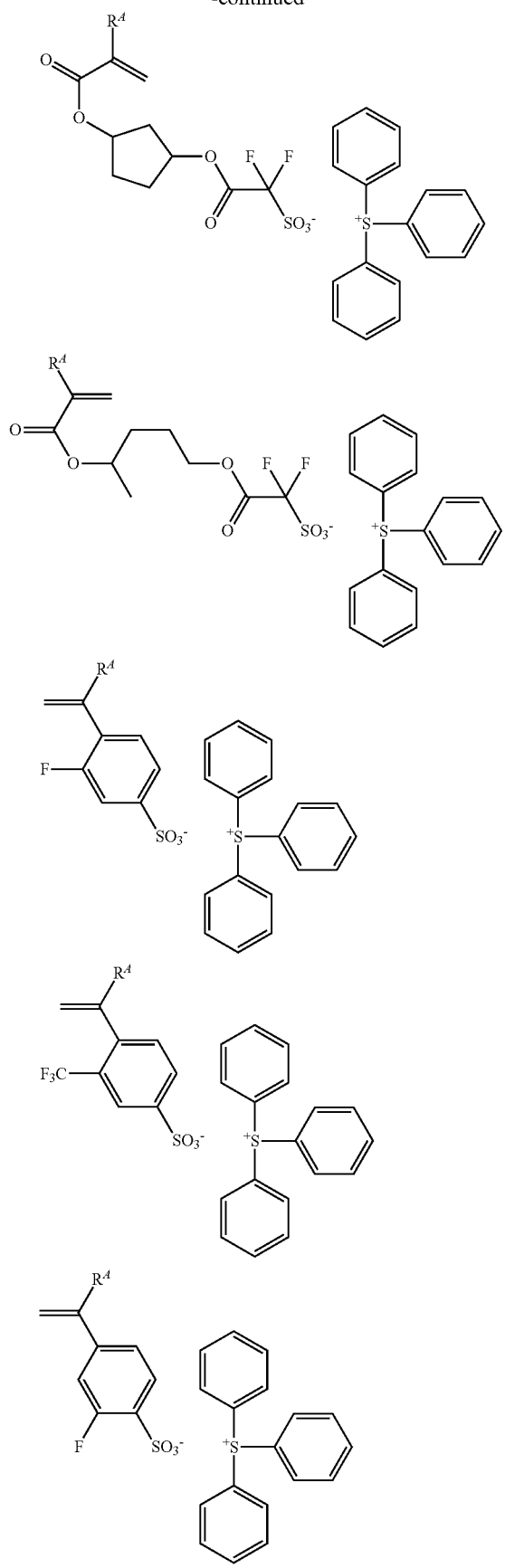
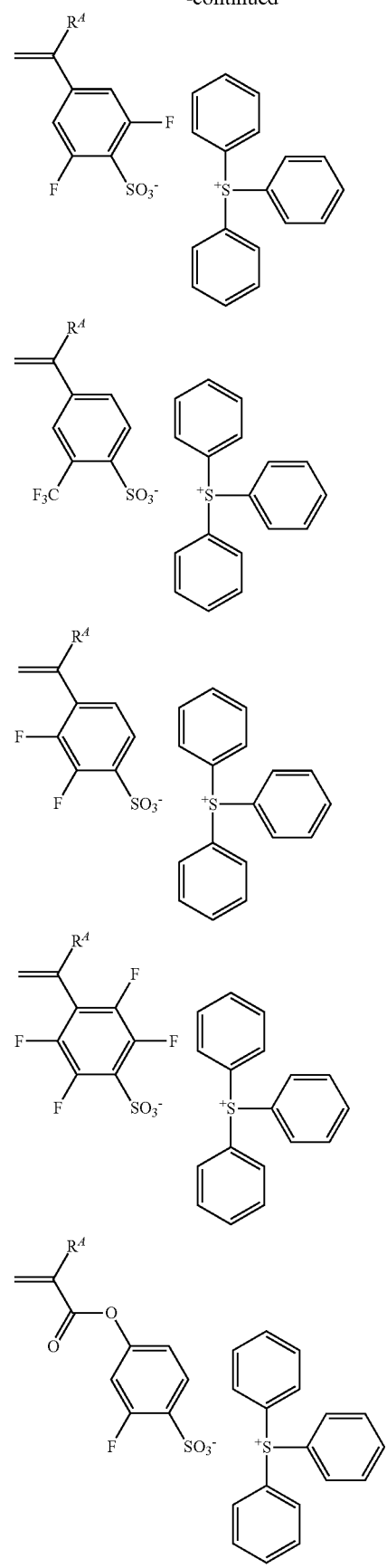

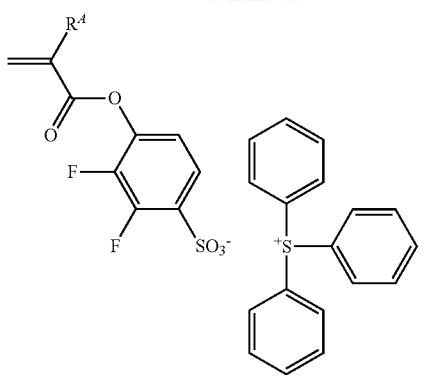
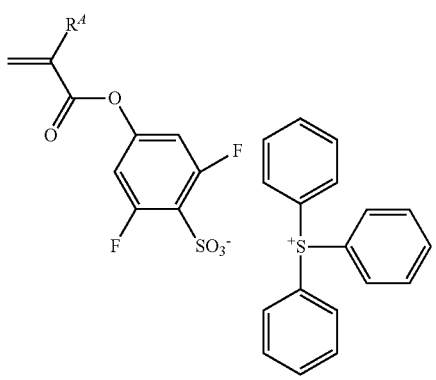
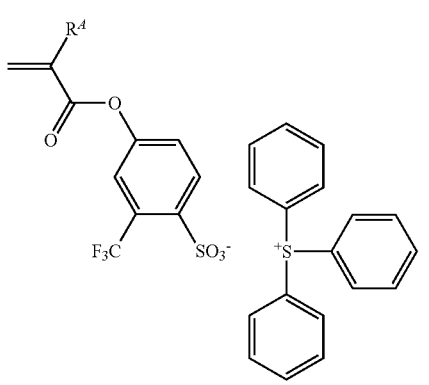
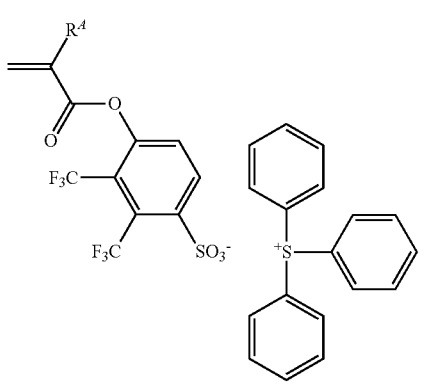
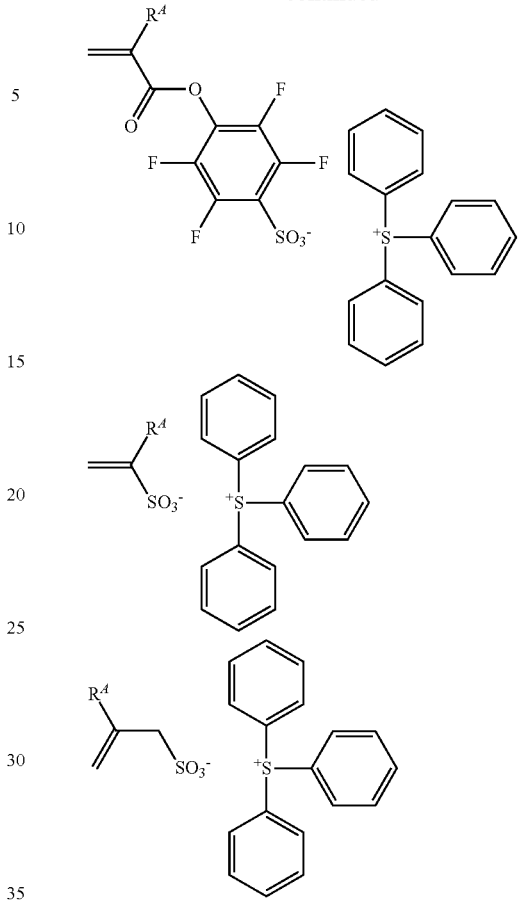

The attachment of an acid generator to the polymer main chain is effective in restraining acid diffusion, thereby preventing a reduction of resolution due to blur by acid diffusion. Also edge roughness is improved since the acid generator is uniformly distributed.

The base polymer for formulating the positive resist composition comprises recurring units (a1) or (a2) having an acid labile group as essential component and additional recurring units (b), (c), (d), (e), and (f) as optional components. A fraction of units (a1), (a2), (b), (c), (d), (e), and (f) is: preferably $0 \leq a1 < 1.0$, $0 \leq a2 < 1.0$, $0 < a1+a2 < 1.0$, $0 \leq b \leq 0.9$, $0 \leq c \leq 0.9$, $0 \leq d\ 0.8$, $0 \leq e \leq 0.8$, and $0 \leq f \leq 0.5$; more preferably $0 \leq a1 \leq 0.9$, $0 \leq a2 \leq 0.9$, $0.1 \leq a1+a2 \leq 0.9$, $0 \leq b \leq 0.8$, $0 \leq c \leq 0.8$, $0 \leq d \leq 0.7$, $0 \leq e \leq 0.7$, and $0 \leq f \leq 0.4$; and even more preferably $0 \leq a1 \leq 0.8$, $0 \leq a2 \leq 0.8$, $0.1 \leq a1+a2 \leq 0.8$, $0 \leq b \leq 0.75$, $0 \leq c \leq 0.75$, $0 \leq d \leq 0.6$, $0 \leq e \leq 0.6$, and $0 \leq f \leq 0.3$. Notably, unit (f) is at least one of units (f1), (f2) and (f3), i.e., $f=f1+f2+f3$, and $a1+a2+b+c+d+e+f=1.0$.

For the base polymer for formulating the negative resist composition, an acid labile group is not necessarily essential. The base polymer comprises recurring units (b), and optionally recurring units (c), (d), (e), and/or (f). A fraction of these units is: preferably $0 < b \leq 1.0$, $0 \leq c \leq 0.9$, $0 \leq d \leq 0.8$, $0 \leq e \leq 0.8$, and $0 \leq f \leq 0.5$; more preferably $0.2 \leq b \leq 1.0$, $0 \leq c \leq 0.8$, $0 \leq d \leq 0.7$, $0 \leq e \leq 0.7$, and $0 \leq f \leq 0.4$; and even more preferably $0.3 \leq b \leq 1.0$, $0 \leq c \leq 0.75$, $0 \leq d \leq 0.6$, $0 \leq e \leq 0.6$, and $0 \leq f \leq 0.3$. Notably, unit (f) is at least one of units (f1), (f2) and (f3), i.e., $f=f1+f2+f3$, and $b+c+d+e+f=1.0$.

The base polymer may be synthesized by any desired methods, for example, by dissolving one or more monomers selected from the monomers corresponding to the foregoing recurring units in an organic solvent, adding a radical polymerization initiator thereto, and heating for polymerization. Examples of the organic solvent which can be used for polymerization include toluene, benzene, tetrahydrofuran, diethyl ether, and dioxane. Examples of the polymerization initiator used herein include 2,2'-azobisisobutyronitrile (AIBN), 2,2'-azobis(2,4-dimethylvaleronitrile), dimethyl 2,2-azobis(2-methylpropionate), benzoyl peroxide, and lauroyl peroxide. Preferably the system is heated at 50 to 80° C. for polymerization to take place. The reaction time is 2 to 100 hours, preferably 5 to 20 hours.

When hydroxystyrene or hydroxyvinylnaphthalene is copolymerized, an alternative method is possible. Specifically, acetoxystyrene or acetoxyvinylnaphthalene is used instead of hydroxystyrene or hydroxyvinylnaphthalene, and after polymerization, the acetoxy group is deprotected by alkaline hydrolysis, for thereby converting the polymer product to hydroxystyrene or hydroxyvinylnaphthalene. For alkaline hydrolysis, a base such as aqueous ammonia or triethylamine may be used. Preferably the reaction temperature is −20° C. to 100° C., more preferably 0° C. to 60° C., and the reaction time is 0.2 to 100 hours, more preferably 0.5 to 20 hours.

The base polymer should preferably have a weight average molecular weight (Mw) in the range of 1,000 to 500,000, and more preferably 2,000 to 30,000, as measured by GPC versus polystyrene standards using tetrahydrofuran (THF) solvent. With too low a Mw, the resist composition may become less heat resistant. A polymer with too high a Mw may lose alkaline solubility and give rise to a footing phenomenon after pattern formation.

If a base polymer has a wide molecular weight distribution or dispersity (Mw/Mn), which indicates the presence of lower and higher molecular weight polymer fractions, there is a possibility that foreign matter is left on the pattern or the pattern profile is degraded. The influences of molecular weight and dispersity become stronger as the pattern rule becomes finer. Therefore, the base polymer should preferably have a narrow dispersity (Mw/Mn) of 1.0 to 2.0, especially 1.0 to 1.5, in order to provide a resist composition suitable for micropatterning to a small feature size.

It is understood that a blend of two or more polymers which differ in compositional ratio, Mw or Mw/Mn is acceptable.

Quencher

To the resist composition, a quencher may be added. The quencher is typically selected from conventional basic compounds. Conventional basic compounds include primary, secondary, and tertiary aliphatic amines, mixed amines, aromatic amines, heterocyclic amines, nitrogen-containing compounds with carboxyl group, nitrogen-containing compounds with sulfonyl group, nitrogen-containing compounds with hydroxyl group, nitrogen-containing compounds with hydroxyphenyl group, alcoholic nitrogen-containing compounds, amide derivatives, imide derivatives, and carbamate derivatives. Also included are primary, secondary, and tertiary amine compounds, specifically amine compounds having a hydroxyl, ether, ester, lactone ring, cyano, or sulfonic acid ester group as described in JP-A 2008-111103, paragraphs [0146]-[0164], and compounds having a carbamate group as described in JP 3790649. Addition of a basic compound may be effective for further suppressing the diffusion rate of acid in the resist film or correcting the pattern profile.

Onium salts such as sulfonium salts, iodonium salts and ammonium salts of sulfonic acids which are not fluorinated at α-position as described in U.S. Pat. No. 8,795,942 (JP-A 2008-158339) may also be used as the quencher. While an α-fluorinated sulfonic acid, imide acid, and methide acid are necessary to deprotect the acid labile group of carboxylic acid ester, an α-non-fluorinated sulfonic acid is released by salt exchange with an α-non-fluorinated onium salt. An α-non-fluorinated sulfonic acid functions as a quencher because it does not induce deprotection reaction.

Also useful are quenchers of polymer type as described in U.S. Pat. No. 7,598,016 (JP-A 2008-239918). The polymeric quencher segregates at the resist surface after coating and thus enhances the rectangularity of resist pattern. When a protective film is applied as is often the case in the immersion lithography, the polymeric quencher is also effective for preventing a film thickness loss of resist pattern or rounding of pattern top.

Also useful as the quencher is an onium salt of carboxylic acid having the formula (1):

wherein $R^{101}$ is a $C_1$-$C_{40}$ straight, branched or cyclic monovalent hydrocarbon group which may contain a heteroatom, and $M_A^+$ is an onium ion such as sulfonium, iodonium or ammonium ion.

The anion moiety in the carboxylic acid onium salt is preferably selected from those having the formula (2).

Herein $R^{102}$ and $R^{103}$ are each independently hydrogen, fluorine or trifluoromethyl, $R^{104}$ is hydrogen, hydroxyl, a $C_1$-$C_{35}$ straight, branched or cyclic monovalent hydrocarbon group which may contain a heteroatom, or a substituted or unsubstituted $C_6$-$C_{30}$ aryl group.

Examples of the carboxylic acid onium salt are given below, but not limited thereto.

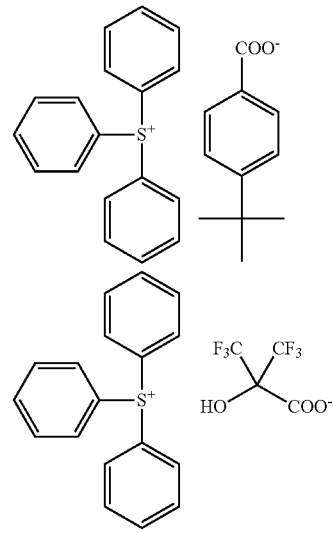

101
-continued
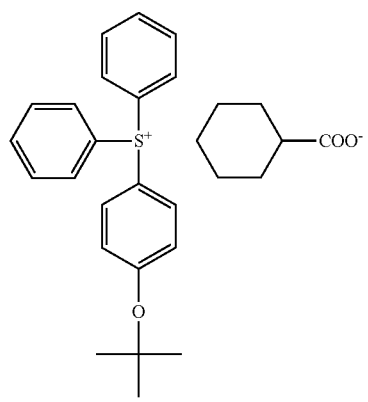
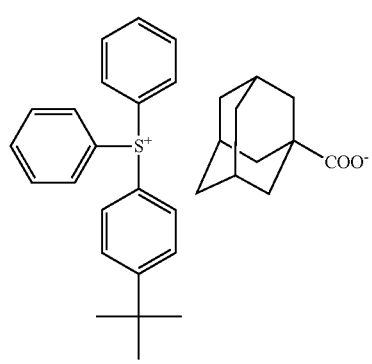
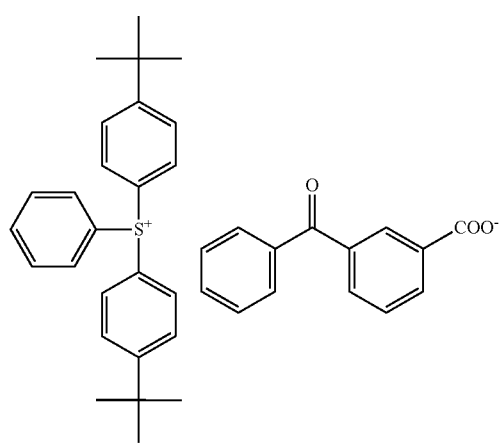
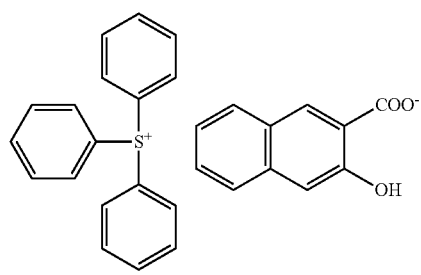
102
-continued
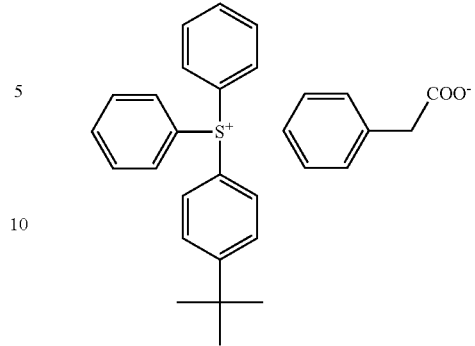
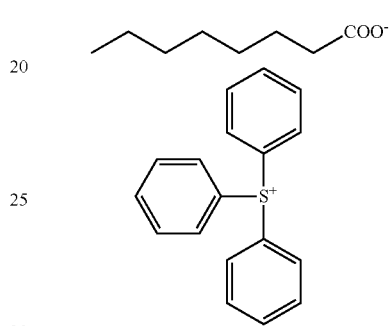
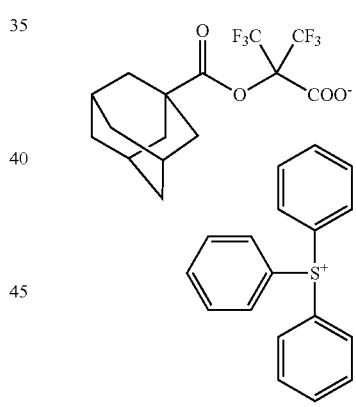
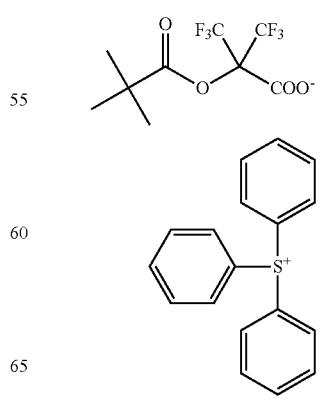

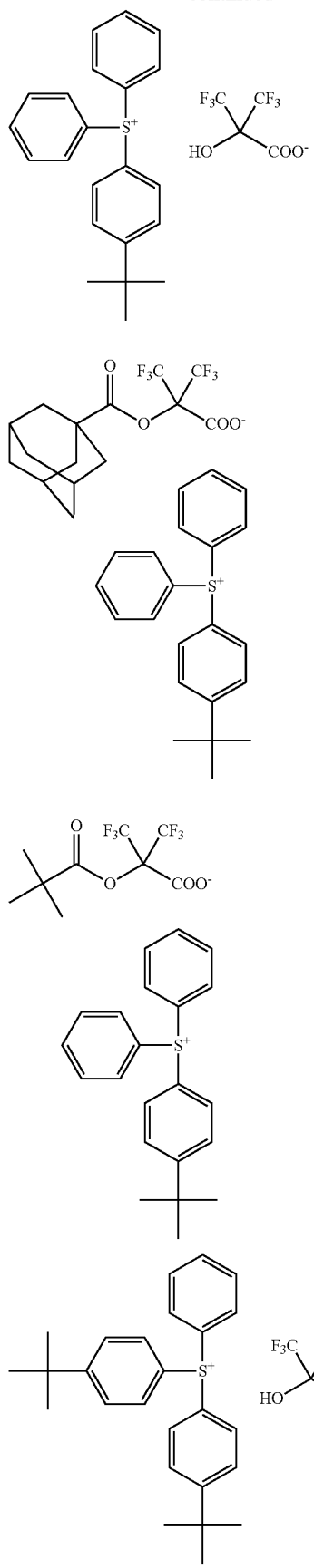
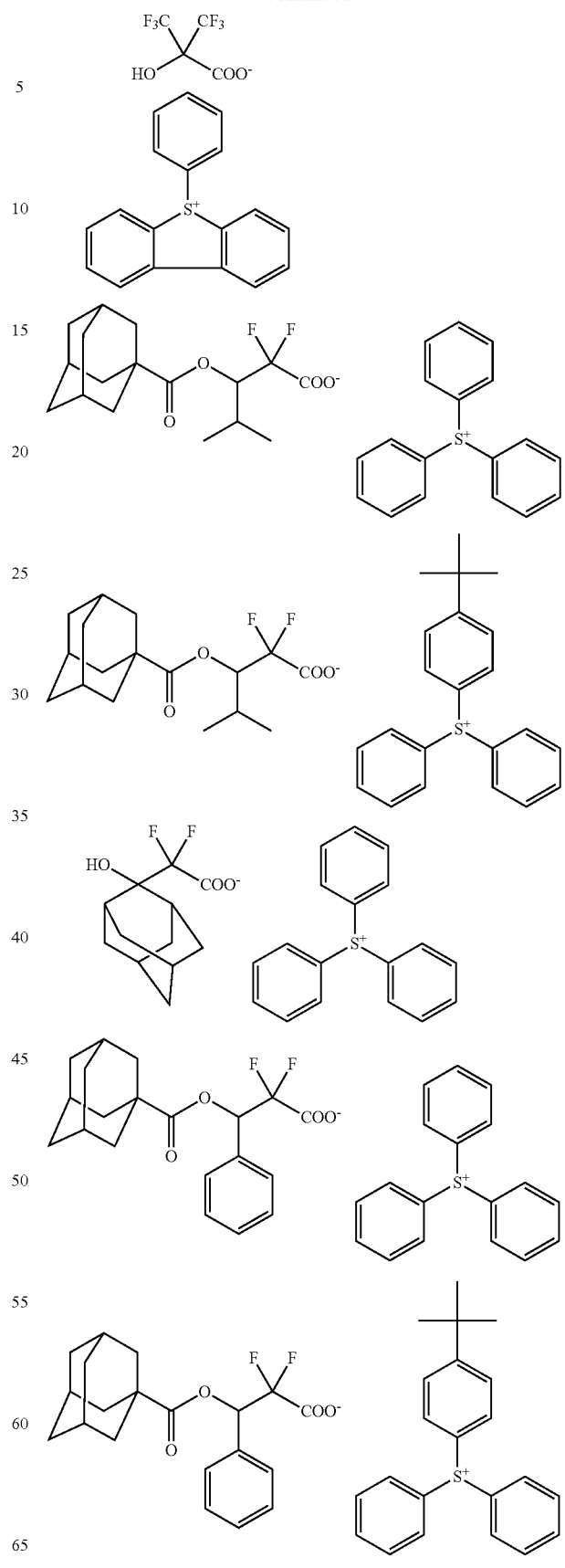

-continued
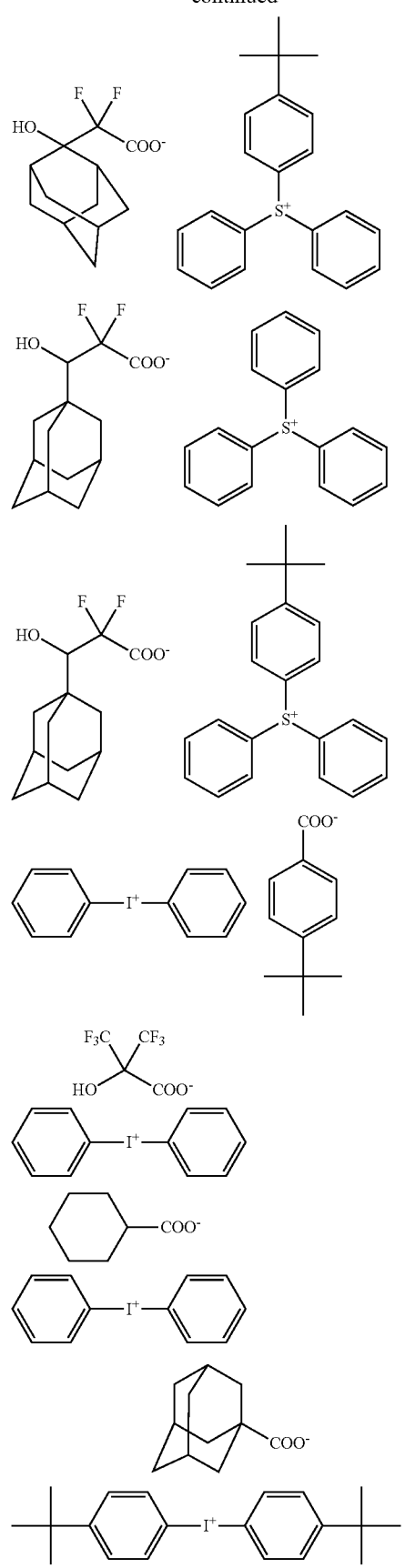
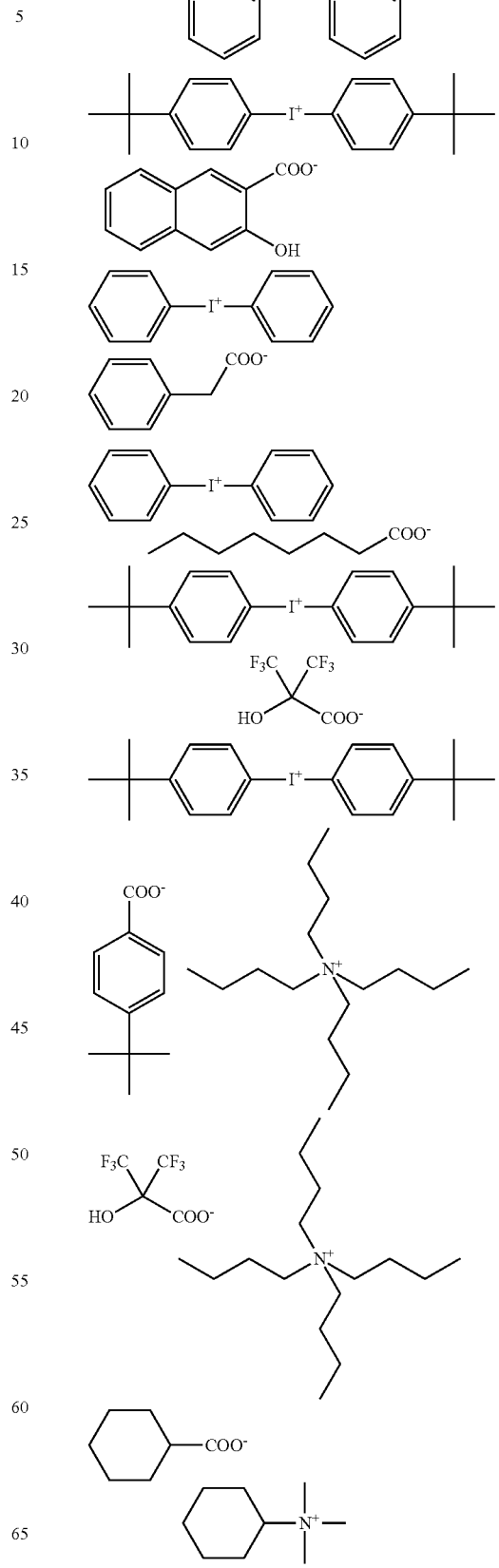

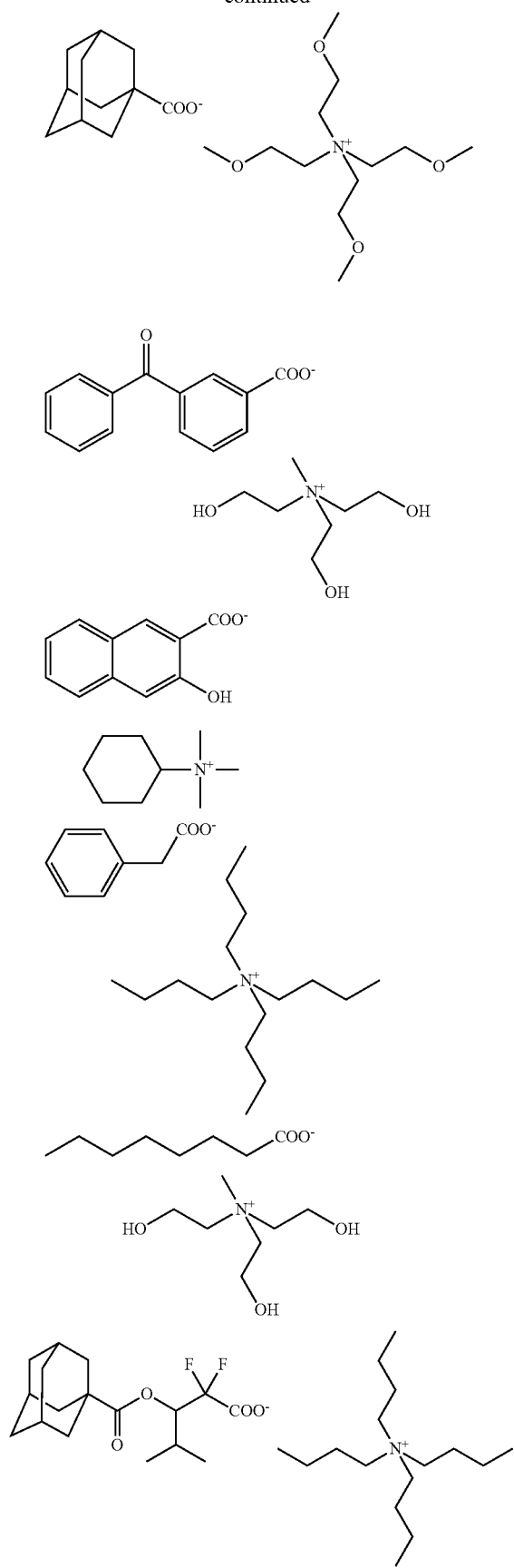

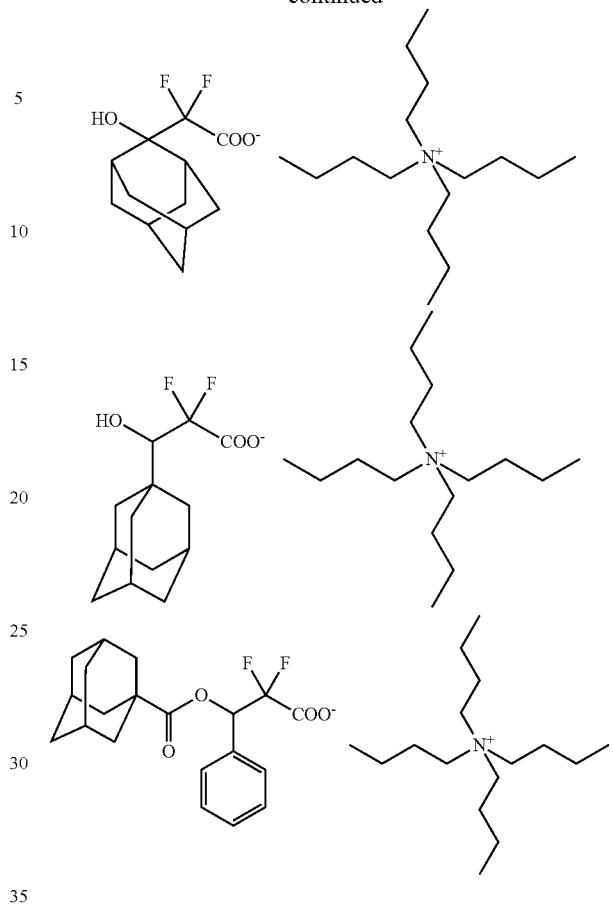

When the resist composition contains a quencher, the quencher is preferably added in an amount of 0.1 to 20 parts, more preferably 0.2 to 10 parts by weight per 100 parts by weight of the base polymer.

Other Components

With the foregoing components, other components such as an organic solvent, surfactant, dissolution inhibitor, and crosslinker may be blended in any desired combination to formulate a chemically amplified positive or negative resist composition. This positive or negative resist composition has a very high sensitivity in that the dissolution rate in developer of the base polymer in exposed areas is accelerated by catalytic reaction. In addition, the resist film has a high dissolution contrast, resolution, exposure latitude, and process adaptability, and provides a good pattern profile after exposure, and minimal proximity bias because of restrained acid diffusion. By virtue of these advantages, the composition is fully useful in commercial application and suited as a pattern-forming material for the fabrication of VLSIs. Particularly when a chemically amplified positive resist composition capable of utilizing acid catalyzed reaction is formulated, the composition has a higher sensitivity and is further improved in the properties described above.

To the resist composition, an acid generator other than the sulfonium salt having formula (A-1) or iodonium salt having formula (A-2) may be added. The other acid generator is typically a compound (PAG) capable of generating an acid upon exposure to actinic ray or radiation. Although the PAG used herein may be any compound capable of generating an acid upon exposure to high-energy radiation, those compounds capable of generating sulfonic acid, imide acid (imidic acid) or methide acid are preferred. Suitable PAGs include sulfonium salts, iodonium salts, sulfonyldiazomethane, N-sulfonyloxyimide, and oxime-O-sulfonate acid generators. Exemplary PAGs are described in JP-A 2008-111103, paragraphs [0122]-[0142] (U.S. Pat. No. 7,537,880). The other acid generator is preferably added in an amount of 0 to 200 parts, and more preferably 0.1 to 100 parts by weight per 100 parts by weight of the base polymer.

In the case of positive resist compositions, inclusion of a dissolution inhibitor may lead to an increased difference in dissolution rate between exposed and unexposed areas and a further improvement in resolution. In the case of negative resist compositions, a negative pattern may be formed by adding a crosslinker to reduce the dissolution rate of exposed area.

Examples of the organic solvent used herein are described in JP-A 2008-111103, paragraphs [0144]-[0145] (U.S. Pat. No. 7,537,880). Exemplary solvents include ketones such as cyclohexanone, cyclopentanone and methyl-2-n-pentyl ketone; alcohols such as 3-methoxybutanol, 3-methyl-3-methoxybutanol, 1-methoxy-2-propanol, and 1-ethoxy-2-propanol; ethers such as propylene glycol monomethyl ether, ethylene glycol monomethyl ether, propylene glycol monoethyl ether, ethylene glycol monoethyl ether, propylene glycol dimethyl ether, and diethylene glycol dimethyl ether; esters such as propylene glycol monomethyl ether acetate (PGMEA), propylene glycol monoethyl ether acetate, ethyl lactate, ethyl pyruvate, butyl acetate, methyl 3-methoxypropionate, ethyl 3-ethoxypropionate, t-butyl acetate, t-butyl propionate, and propylene glycol mono-t-butyl ether acetate; and lactones such as γ-butyrolactone, which may be used alone or in admixture.

The organic solvent is preferably added in an amount of 100 to 10,000 parts, and more preferably 200 to 8,000 parts by weight per 100 parts by weight of the base polymer.

Exemplary surfactants are described in JP-A 2008-111103, paragraphs [0165]-[0166]. Inclusion of a surfactant may improve or control the coating characteristics of the resist composition. The surfactant is preferably added in an amount of 0.0001 to 10 parts by weight per 100 parts by weight of the base polymer.

The dissolution inhibitor which can be used herein is a compound having at least two phenolic hydroxyl groups on the molecule, in which an average of from 0 to 100 mol % of all the hydrogen atoms on the phenolic hydroxyl groups are replaced by acid labile groups or a compound having at least one carboxyl group on the molecule, in which an average of 50 to 100 mol % of all the hydrogen atoms on the carboxyl groups are replaced by acid labile groups, both the compounds having a molecular weight of 100 to 1,000, and preferably 150 to 800. Typical are bisphenol A, trisphenol, phenolphthalein, cresol novolac, naphthalenecarboxylic acid, adamantanecarboxylic acid, and cholic acid derivatives in which the hydrogen atom on the hydroxyl or carboxyl group is replaced by an acid labile group, as described in U.S. Pat. No. 7,771,914 (JP-A 2008-122932, paragraphs [0155]-[0178]).

In the positive resist composition, the dissolution inhibitor is preferably added in an amount of 0 to 50 parts, more preferably 5 to 40 parts by weight per 100 parts by weight of the base polymer.

Suitable crosslinkers which can be used herein include epoxy compounds, melamine compounds, guanamine compounds, glycoluril compounds and urea compounds having substituted thereon at least one group selected from among methylol, alkoxymethyl and acyloxymethyl groups, isocyanate compounds, azide compounds, and compounds having a double bond such as an alkenyl ether group. These compounds may be used as an additive or introduced into a polymer side chain as a pendant. Hydroxy-containing compounds may also be used as the crosslinker.

Of the foregoing crosslinkers, examples of suitable epoxy compounds include tris(2,3-epoxypropyl) isocyanurate, trimethylolmethane triglycidyl ether, trimethylolpropane triglycidyl ether, and triethylolethane triglycidyl ether. Examples of the melamine compound include hexamethylol melamine, hexamethoxymethyl melamine, hexamethylol melamine compounds having 1 to 6 methylol groups methoxymethylated and mixtures thereof, hexamethoxyethyl melamine, hexaacyloxymethyl melamine, hexamethylol melamine compounds having 1 to 6 methylol groups acyloxymethylated and mixtures thereof. Examples of the guanamine compound include tetramethylol guanamine, tetramethoxymethyl guanamine, tetramethylol guanamine compounds having 1 to 4 methylol groups methoxymethylated and mixtures thereof, tetramethoxyethyl guanamine, tetraacyloxyguanamine, tetramethylol guanamine compounds having 1 to 4 methylol groups acyloxymethylated and mixtures thereof. Examples of the glycoluril compound include tetramethylol glycoluril, tetramethoxyglycoluril, tetramethoxymethyl glycoluril, tetramethylol glycoluril compounds having 1 to 4 methylol groups methoxymethylated and mixtures thereof, tetramethylol glycoluril compounds having 1 to 4 methylol groups acyloxymethylated and mixtures thereof. Examples of the urea compound include tetramethylol urea, tetramethoxymethyl urea, tetramethylol urea compounds having 1 to 4 methylol groups methoxymethylated and mixtures thereof, and tetramethoxyethyl urea.

Suitable isocyanate compounds include tolylene diisocyanate, diphenylmethane diisocyanate, hexamethylene diisocyanate and cyclohexane diisocyanate. Suitable azide compounds include 1,1'-biphenyl-4,4'-bisazide, 4,4'-methylidenebisazide, and 4,4'-oxybisazide. Examples of the alkenyl ether group-containing compound include ethylene glycol divinyl ether, triethylene glycol divinyl ether, 1,2-propanediol divinyl ether, 1,4-butanediol divinyl ether, tetramethylene glycol divinyl ether, neopentyl glycol divinyl ether, trimethylol propane trivinyl ether, hexanediol divinyl ether, 1,4-cyclohexanediol divinyl ether, pentaerythritol trivinyl ether, pentaerythritol tetravinyl ether, sorbitol tetravinyl ether, sorbitol pentavinyl ether, and trimethylol propane trivinyl ether.

In the negative resist composition, the crosslinker is preferably added in an amount of 0.1 to 50 parts, more preferably 1 to 40 parts by weight per 100 parts by weight of the base polymer.

To the resist composition, a polymeric additive (or water repellency improver) may also be added for improving the water repellency on surface of a resist film as spin coated. The water repellency improver may be used in the topcoatless immersion lithography. Suitable water repellency improvers include polymers having a fluoroalkyl group and polymers having a specific structure with a 1,1,1,3,3,3-hexafluoro-2-propanol residue and are described in JP-A 2007-297590 and JP-A 2008-111103, for example. The water repellency improver to be added to the resist composition should be soluble in the organic solvent as the developer. The water repellency improver of specific structure with a 1,1,1,3,3,3-hexafluoro-2-propanol residue is well soluble in the developer. A polymer having an amino group or amine salt copolymerized as recurring units may serve as the water repellent additive and is effective for preventing evaporation of acid during PEB, thus preventing any hole pattern opening failure after development. An appropriate amount of the water repellency improver is 0 to 20 parts, preferably 0.5 to 10 parts by weight per 100 parts by weight of the base polymer.

Also, an acetylene alcohol may be blended in the resist composition. Suitable acetylene alcohols are described in JP-A 2008-122932, paragraphs [0179]-[0182]. An appropriate amount of the acetylene alcohol blended is 0 to 5 parts by weight per 100 parts by weight of the base polymer.

Process

The resist composition is used in the fabrication of various integrated circuits. Pattern formation using the resist composition may be performed by well-known lithography processes. The process generally involves coating, prebaking, exposure, and development. If necessary, any additional steps may be added.

For example, the positive resist composition is first applied onto a substrate on which an integrated circuit is to be formed (e.g., Si, $SiO_2$, SiN, SiON, TiN, WSi, BPSG, SOG, or organic antireflective coating) or a substrate on which a mask circuit is to be formed (e.g., Cr, CrO, CrON, $MoSi_2$, or $SiO_2$) by a suitable coating technique such as spin coating, roll coating, flow coating, dipping, spraying or doctor coating. The coating is prebaked on a hotplate at a temperature of 60 to 150° C. for 10 seconds to 30 minutes, preferably 80 to 120° C. for 30 seconds to 20 minutes. The resulting resist film is generally 0.01 to 2.0 m thick.

The resist film is then exposed to a desired pattern of high-energy radiation such as UV, deep-UV, EB, EUV, x-ray, soft x-ray, excimer laser light, γ-ray or synchrotron radiation, directly or through a mask having the desired pattern. The exposure dose is preferably about 1 to 200 $mJ/cm^2$, more preferably about 10 to 100 $mJ/cm^2$, or about 0.1 to 100 $\mu C/cm^2$, more preferably about 0.5 to 50 $C/cm^2$. The resist film is further baked (PEB) on a hotplate at 60 to 150° C. for 10 seconds to 30 minutes, preferably 80 to 120° C. for 30 seconds to 20 minutes.

Thereafter the resist film is developed with a developer in the form of an aqueous base solution for 3 seconds to 3 minutes, preferably 5 seconds to 2 minutes by conventional techniques such as dip, puddle and spray techniques. A typical developer is a 0.1 to 10 wt %, preferably 2 to 5 wt % aqueous solution of tetramethylammonium hydroxide (TMAH), tetraethylammonium hydroxide (TEAH), tetrapropylammonium hydroxide (TPAH), or tetrabutylammonium hydroxide (TBAH). The resist film in the exposed area is dissolved in the developer whereas the resist film in the unexposed area is not dissolved. In this way, the desired positive pattern is formed on the substrate. Inversely in the case of negative resist, the exposed area of resist film is insolubilized and the unexposed area is dissolved in the developer. It is appreciated that the resist composition of the invention is best suited for micro-patterning using such high-energy radiation as KrF and ArF excimer laser, EB, EUV, x-ray, soft x-ray, γ-ray and synchrotron radiation.

In an alternative embodiment, a negative pattern may be formed via organic solvent development using a positive resist composition comprising a base polymer having an acid labile group. The developer used herein is preferably selected from among 2-octanone, 2-nonanone, 2-heptanone, 3-heptanone, 4-heptanone, 2-hexanone, 3-hexanone, diisobutyl ketone, methylcyclohexanone, acetophenone, methylacetophenone, propyl acetate, butyl acetate, isobutyl acetate, pentyl acetate, butenyl acetate, isopentyl acetate, propyl formate, butyl formate, isobutyl formate, pentyl formate, isopentyl formate, methyl valerate, methyl pentenoate, methyl crotonate, ethyl crotonate, methyl propionate, ethyl propionate, ethyl 3-ethoxypropionate, methyl lactate, ethyl lactate, propyl lactate, butyl lactate, isobutyl lactate, pentyl lactate, isopentyl lactate, methyl 2-hydroxyisobutyrate, ethyl 2-hydroxyisobutyrate, methyl benzoate, ethyl benzoate, phenyl acetate, benzyl acetate, methyl phenylacetate, benzyl formate, phenylethyl formate, methyl 3-phenylpropionate, benzyl propionate, ethyl phenylacetate, and 2-phenylethyl acetate, and mixtures thereof.

At the end of development, the resist film is rinsed. As the rinsing liquid, a solvent which is miscible with the developer and does not dissolve the resist film is preferred. Suitable solvents include alcohols of 3 to 10 carbon atoms, ether compounds of 8 to 12 carbon atoms, alkanes, alkenes, and alkynes of 6 to 12 carbon atoms, and aromatic solvents. Specifically, suitable alcohols of 3 to 10 carbon atoms include n-propyl alcohol, isopropyl alcohol, 1-butyl alcohol, 2-butyl alcohol, isobutyl alcohol, t-butyl alcohol, 1-pentanol, 2-pentanol, 3-pentanol, t-pentyl alcohol, neopentyl alcohol, 2-methyl-1-butanol, 3-methyl-1-butanol, 3-methyl-3-pentanol, cyclopentanol, 1-hexanol, 2-hexanol, 3-hexanol, 2,3-dimethyl-2-butanol, 3,3-dimethyl-1-butanol, 3,3-dimethyl-2-butanol, 2-ethyl-1-butanol, 2-methyl-1-pentanol, 2-methyl-2-pentanol, 2-methyl-3-pentanol, 3-methyl-1-pentanol, 3-methyl-2-pentanol, 3-methyl-3-pentanol, 4-methyl-1-pentanol, 4-methyl-2-pentanol, 4-methyl-3-pentanol, cyclohexanol, and 1-octanol. Suitable ether compounds of 8 to 12 carbon atoms include di-n-butyl ether, diisobutyl ether, di-s-butyl ether, di-n-pentyl ether, diisopentyl ether, di-s-pentyl ether, di-t-pentyl ether, and di-n-hexyl ether. Suitable alkanes of 6 to 12 carbon atoms include hexane, heptane, octane, nonane, decane, undecane, dodecane, methylcyclopentane, dimethylcyclopentane, cyclohexane, methylcyclohexane, dimethylcyclohexane, cycloheptane, cyclooctane, and cyclononane. Suitable alkenes of 6 to 12 carbon atoms include hexene, heptene, octene, cyclohexene, methylcyclohexene, dimethylcyclohexene, cycloheptene, and cyclooctene. Suitable alkynes of 6 to 12 carbon atoms include hexyne, heptyne, and octyne. Suitable aromatic solvents include toluene, xylene, ethylbenzene, isopropylbenzene, t-butylbenzene and mesitylene. The solvents may be used alone or in admixture.

Rinsing is effective for minimizing the risks of resist pattern collapse and defect formation. However, rinsing is not essential. If rinsing is omitted, the amount of solvent used may be reduced.

A hole or trench pattern after development may be shrunk by the thermal flow, RELACS® or DSA process. A hole pattern is shrunk by coating a shrink agent thereto, and baking such that the shrink agent may undergo crosslinking at the resist surface as a result of the acid catalyst diffusing from the resist layer during bake, and the shrink agent may attach to the sidewall of the hole pattern. The bake is preferably at a temperature of 70 to 180° C., more preferably 80 to 170° C., for a time of 10 to 300 seconds. The extra shrink agent is stripped and the hole pattern is shrunk.

EXAMPLE

Examples of the invention are given below by way of illustration and not by way of limitation. The abbreviation "pbw" is parts by weight.

Resist compositions of Examples contained acid generators PAG 1 to PAG 12 in the form of sulfonium or iodonium salts which are identified below. PAG 1 to PAG 12 were synthesized by ion exchange between an ammonium salt of fluorobenzenesulfonic acid bonded to iodized benzoic acid providing the anion shown below and a sulfonium or iodonium chloride providing the cation shown below.
-continued
PAG 1
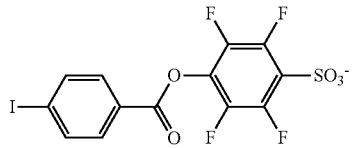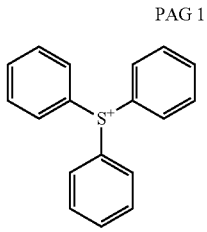
PAG 5
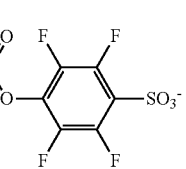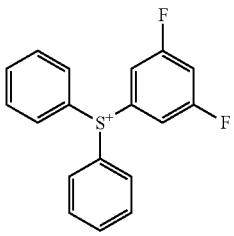
PAG 2
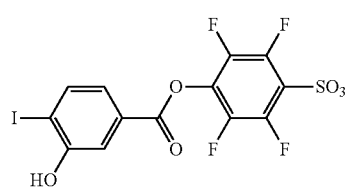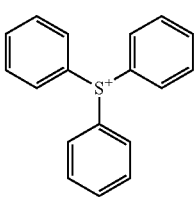
PAG 6
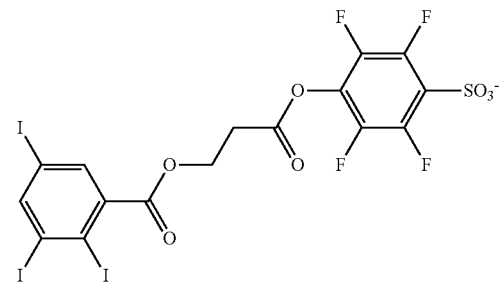
PAG 3
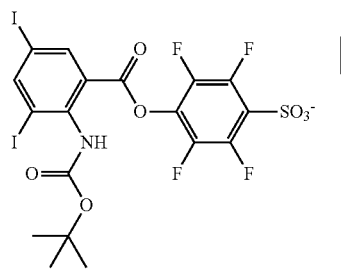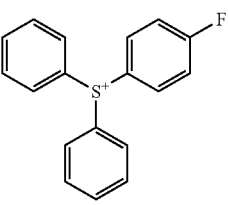
PAG 7
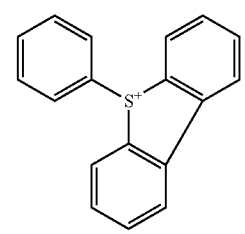
PAG 4
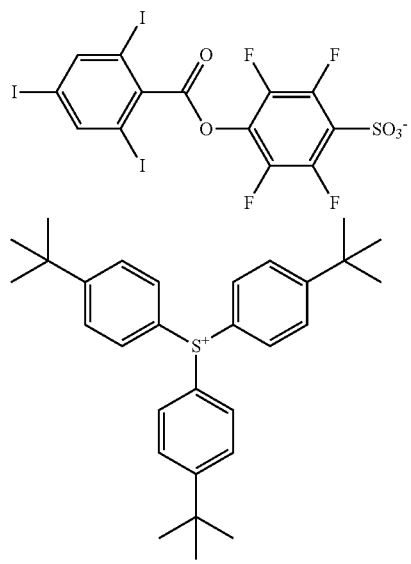
PAG 8
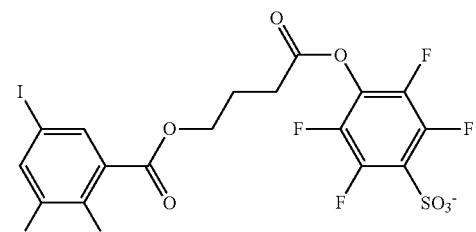
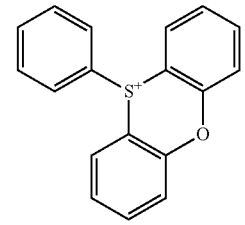
PAG 5
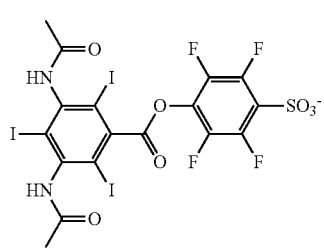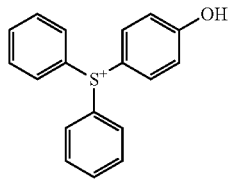
PAG 9
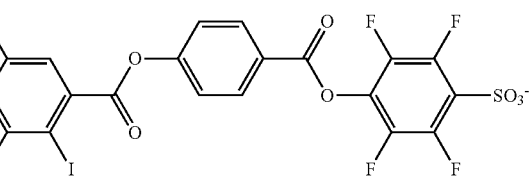

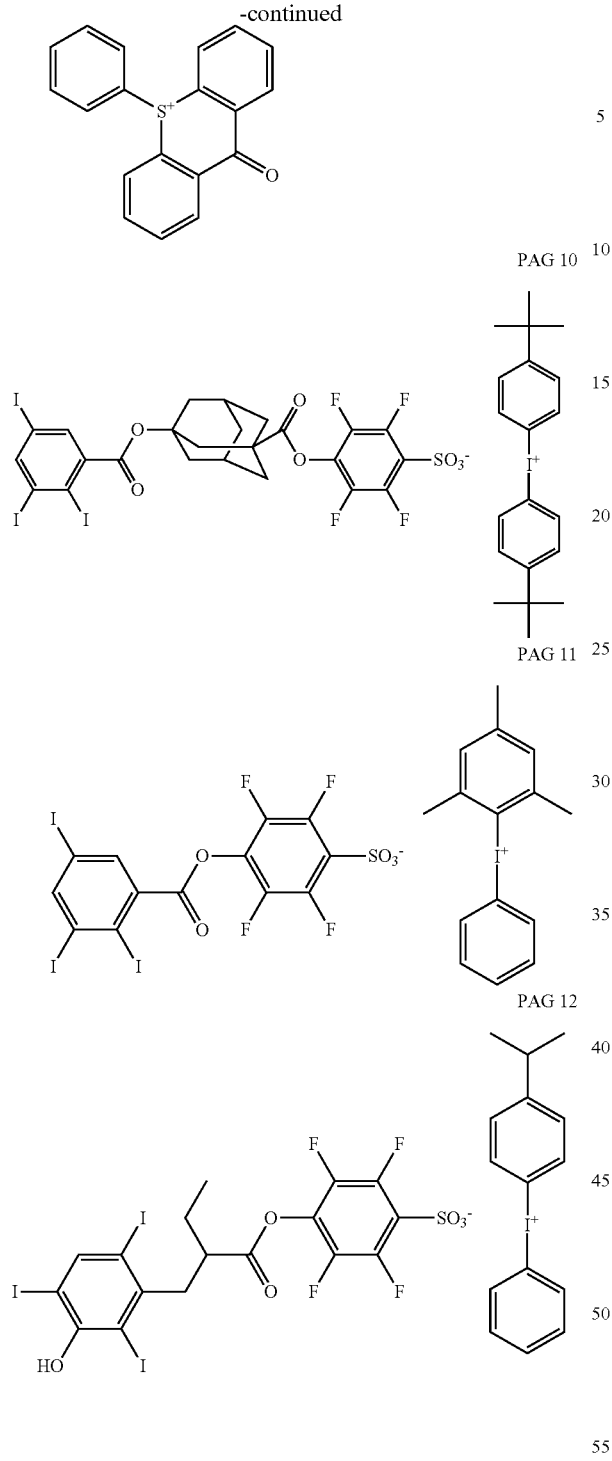

PAG 10

PAG 11

PAG 12

SYNTHESIS EXAMPLE

Synthesis of Base Polymers (Polymers 1 to 3)

Base polymers were prepared by combining suitable monomers, effecting copolymerization reaction thereof in tetrahydrofuran (THF) solvent, pouring the reaction solution into methanol for crystallization, repeatedly washing with hexane, isolation, and drying. The resulting polymers, designated Polymers 1 to 3, were analyzed for composition by $^1$H-NMR spectroscopy, and for Mw and Mw/Mn by GPC versus polystyrene standards using THF solvent.

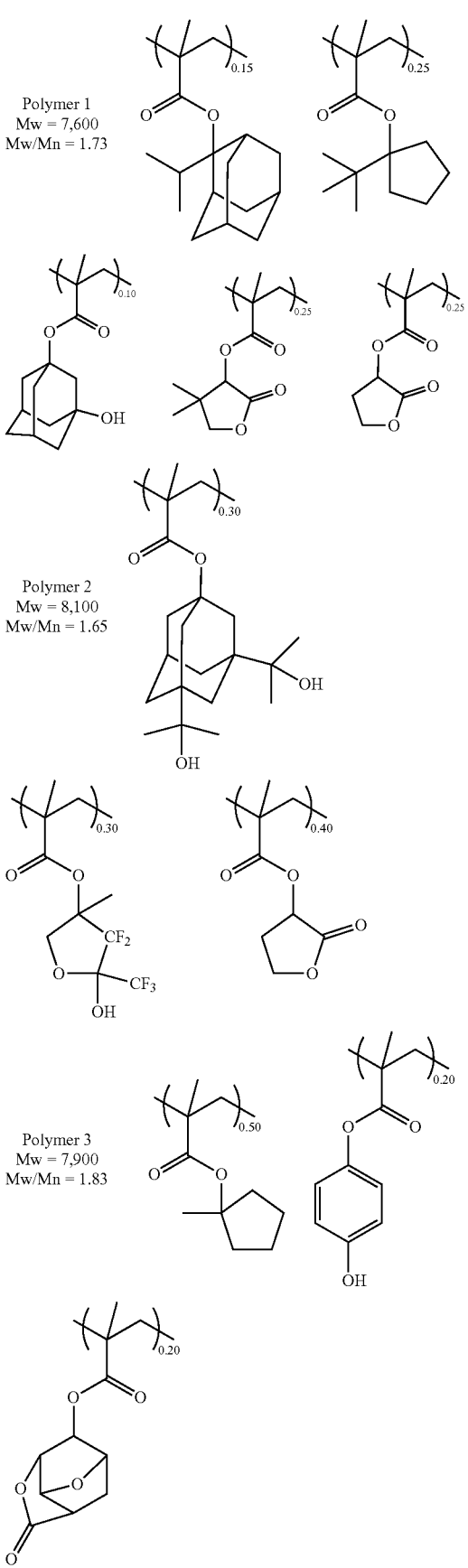

Polymer 1
Mw = 7,600
Mw/Mn = 1.73

Polymer 2
Mw = 8,100
Mw/Mn = 1.65

Polymer 3
Mw = 7,900
Mw/Mn = 1.83

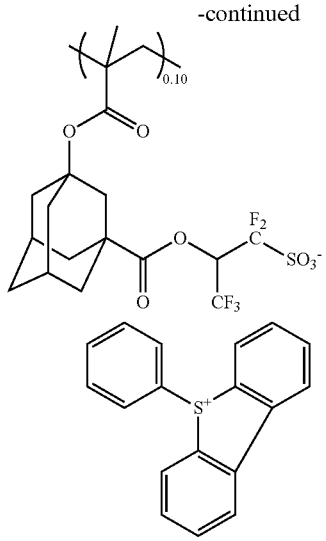

EXAMPLES AND COMPARATIVE EXAMPLES

Resist compositions were prepared by dissolving the polymer and selected components in a solvent in accordance with the recipe shown in Tables 1 and 2, and filtering through a filter having a pore size of 0.2 μm. The solvent contained 100 ppm of surfactant FC-4430 (3M). The components in Tables 1 and 2 are as identified below.

Organic Solvents:
- PGMEA (propylene glycol monomethyl ether acetate)
- GBL (γ-butyrolactone)
- CyH (cyclohexanone)
- PGME (propylene glycol monomethyl ether)
- DAA (diacetone alcohol)

Comparative Acid Generators:
c-PAG 1 to c-PAG 4 of the following structural formulae c-PAG-1

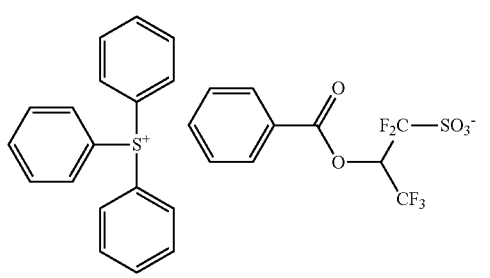

c-PAG-2

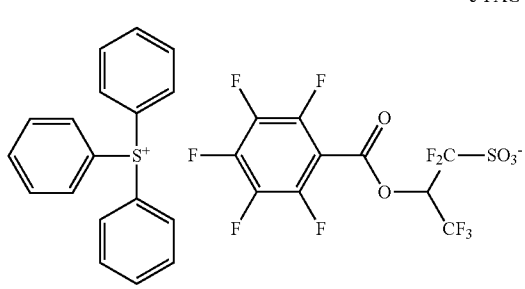

c-PAG-3

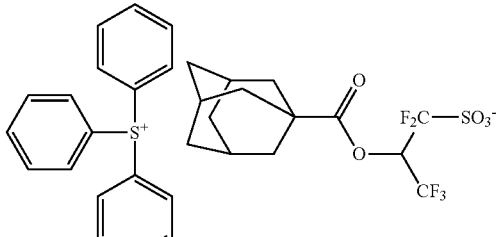

c-PAG-4

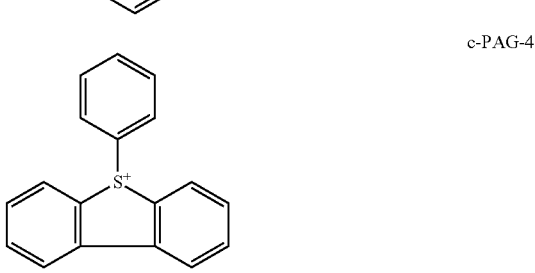

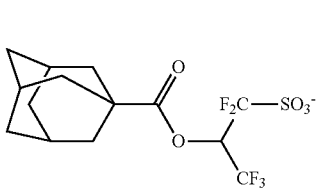

Quenchers 1 to 3 of the following structural formulae

Quencher 1

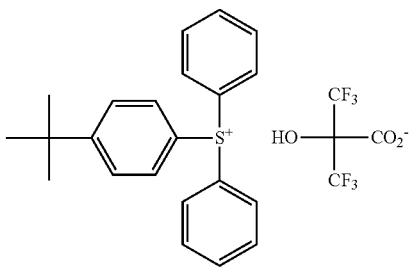

Quencher 2

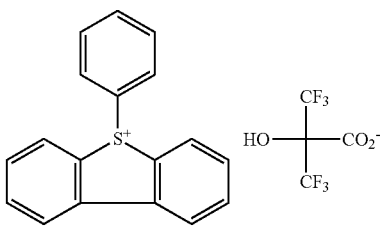

Quencher 3

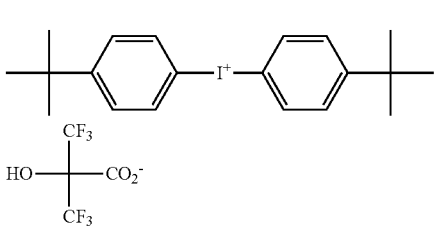

Water-repellent polymers 1 and 2

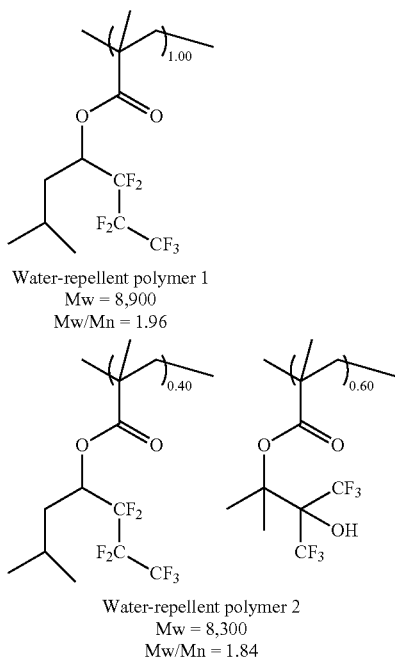

Water-repellent polymer 1
Mw = 8,900
Mw/Mn = 1.96

Water-repellent polymer 2
Mw = 8,300
Mw/Mn = 1.84 content of 80 wt % was deposited to a thickness of 200 nm and a silicon-containing spin-on hard mask SHB-A940 having a silicon content of 43 wt % was deposited thereon to a thickness of 35 nm. On this substrate for trilayer process, each of the resist compositions in Table 1 was spin coated, then baked on a hotplate at 100° C. for 60 seconds to form a resist film of 80 nm thick.

Using an ArF excimer laser scanner NSR-S610C (Nikon Corp., NA 1.30, σ 0.98/0.78, 35° cross-pole illumination, azimuthally polarized illumination), the resist film was exposed through a 6% halftone phase shift mask bearing a pattern having a line of 50 nm and a pitch of 100 nm (on-wafer size) by immersion lithography. Water was used as the immersion liquid. The resist film was baked (PEB) at the temperature shown in Table 1 for 60 seconds. Thereafter, the resist film was developed in n-butyl acetate for 30 seconds in Examples 1-1 to 1-9 and Comparative Examples 1-1 to 1-3 or in 2.38 wt % tetramethylammonium hydroxide (TMAH) aqueous solution in Example 1-10 and Comparative Example 1-4, yielding a negative line-and-space (L/S) pattern having a space of 50 nm and a pitch of 100 nm.

The pattern was observed under a CD-SEM (CG-4000, Hitachi High-Technologies Corp.). The exposure dose capable of resolving a L/S pattern at 1:1 was determined as sensitivity, and edge roughness (LWR) at that dose was measured. The results are shown in Table 1.

TABLE 1

| | | Polymer (pbw) | Acid generator (pbw) | Quencher (pbw) | Water-repellent polymer (pbw) | Organic solvent (pbw) | PEB temp. (° C.) | Sensitivity (mJ/cm$^2$) | LWR (nm) |
|---|---|---|---|---|---|---|---|---|---|
| Example | 1-1 | Polymer 1 (100) | PAG 1 (8.0) | Quencher 1 (4.50) | Water-repellent polymer 1 (4.0) | PGMEA (2,200) GBL (300) | 85 | 21 | 3.0 |
| | 1-2 | Polymer 1 (100) | PAG 2 (8.0) | Quencher 1 (4.50) | Water-repellent polymer 1 (4.0) | PGMEA (2,200) GBL (300) | 85 | 23 | 3.1 |
| | 1-3 | Polymer 1 (100) | PAG 3 (8.0) | Quencher 1 (4.50) | Water-repellent polymer 1 (4.0) | PGMEA (2,200) GBL (300) | 85 | 29 | 3.1 |
| | 1-4 | Polymer 1 (100) | PAG 4 (8.0) | Quencher 1 (4.50) | Water-repellent polymer 1 (4.0) | PGMEA (2,200) GBL (300) | 85 | 28 | 2.9 |
| | 1-5 | Polymer 1 (100) | PAG 5 (8.0) | Quencher 1 (4.50) | Water-repellent polymer 1 (4.0) | PGMEA (2,200) GBL (300) | 85 | 31 | 3.2 |
| | 1-6 | Polymer 1 (100) | PAG 6 (8.0) | Quencher 1 (4.50) | Water-repellent polymer 1 (4.0) | PGMEA (2,200) GBL (300) | 85 | 27 | 3.1 |
| | 1-7 | Polymer 1 (100) | PAG 10 (8.0) | Quencher 1 (4.50) | Water-repellent polymer 1 (4.0) | PGMEA (2,200) GBL (300) | 85 | 38 | 3.1 |
| | 1-8 | Polymer 1 (100) | PAG 11 (10.0) | Quencher 1 (4.50) | Water-repellent polymer 1 (4.0) | PGMEA (2,200) GBL (300) | 85 | 39 | 2.9 |
| | 1-9 | Polymer 1 (100) | PAG 12 (10.0) | Quencher 1 (4.50) | Water-repellent polymer 1 (4.0) | PGMEA (2,200) GBL (300) | 85 | 35 | 2.9 |
| | 1-10 | Polymer 2 (100) | PAG 2 (8.0) | Quencher 1 (4.50) | Water-repellent polymer 2 (4.0) | PGMEA (2,200) GBL (300) | 100 | 36 | 2.9 |
| Comparative Example | 1-1 | Polymer 1 (100) | c-PAG 1 (8.0) | Quencher 1 (4.50) | Water-repellent polymer 1 (4.0) | PGMEA (2,200) GBL (300) | 85 | 37 | 4.3 |
| | 1-2 | Polymer 1 (100) | c-PAG 2 (8.0) | Quencher 1 (4.50) | Water-repellent polymer 1 (4.0) | PGMEA (2,200) GBL (300) | 85 | 38 | 4.6 |
| | 1-3 | Polymer 1 (100) | c-PAG 3 (8.0) | Quencher 1 (4.50) | Water-repellent polymer 1 (4.0) | PGMEA (2,200) GBL (300) | 85 | 38 | 4.1 |
| | 1-4 | Polymer 2 (100) | c-PAG 2 (8.0) | Quencher 1 (4.50) | Water-repellent polymer 2 (4.0) | PGMEA (2,200) GBL (300) | 100 | 42 | 6.0 |

ArF Immersion Lithography Patterning Test

Examples 1-1 to 1-10 and Comparative Examples 1-1 to 1-4

On a substrate (silicon wafer), a spin-on carbon film ODL-102 (Shin-Etsu Chemical Co., Ltd.) having a carbon EUV Lithography Test Examples 2-1 to 2-6 and Comparative Example 2-1

The resist composition in Table 2 was spin coated on a silicon substrate having a 20-nm coating of spin-on-hard-mask material SHB-A940 (Shin-Etsu Chemical Co., Ltd.)

having a silicon content of 43 wt % and prebaked on a hotplate at 105° C. for 60 seconds to form a resist film of 60 nm thick. Using an EUV scanner NXE3300 (ASML, NA 0.33, σ 0.9/0.6, quadrupole illumination), the resist film was exposed to EUV through a mask having a hole pattern with a pitch of 46 nm and a size of 23 nm+20% bias (on-wafer size). The resist film was baked (PEB) on a hotplate at the temperature shown in Table 2 for 60 seconds and developed in a 2.38 wt % TMAH aqueous solution for 30 seconds to form a hole pattern having a size of 23 nm.

The resist pattern was evaluated under CD-SEM (CG-5000, Hitachi High-Technologies Corp.). The exposure dose that provides a hole pattern having a size of 23 nm is reported as sensitivity. The size of 50 holes at that dose was measured, from which a size variation (3σ) was computed and reported as CDU.

The resist composition is shown in Table 2 together with the sensitivity and CDU of EUV lithography.

TABLE 2

| | | Polymer (pbw) | Acid generator (pbw) | Quencher (pbw) | Organic solvent (pbw) | PEB temp. (° C.) | Sensitivity (mJ/cm$^2$) | CDU (nm) |
|---|---|---|---|---|---|---|---|---|
| Example | 2-1 | Polymer 3 (100) | PAG 7 (10.0) | Quencher 2 (3.00) | PGMEA (400) CyH (2,000) PGME (100) | 100 | 18 | 2.8 |
| | 2-2 | Polymer 3 (100) | PAG 8 (10.0) | Quencher 3 (3.00) | PGMEA (400) CyH (2,000) PGME (100) | 100 | 22 | 2.6 |
| | 2-3 | Polymer 3 (100) | PAG 9 (10.0) | Quencher 3 (3.00) | PGMEA (2,000) DAA (500) | 100 | 23 | 2.5 |
| | 2-4 | Polymer 3 (100) | PAG 10 (10.0) | Quencher 3 (3.00) | PGMEA (2,000) DAA (500) | 100 | 20 | 2.2 |
| | 2-5 | Polymer 3 (100) | PAG 11 (10.0) | Quencher 3 (3.00) | PGMEA (2,000) DAA (500) | 100 | 19 | 2.6 |
| | 2-6 | Polymer 3 (100) | PAG 12 (10.0) | Quencher 3 (3.00) | PGMEA (2,000) DAA (500) | 100 | 17 | 2.8 |
| Comparative Example | 2-1 | Polymer 3 (100) | c-PAG 4 (10.0) | Quencher 3 (3.00) | PGMEA (400) CyH (2,000) PGME (100) | 100 | 30 | 4.0 |

It is demonstrated in Tables 1 and 2 that resist compositions comprising a sulfonium or iodonium salt of fluorobenzenesulfonic acid bonded to iodized benzoic acid within the scope of the invention offer a high sensitivity and improved LWR and CDU.

Japanese Patent Application No. 2017-055799 is incorporated herein by reference.

Although some preferred embodiments have been described, many modifications and variations may be made thereto in light of the above teachings. It is therefore to be understood that the invention may be practiced otherwise than as specifically described without departing from the scope of the appended claims.

The invention claimed is:

1. A resist composition comprising a base polymer, a quencher, and a sulfonium salt having the formula (A-1) or an iodonium salt having the formula (A-2):

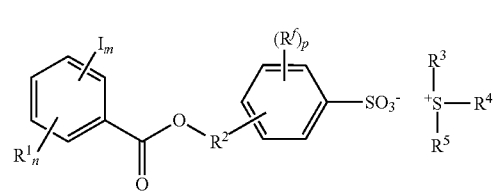

(A-1)

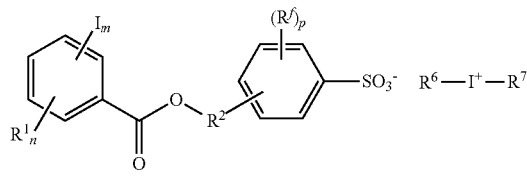

(A-2)

wherein $R^1$ is a hydroxyl group, carboxyl group, fluorine, chlorine, bromine, amino group, or a straight, branched or cyclic $C_1$-$C_{20}$ alkyl, $C_1$-$C_{20}$ alkoxy, $C_2$-$C_{20}$ alkoxycarbonyl or $C_2$-$C_{20}$ acyloxy group which may contain fluorine, chlorine, bromine, hydroxyl, amino or alkoxy moiety, or —$NR^9$—C(═O)—$R^{10}$ or —$NR^9$—C(═O)—O—$R^{10}$, $R^9$ is hydrogen, or a straight, branched or cyclic $C_1$-$C_6$ alkyl group, $R^{10}$ is a straight, branched or cyclic $C_1$-$C_{16}$ alkyl, straight, branched or cyclic $C_2$-$C_{16}$ alkenyl, or $C_6$-$C_{12}$ aryl group which may contain halogen, hydroxyl, alkoxy, acyl or acyloxy moiety, $R^2$ is a single bond, or a divalent $C_1$-$C_{20}$ linking group which may contain oxygen, sulfur or nitrogen, $R^f$ is fluorine or trifluoromethyl, $R^3$, $R^4$ and $R^5$ are each independently fluorine, chlorine, bromine, iodine, $C_1$-$C_{12}$ straight, branched or cyclic alkyl group, $C_2$-$C_{12}$ straight, branched or cyclic alkenyl group, $C_6$-$C_{20}$ aryl group, or $C_7$-$C_{12}$ aralkyl or aryloxyalkyl group, at least one hydrogen in the foregoing groups being optionally substituted by hydroxyl, carboxyl, halogen, oxo, cyano, amide, nitro, sultone, sulfone, or sulfonium salt-containing moiety, or at least one carbon in the foregoing groups being optionally substituted by an ether, ester, carbonyl, carbonate or sulfonate moiety, or $R^3$ and $R^4$ may bond together to form a ring with the sulfur atom to which they are attached, $R^6$ and $R^7$ are each independently trifluoromethyl, a $C_6$-$C_{10}$ aryl group, $C_2$-$C_6$ alkenyl group, or $C_2$-$C_6$ alkynyl group, at least one hydrogen in the foregoing groups being optionally substituted by a halogen, trifluoromethyl, $C_1$-$C_{10}$ straight, branched or cyclic alkyl or alkoxy, hydroxyl, carboxyl, alkoxycarbonyl, nitro or cyano moiety, m is an integer of 1 to 5, n is an integer of 0 to 3, and p is an integer of 1 to 4.

2. The resist composition of claim 1, further comprising an organic solvent.

3. The resist composition of claim 1 wherein the base polymer comprises recurring units having the formula (a1) or recurring units having the formula (a2):

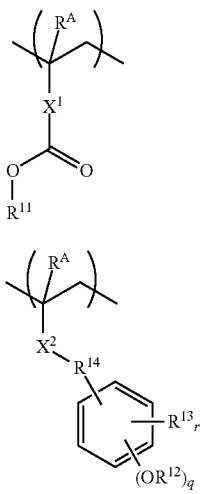

wherein $R^A$ is each independently hydrogen or methyl, $X^1$ is a single bond, phenylene group, naphthylene group, or $C_1$-$C_{12}$ linking group containing an ester moiety and/or lactone ring, $X^2$ is a single bond or ester group, $R^{11}$ and $R^{12}$ each are an acid labile group, $R^{13}$ is fluorine, trifluoromethyl, cyano, $C_1$-$C_6$ straight, branched or cyclic alkyl or alkoxy group, or $C_2$-$C_7$ straight, branched or cyclic acyl, acyloxy or alkoxycarbonyl group, $R^{14}$ is a single bond or a $C_1$-$C_6$ straight or branched alkylene group in which at least one carbon may be substituted by an ether or ester moiety, q is 1 or 2, and r is an integer of 0 to 4.

4. The resist composition of claim 3, further comprising a dissolution inhibitor.

5. The resist composition of claim 3 which is a chemically amplified positive resist composition.

6. The resist composition of claim 1 wherein the base polymer is free of an acid labile group.

7. The resist composition of claim 6, further comprising a crosslinker.

8. The resist composition of claim 6 which is a chemically amplified negative resist composition.

9. The resist composition of claim 1, further comprising a surfactant.

10. The resist composition of claim 1 wherein the base polymer further comprises recurring units of at least one type selected from the formulae (f1) to (f3):

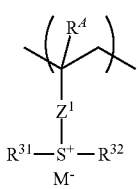

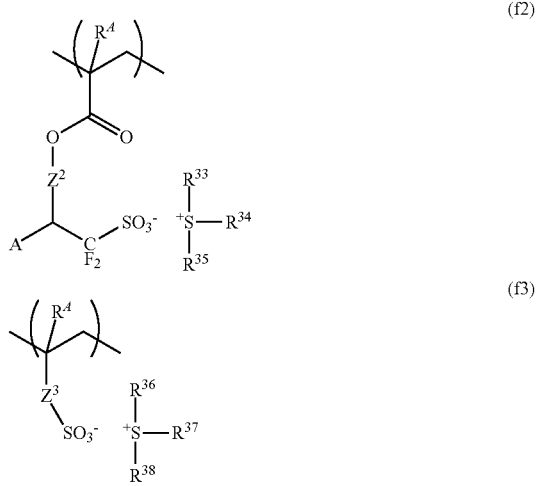

wherein $R^A$ is each independently hydrogen or methyl, $Z^1$ is a single bond, phenylene group, —O—$Z^{12}$— or —C(=O)—$Z^{11}$-$Z^{12}$—, $Z^{11}$ is —O— or —NH—, $Z^{12}$ is a $C_1$-$C_6$ straight, branched or cyclic alkylene group, $C_2$-$C_6$ straight, branched or cyclic alkenylene group or phenylene group, which may contain a carbonyl, ester, ether or hydroxy moiety, $R^{31}$ to $R^{38}$ are each independently a $C_1$-$C_{12}$ straight, branched or cyclic alkyl group which may contain a carbonyl, ester or ether moiety, or a $C_6$-$C_{12}$ aryl group or $C_7$-$C_{20}$ aralkyl group, in which at least one hydrogen may be substituted by a $C_1$-$C_{10}$ straight, branched or cyclic alkyl moiety, halogen, trifluoromethyl, cyano, nitro, hydroxyl, mercapto, $C_1$-$C_{10}$ straight, branched or cyclic alkoxy moiety, $C_2$-$C_{10}$ straight, branched or cyclic alkoxycarbonyl moiety, or $C_2$-$C_{10}$ straight, branched or cyclic acyloxy moiety, any two of $R^{33}$, $R^{34}$ and $R^{35}$, or any two of $R^{36}$, $R^{37}$ and $R^{38}$ may bond together to form a ring with the sulfur atom to which they are attached, $Z^2$ is a single bond, —$Z^{21}$—C(=O)—O—, —$Z^{21}$—O— or —$Z^{21}$—O—C(=O)—, $Z^{21}$ is a $C_1$-$C_{12}$ straight, branched or cyclic alkylene group which may contain a carbonyl, ester or ether moiety, A is hydrogen or trifluoromethyl, $Z^3$ is a single bond, methylene group, ethylene group, phenylene group, fluorinated phenylene group, —O—$Z^{32}$—, or —C(=O)—$Z^{31}$-$Z^{32}$—, $Z^{31}$ is —O— or —NH—, $Z^{32}$ is a $C_1$-$C_6$ straight, branched or cyclic alkylene group, a phenylene, fluorinated phenylene or trifluoromethyl-substituted phenylene group, or $C_2$-$C_6$ straight, branched or cyclic alkenylene group, which may contain a carbonyl, ester, ether or hydroxyl moiety, and $M^-$ is a non-nucleophilic counter ion.

11. A process for forming a pattern comprising the steps of applying the resist composition of claim 1 onto a substrate, baking to form a resist film, exposing the resist film to high-energy radiation, and developing the exposed film in a developer.

12. The process of claim 11 wherein the high-energy radiation is ArF excimer laser radiation of wavelength 193 nm or KrF excimer laser radiation of wavelength 248 nm.

13. The process of claim 11 wherein the high-energy radiation is electron beam or extreme ultraviolet radiation of wavelength 3 to 15 nm.

* * * * *